(12) United States Patent
Amegadzie et al.

(10) Patent No.: US 7,902,356 B2
(45) Date of Patent: Mar. 8, 2011

(54) THIAZOLOPYRIDINONE DERIVATES AS MCH RECEPTOR ANTAGONISTS

(75) Inventors: Albert Kudzovi Amegadzie, Indianapolis, IN (US); James Peter Beck, Zionsville, IN (US); Kevin Matthew Gardinier, Fishers, IN (US); Erik James Hembre, Indianapolis, IN (US); James Craig Ruble, Greenwood, IN (US); Kenneth Allen Savin, Indianapolis, IN (US); Brian David Wakefield, Skokie, IL (US)

(73) Assignee: Eli Lilly and Company, Indianapolis, IN (US)

( * ) Notice: Subject to any disclaimer, the term of this patent is extended or adjusted under 35 U.S.C. 154(b) by 813 days.

(21) Appl. No.: 11/721,079

(22) PCT Filed: Dec. 16, 2005

(86) PCT No.: PCT/US2005/045866
§ 371 (c)(1),
(2), (4) Date: Jun. 7, 2007

(87) PCT Pub. No.: WO2006/066174
PCT Pub. Date: Jun. 22, 2006

(65) Prior Publication Data
US 2009/0233919 A1    Sep. 17, 2009

Related U.S. Application Data

(60) Provisional application No. 60/637,143, filed on Dec. 17, 2004.

(51) Int. Cl.
*C07D 265/36* (2006.01)
*C07D 413/00* (2006.01)
*C07D 401/00* (2006.01)
*C07D 513/02* (2006.01)

(52) U.S. Cl. ............... 544/105; 544/128; 544/362; 546/114

(58) Field of Classification Search ............... 544/105, 544/128, 362; 546/114
See application file for complete search history.

(56) References Cited

FOREIGN PATENT DOCUMENTS

| EP | 1 283 199 | 2/2003 |
|----|-----------|--------|
| WO | 03/033476 | 4/2003 |
| WO | WO 03/033476 | 4/2003 |
| WO | WO 2004/052848 | 6/2004 |
| WO | 2005/047293 | 5/2005 |
| WO | 2007/093364 | 8/2007 |

OTHER PUBLICATIONS

Carpenter, et al., "Melanin-concentrating hormone receptor antagonists as potential antiob," Expert Opinion on Therapeutic Patents, Ashley Publications, GB, vol. 12, No. 11, pp. 1639-1646 (2002).
Dyck, et al., "A Thienopyridazinone-Based Melanin-Concentrating Hormone Receptor 1 Antagonist with Potent in Vivo Anorectic Properties," Journal of Medicinal Chemistry, American Chemical Society, vol. 49, No. 13, pp. 3753-3756 (2006).

*Primary Examiner* — Nizal S Chandrakumar
(74) *Attorney, Agent, or Firm* — Francis O. Ginah

(57) ABSTRACT

The present invention relates to a melanin concentrating hormone antagonist compound of formula (I); wherein w, $R^1$, q, p, $R^2$, t, $Ar^1$, $L^1$, $R^3$ and $R^4$ are as defined, or a pharmaceutically acceptable salt, solvate, or enantiomer thereof useful in the treatment, prevention or amelioration of symptoms associated with obesity and related diseases.

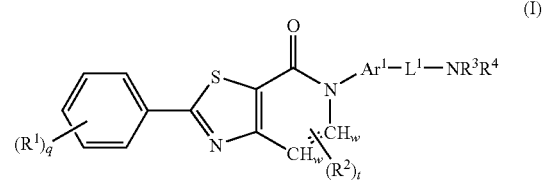

11 Claims, No Drawings

THIAZOLOPYRIDINONE DERIVATES AS MCH RECEPTOR ANTAGONISTS

This is the national phase application, under 35 USC 371, for PCT/US2005/045866, filed 16 Dec. 2005, which, claims the benefit, under 35 USC 119(e), of U.S. Provisional application No. 60/637,143, filed 17 Dec. 2004.

FIELD OF INVENTION

The present invention is in the field of medicine, particularly in the treatment of obesity and diseases caused by or exacerbated by obesity. More specifically, the present invention relates to antagonists of melanin concentrating hormone useful in the prevention and treatment of obesity and related diseases.

BACKGROUND OF THE INVENTION

The affluence of the 1990's along with the exponential increase in food production particularly in Western and Asian economies has resulted in feed patters that lead to obesity. Obesity is defined as being excessively overweight. Excessive weight is generally characterized by excessive body fat because unused energy is stored in the adipose tissues as fat.

Obesity has associated with it, economic and social costs. Obese people, an increasing proportion of developed and developing societies, are regarded as having out of control feeding habits often associated with low self-esteem. Moreover, obese persons are more likely to have medical problems associated with or exacerbated by the excess body weight. Examples of medical conditions caused, exacerbated or triggered by excessive weight include bone fractures, pains in the knee joints, arthritis, increased risk of hypertension, atherosclerosis, stroke, diabetes, etc.

Melanin concentrating hormone (MCH) is a 19 amino acid neuropeptide produced in the lateral hypothalamic area and zona incerta. Although MCH-expressing neurons project to numerous regions of the brain. MCH is processed from a larger pre-prohormone that also includes a second peptide, NEI, and possibly a third, NGE (Nahon, Crit Rev in Neurobiology, 8:221-262, 1994). MCH mediates its effects through at least two G protein-coupled receptors, MCHR1 and MCHR2 (Saito et al. Nature 400: 265-269, 1999; Hill et al., J Biol Chem. 276: 20125-20129, 2001). Both receptors are expressed in regions of the brain consistent with MCH neuronal projection and known MCH physiologic function (Hervieu et al., Eur J Neuroscience 12: 1194-1216, 2000; Hill et al., J Biol. Chem. 276: 20125-20129, 2001; Sailer et al., Proc Nat Acad. Sci. 98: 7564-7569, 2001).

Extensive evidence exists to support the orexigenic activity of MCH. MCH mRNA is elevated in rodent models of obesity and in the fasted state (Qu et al., Nature 380: 243-247, 1996). Intra-cerebroventricularly administered MCH increases feeding and blocks the anorexic effect of α-melanocyte stimulating hormone (Ludwig et al., Am J Physiol 274: E627-E633, 1998). MCH knockout mice (MCH$^{-/-}$ mice) are lean, hypophagic and hypometabolic (Shimada et al., Nature 396: 670-674, 1998), while MCH over-expressing transgenic mice are obese and insulin resistant (Ludwig et al., J Clin Invest 107: 379-386, 2001). MCHR1$^{-/-}$ mice have recently been reported to be lean and hypermetabolic, indicating that the R1 isoform mediates at least some of the metabolic effects of MCH (Marsh et al., Proc Nat Acad Sci 99: 3240-3245, 2002).

In addition to its effects on feeding, MCH has been implicated in regulation of the hypothalamic-pituitary-adrenal axis through modulation of CRF and ACTH release (Bluet-Pajot et al., J Neuroendocrinol 7: 297-303, 1995). MCH may also play a role in the modulation of reproductive function (Murray et al., J Neuroendocrinol 12: 217-223, 2000) and memory (Monzon et al., Peptides 20: 1517-1519, 1999).

The current preferred treatment for obesity as well as Type II non-insulin dependent diabetes is diet and exercise with a view toward weight reduction and improved insulin sensitivity for diabetics. Patient compliance, however, is usually poor. The problem is compounded by the fact that there are currently only two medications approved for the treatment of obesity (sibutramine, or Meridia™ and orlistat, or Xenical™.

PCT application number WO 01/21577 (JP00/06375) filed Sep. 19, 2000, discloses compounds reportedly useful as antagonists of the MCH receptor. In particular the WO 01/21577 application claims a compound of formula A

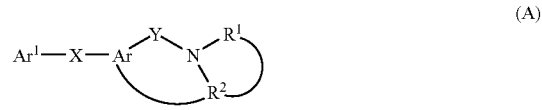

(A)

wherein:

Ar$^1$ is a cyclic group that may have substituents;

X is a spacer having a main chain of 1 to 6 atoms;

Y is a bond or a spacer having a main chain of 1 to 6 atoms;

Ar is a monocyclic aromatic ring which may be condensed with a 4 to 8 membered non-aromatic ring, and may have further substituents;

R$^1$ and R$^2$ are independently hydrogen atom or a hydrocarbon group which may have substituents;

R$^1$ and R$^2$ together with the adjacent nitrogen atom may form a nitrogen-containing hetero ring which may have substituent; R$^2$ may form a spiro ring together with Ar; or R$^2$, together with the adjacent nitrogen atom and Y, may form a nitrogen-containing hetero ring which may have substituents; or salts thereof.

PCT application number WO 01/82925, filed Apr. 26, 2001, also discloses compounds reportedly useful as antagonists of the MCH receptor. In particular the WO 01/82925 application claims a compound of formula B

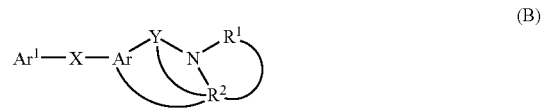

(B)

wherein:

Ar$^1$ is an optionally substituted cyclic group;

X and Y are independently a spacer having a C$_{1-6}$ main chain;

Ar is an optionally substituted fused polycyclic aromatic ring;

R$^1$ and R$^2$ are independently hydrogen atom or an optionally substituted hydrocarbon group; or alternatively R$^1$ and R$^2$ together with the nitrogen atom adjacent thereto may form a nitrogenous heterocycle, or R$^2$ together with the nitrogen atom adjacent thereto and Y may form an optionally substituted nitrogenous heterocycle, or R$^2$ together with the nitrogen atom adjacent thereto, Y, and Ar may form a fused ring.

PCT application number WO 01/87834, filed May 15, 2001, also discloses compounds reportedly useful as antagonists of the MCH receptor. In particular the WO 01/87834 application claims a compound of formula C.

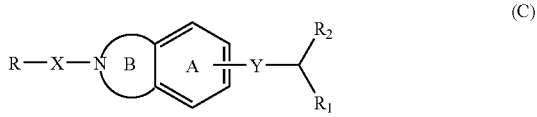

wherein;

R represents hydrogen, halogen, or an optionally substituted cyclic group; X represents a bond or a spacer in which the main chain has one to ten atoms; Y represents a spacer in which the main chain has one to six atoms; ring A represents a benzene ring which may have other substituents; ring B represents a five- to nine-membered nitrogen containing non-aromatic heterocycle which may have other substituents; and $R^1$ and $R^2$ are the same or different and each represents hydrogen, an optionally substituted hydrocarbon group, or an optionally substituted heterocyclic group, or $R^1$ and $R^2$ may form an optionally substituted nitrogenous heterocycle in cooperation with the adjacent nitrogen atom and $R^2$ may form an optionally substituted nitrogenous heterocycle in cooperation with the adjacent nitrogen atom and Y.

DE2502588 describes a compound of the formula:

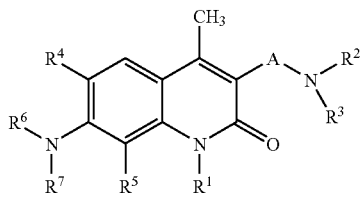

Wherein the variables are as defined therein.

PCT International publication WO 03/033476 A1 discloses a compound of the formula (Ia):

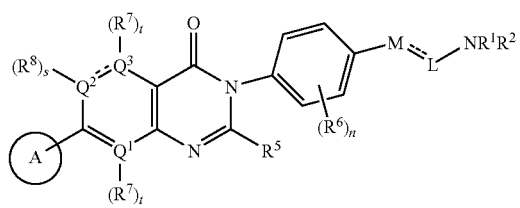

comprising a pharmaceutically acceptable salt, solvate, or physiologically functional derivative thereof, wherein the variables are as described therein.

Current treatments targeted at obesity have side effects. Examples of such treatments include various over-the-counter appetite suppressants. These agents have not been proven effective for all patients and for sustainable periods of time. Similarly, the approved treatments, sibutramine (Meridia™) and orlistat (Xenical™) have been associated with side effects which may compromise compliance and may preclude long term use for sustained weight loss for certain patient populations.

Therefore, there is a need for new and/or improved therapeutically effective agents useful as antagonists of melanin concentrating hormone to better control the dietary habits, minimize the preponderance of obesity and treat, prevent and/or ameliorate the effects of obesity, including for example diabetes.

SUMMARY OF INVENTION

The present invention relates to a compound of formula I:

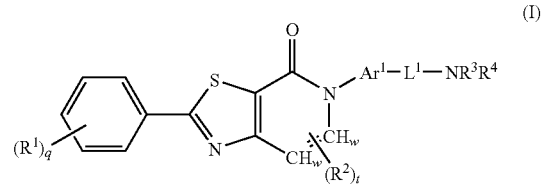

wherein:

"-----"is optionally a bond to form a double bond q is 0, 1, 2, or 3; wherein other positions on the phenyl ring have hydrogen atoms;

t is 1 or 2;

w is 1 or 2 depending on substitution pattern and/or the presence of a double bond;

$R^1$ is independently selected from the group consisting of hydrogen, $C_1$-$C_8$ alkyl, $C_2$-$C_8$ alkenyl, $C_2$-$C_8$ alkynyl, halo, hydroxy, $C_1$-$C_8$ haloalkyl, $C_1$-$C_8$ alkoxy, —$C_1$-$C_8$ alkyl alcohol, $C_1$-$C_8$ haloalkoxy, aryl, —O-aryl, —O-heteroaryl, —O$C_1$-$C_8$ alkylaryl, —$C_1$-$C_8$ alkylaryl, —$C_1$-$C_8$ alkylheteroaryl, heterocyclic, —$C_1$-$C_8$ alkylheterocyclic, cycloalkyl, —$C_1$-$C_8$ alkylcycloalkyl, amino, and $C_1$-$C_8$ alkyl$NR^6R^{6'}$, $C_0$-$C_8$ alkyl$COOR^6$, $C_o$-$C_8$ alkyl$CONR^6R^{6'}$;

$R^2$ is independently selected from the group consisting of hydrogen, halo, $C_1$-$C_6$ alkyl, $C_1$-$C_4$ haloalkyl, $C_2$-$C_4$ alkenyl, phenyl, and $C_1$-$C_4$ alkylaryl;

$Ar^1$ is a cyclic group optionally substituted with one to three groups independently selected from the group consisting of $C_1$-$C_8$ alkyl, $C_2$-$C_8$ alkenyl, $C_2$-$C_8$ alkynyl, hydroxy, —O$C_1$-$C_8$ alkyl, $C_1$-$C_8$ alkylaryl, $C_1$-$C_8$ alkylheteroaryl, phenyl, —O-aryl, —O-heteroaryl, heterocyclic, $C_1$-$C_4$ alkylheterocyclic, cycloalkyl, $C_1$-$C_8$ alkylcycloalkyl, cyano, —$C_1$-$C_8$ alkyl$NR^6R^{6'}$, $C_1$-$C_8$ haloalkyl, $C_1$-$C_8$ alkyl alcohol, $C_1$-$C_8$ haloalkoxy, halo, $(CH_2)_nCOR^6$, —O$(CH_2)_nCHR^6R^{6'}$, $NR^6SO_2R^{6'}$, $(CH_2)_nNR^6SO_2R^{6'}$, and —$(CH_2)_nC(O)NR^6R^{6'}$;

$L^1$ is a bond or a divalent linker selected from the group consisting of $C_1$-$C_5$ alkyl, $C_2$-$C_5$ alkynyl, $C_2$-$C_5$ alkenyl, $C_0$-$C_5$ alkyl-S—$C_0$-$C_5$ alkyl, $C_0$-$C_5$ alkyl-S—$C_1$-$C_5$ alkylhalide, $C_0$-$C_5$ alkyl-$NR^6$—$C_0$-$C_5$ alkyl, $C_0$-$C_5$ alkyl-$NR^6$—$C_1$-$C_5$ alkyl-S—$C_0$-$C_5$ alkyl wherein each $L^1$ group has a maximum of 6 carbon atoms in the main chain and wherein each alkyl is optionally substituted with 1 to 3 groups independently selected from halo, cyano, and hydroxy;

$R^3$ and $R^4$ are independently selected from the group consisting of hydrogen, $C_1$-$C_8$ alkyl, $C_2$-$C_8$ alkenyl, $C_3$-$C_8$ cycloalkyl, aryl, heteroaryl, heterocyclic, $C_1$-$C_8$ alkylaryl, $C_1$-$C_8$ alkylcycloalkyl, $C_1$-$C_8$ alkylheteroaryl, $C_1$-$C_4$ alkylheterocyclic; wherein each of the alkyl, alkenyl, cycloalkyl, aryl, heteroaryl, or heterocyclic group or subgroup is optionally substituted with one to three groups independently selected from $C_1$-$C_8$ alkyl, $C_2$-$C_8$ alkenyl, phenyl, alkylaryl, $(CH_2)_nNSO_2C_1$-$C_8$ alkyl, $(CH_2)_nNSO_2$phenyl, $(CH_2)_nNSO_2$aryl, —C(O)$C_1$-$C_8$ alkyl, COOH, —C(O)O$C_1$-$C_8$ alkyl and $C_0$-$C_4$ alkylNR$^6$R$^{6'}$; and wherein R$^3$ and R$^4$ optionally combine together with the nitrogen atom to which they are attached to form an optionally substituted nitrogen containing 5 to 7-member heterocyclic, or one or both of R$^3$ and R$^4$ combine with L$^1$ at a position α, β, γ, or, δ (e.g. 1, 2, 3, or 4 positions adjacent) to the nitrogen of NR$^3$R$^4$ to form a nitrogen containing 5 to 7-member heterocyclic group with L$^1$ said heterocyclic groups optionally having one to three substituents independently selected from oxo, hydroxy, cyano, $C_1$-$C_8$ alkyl, $C_2$-$C_8$ alkenyl, $C_3$-$C_8$ cycloalkyl, $C_1$-$C_8$ alkylaryl, $C_1$-$C_8$ alkylcycloalkyl, $C_1$-$C_4$ alkylheterocyclic, $C_1$-$C_4$ alkylheteroaryl, halo, $(CH_2)_nNSO_2C_1$-$C_8$ alkyl, $(CH_2)_nNSO_2$phenyl, $(CH_2)_nNSO_2$aryl, —C(O)$C_1$-$C_8$ alkyl, —C(O)O$C_1$-$C_8$ alkyl and $C_0$-$C_4$ alkylNR$^6$R$^{6'}$;

R$^6$ and R$^{6'}$ are independently selected from the group consisting of hydrogen, $C_1$-$C_8$ alkyl, phenyl, aryl, $C_1$-$C_8$ alkylaryl, $C_3$-$C_8$ cycloalkyl, or $C_1$-$C_6$ alkylcycloalkyl; and wherein R$^6$ and R$^{6'}$ may combine to form a 5-7 member nitrogen-containing heterocycle optionally having one to three substituents independently selected from oxo, hydroxy, cyano, $C_1$-$C_8$ alkyl, $C_2$-$C_8$ alkenyl, $C_3$-$C_8$ cycloalkyl, $C_1$-$C_8$ alkylaryl, $C_1$-$C_8$ alkylcycloalkyl, $C_1$-$C_4$ alkylheterocyclic, halo, $(CH_2)_nNSO_2C_1$-$C_8$ alkyl, $(CH_2)_nNSO_2$phenyl, $(CH_2)_nNSO_2$aryl, —C(O)$C_1$-$C_8$ alkyl, COOH, or —C(O)O$C_1$-$C_8$ alkyl and $C_0$-$C_4$ alkylNR$^7$R$^8$;

R$^7$ and R$^8$ are each independently selected from hydrogen, and $C_1$-$C_4$ alkyl; n is an integer from 0 to 4 wherever it occurs; or a pharmaceutically acceptable salt, solvate, enantiomer, diastereomer or mixture of or diastereomer thereof.

The present invention also relates to pharmaceutical compositions comprising a compound of formula I.

In another embodiment, the pharmaceutical composition of the present invention may be adapted for use in treating obesity and related diseases.

The present invention also relates to a method for treating and/or preventing obesity in a patient in need thereof, wherein such treatment comprises administering to said patient a therapeutically effective amount of a compound of formula I in association with a pharmaceutically acceptable carrier, diluent or excipient.

The present invention also relates to a method for antagonizing the binding of MCH to MCH receptors for the treatment of diseases caused, or exacerbated by melanin concentrating hormone.

The present invention provides the use of a compound of formula I as an appetite suppressant and/or as a weight loss agent.

The present invention is related to the use of a compound of formula I for the manufacture of a medicament for treating obesity and related diseases.

DETAILED DESCRIPTION

For the purposes of the present invention, as disclosed and/or claimed herein, the following terms are defined below.

The term "main chain" as used herein describes the number of atoms in the shortest distance between two ends of a variable or radical or linker and includes the distance in number of atoms when traversing a straight chain, branched chain or atoms in a mono or bicyclic ring from one end of the variable or radical to the other. As used herein the radical or group —CH$_2$CH$_2$OCH$_2$CH(CH$_2$CH$_2$CH$_3$)CH$_2$— has a chain length of 6.

General chemical terms used in the description of compounds herein described bear their usual meanings. For example, the term "$C_{1-8}$ alkyl," or "($C_1$-$C_8$)alkyl" or "$C_1$-$C_8$ alkyl" or as indicated refers to a straight or branched aliphatic chain of 1 to 8 carbon atoms including but not limited to methyl, ethyl, propyl, iso-propyl, n-butyl, pentyl, and the like as indicated. Unless otherwise stated, the term "alkyl" means $C_1$-$C_8$ alkyl. Similarly, the term "$C_0$-$C_8$ alkyl" implies an alkyl group as indicated wherein when the term $C_0$ applies, the alkyl group is not present, and the remaining groups attach directly to the substrate. For example, the group —$C_0$-$C_8$ alkylCONR$^{10}$R$^{11}$ implies that when $C_0$ applies, the group —$C_0$-$C_8$ alkylCONR$^{10}$R$^{11}$ becomes to —CONR$^{10}$R$^{11}$.

The invention also contemplates that the term $C_1$-$C_6$ alkyl or $C_2$-$C_6$ alkenyl or similar terms encompass the specified alkyl or alkenyl or similar group, which may be chiral, regio or steroisomeric. Such chiral or regio or stereoisomeric groups are also objects of the present invention.

The term "$C_3$-$C_8$ cycloalkyl" as used herein refers to a cyclic hydrocarbon radical or group having from 3 to 8 carbon atoms and having no double bonds. Examples of $C_3$-$C_8$ cycloalkyl groups include but are not limited to cyclopropyl, cyclobutyl, cyclopentyl, cyclohexyl, cycloheptyl, and cyclooctyl.

The term "$C_3$-$C_8$ cycloalkenyl" as used herein refers to a cyclic hydrocarbon radical or group having from 3 to 8 carbon atoms and having from 1 to 3 double bonds. Specific examples of $C_3$-$C_8$ cycloalkenyl include cyclopropenyl, cyclobutenyl, cyclopentenyl, cyclohexenyl, cycloheptenyl, and cyclooctenyl.

The term "halo" means halogens including iodo, chloro, bromo and fluoro.

The term "$C_1$-$C_4$ haloalkyl" refers to a $C_1$-$C_4$ alkyl (or as indicated) group substituted with one, two three or more halogen atoms as possible and chemically appropriate. Examples of $C_1$-$C_4$ haloalkyl include but are not limited to trifluoromethyl, chloroethyl, and 2-chloropropyl. Similarly, a "$C_1$-$C_8$ haloalkyl" group is a $C_1$-$C_8$ alkyl moiety substituted with up to six halo atoms, preferably one to three halo atoms.

A "$C_1$-$C_8$ alkoxy" group is a $C_1$-$C_8$ alkyl moiety connected through an oxy linkage. Examples of alkoxy groups include but are not limited to methoxy, ethoxy, propoxy, isopropoxy, butoxy, isobutoxy, sec-butoxy, pentyloxy, and hexyloxy.

The term "haloalkoxy", "$C_1$-$C_8$ haloalkyloxy", —O$C_1$-$C_8$ haloalkyl" or "halogenated $C_1$-$C_8$ alkoxy" means an alkoxy group having halogen substituents at one or more carbon atoms of the group. The term encompasses groups including for example, difluoromethoxy, trifluoromethoxy, 2-haloethoxy, 2,2,2-trifluoroethoxy, 4,4,4-trifluorobutoxy, up to and including the like groups having the indicated number of carbon atoms.

The term "cyclic" as used herein refers to substituted or unsubstituted aromatic (including heteroaromatic) and non-aromatic, carbocyclic or heterocyclic ring structures. Cyclic groups may also be monocyclic or bicyclic unless otherwise specified. Aromatic groups include, for example, benzene, thiophene, furan, pyrrole, imidazole, pyrazole, thiazole, isothiazole, oxazole, isoxazole, pyridine, pyrimidine, pyrazine, pyrimidine, pyridazine, napthyl, 1,2,4-oxadiazole, 1,3,4-oxadiazole, 1,2,4-thiadiazole, 1,3,4-thiadiazole, pyrrolidine, imidazoline, imidazolidine, pyrazoline, pyrazolidine, tetrahydrothiazole, tetrahydroisothiazole, tetrahydrooxazole, tetrahydroisoxazole, piperidine, tetrahydropyridine, dihydropyridine, piperazine, morpholine, thiomorpholine, tetrahydropyrimidine, tetrahydropyridazine, and hexamethyleneimine. Examples of bicyclic groups within the ambit of cyclic groups as used herein include benzofuran, benzimidazole, benzoxazole, benzothiophene, benzothiazole, benzisothiazole, naphtho[2,3-b]thiophene, naphthyl, isoquinoline, quinoline, indole, indazole, quinoxaline, phenanthridine, phenothiazine, phenoxathlin, phenoxazine, naphthylidene, quinazoline, carbazole, β-carboline, acridine, phenazine, phthalimide, and thioxanthene each of which may be optionally substituted. Cyclic groups as defined by $Ar^1$ are optionally substituted with one to five groups independently selected from $C_1$-$C_8$ alkyl, $C_2$-$C_8$ alkenyl, $C_2$-$C_8$ alkynyl, hydroxy, $C_1$-$C_8$ alkoxy, $C_1$-$C_8$ alkylaryl, phenyl, —O-aryl, heteroaryl, cycloalkyl, $C_1$-$C_8$ alkylcycloalkyl, cyano, —$(CH_2)_n NR^6 R^{6'}$, $C_1$-$C_8$ haloalkyl, —$OC_1$-$C_8$ haloalkyl, halo, $(CH_2)_n COR^6$, $(CH_2)_n NR^6 SO_2 R^6$, —$(CH_2)_n C(O)NR^6 R^6$, heterocyclic, and $C_1$-$C_8$ alkylheterocyclic; wherein the cycloalkyl, phenyl, aryl, and heterocyclic substituents are each optionally substituted with one to three groups independently selected from hydroxy, $C_1$-$C_8$ alkoxyalkyl, $C_1$-$C_8$ haloalkoxy, $C_1$-$C_8$ alkyl, halo, $C_1$-$C_8$ haloalkyl, nitro, cyano, amino, carboxamido, phenyl, aryl, alkylheterocyclic, heterocyclic, and oxo.

The term "alkylcycloalkyl" as used herein refers to an alkyl group on which a cycloalkyl group is substituted. Exemplary of alkylcycloalkyl groups are methylcyclopropyl, methylcyclohexyl, methylcycloheptyl, ethylcyclopropyl, etc. The alkylcycloalkyl group may optionally be substituted with one to five groups independently selected from $C_1$-$C_8$ alkyl, phenyl, aryl, halo, amino, alkylsulfonyl, alkyl sulfonamide, haloalkyl, carboxyalkyl, carboxamide, alkoxy, and perfluoroalkoxy.

The term "optionally substituted" as used herein and unless otherwise specified, means an optional substitution of one to five (or as specified), preferably 1 or 2 groups independently selected from halo, hydroxy, oxo, cyano, amino, alkylamino, nitro, phenyl, benzyl, aryl, —O-aryl, triazolyl, tetrazolyl, 4,5-dihydrothiazolyl, $C_1$-$C_6$ alkyl, $C_1$-$C_4$ haloalkyl, —$(CH_2)_n NR^6 R^{6'}$, $C_1$-$C_8$ haloalkyl, $C_1$-$C_8$ haloalkoxy, $(CH_2)_n COR^6$, $(CH_2)_n NR^6 SO_2 R^{6'}$, —$(CH_2)_n C(O) NR^6 R^{6'}$, heterocyclic, and $C_1$-$C_8$ alkylheterocyclic on the subject group, subgroup, or substituent and wherein $R^6$, $R^{6'}$ and n are as defined herein.

The term "heterocycle" or "heterocyclic" represents a stable, saturated, partially unsaturated, fully unsaturated, or aromatic 4, 5, or 6 or 7 membered ring or as otherwise specified. Such heterocyclic ring has from one to three heteroatoms that are independently selected from the group consisting of sulfur, oxygen, and nitrogen. The heterocycle may be attached at any point which affords a stable structure. Representative heterocycles include 1,3-dioxolane, 4,5-dihydro-1H-imidazole, 4,5-dihydrooxazole, furan, imidazole, imidazolidine, isothiazole, isoxazole, morpholine, oxadiazole, oxazole, oxazolidinedione, oxazolidone, piperazine, piperidine, pyrazine, pyrazole, pyrazoline, pyridazine, pyridine, pyrimidine, pyrrole, pyrrolidine, tetrazole, thiadiazole, thiazole, thiophene and triazole.

The heterocyclic group or heterocyle according to the present invention unless otherwise indicated is optionally substituted with one to three, preferably one or two groups independently selected from oxo, hydroxy, cyano, $C_1$-$C_8$ alkyl, $C_2$-$C_8$ alkenyl, $C_3$-$C_8$ cycloalkyl, $C_1$-$C_8$ alkylaryl, $C_1$-$C_8$ alkylcycloalkyl, $C_1$-$C_4$ alkylheterocyclic, $C_1$-$C_4$ alkylheteroaryl, halo, $(CH_2)_n NHSO_2 C_1$-$C_8$ alkyl, $(CH_2)_n NHSO_2 phenyl$, $(CH_2)_n NHSO_2 aryl$, —$C(O)C_1$-$C_8$ alkyl, —$C(O)OC_1$-$C_8$ alkyl and $C_0$-$C_4$ alkyl$NR^{6'}$ wherein $R^6$, $R^{6'}$ and n are as defined herein.

The term "alkylheterocyclic" as used herein refers to an alkyl group further substituted with a heterocyclic group. Examples of alkylheterocyclic include but are not limited to 2-methylimidazoline, N-methylmorpholinyl, N-methylpyrrolyl and 2-methylindolyl.

The term "nitrogen containing heterocyclic" means a heterocyclic ring having at least one nitrogen and include heterocyclic groups optionally having in addition to a nitrogen atom one or more of oxygen and sulfur atoms.

The term "oxo" as used herein implies an oxygen atom attached to a carbon atom which is part of a ring or a chain to form a carbonyl group.

The term "basic group" refers to an organic radical which is a proton acceptor. The term "basic group" also refers to an organic group containing one or more basic radicals. Illustrative basic radicals are amidino, guanidino, amino, piperidyl, pyridyl, etc, and exclude amides.

The term "suitable solvent" refers to any solvent, or mixture of solvents, inert to the ongoing reaction, that sufficiently solubilizes the reactants to afford a medium within which to effect the desired reaction.

As used herein, the term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Also included are exotic animals used in food production such as alligators, water buffalo and ratites (e.g., emu, rheas or ostriches). The preferred patient of treatment is a human.

The terms "treating" and "treat", as used herein, include their generally accepted meanings, e.g., preventing, prohibiting, restraining, alleviating, ameliorating, slowing, stopping, or reversing the progression or severity of a pathological condition, or sequela thereof.

The terms "preventing", "prevention of", "prophylaxis", "prophylactic" and "prevent" are used herein interchangeably and refer to reducing the likelihood that the recipient of a compound of formula I will incur or develop any of the pathological conditions, or sequela thereof, described herein.

As used herein, the term "effective amount" means an amount of a compound of formula I that is sufficient for treating or preventing a condition, or detrimental effects thereof herein described; or an amount of a compound of formula I that is sufficient for antagonizing the MCHR1 receptor to achieve the objectives of the invention.

The term "pharmaceutically acceptable" is used herein as an adjective and means substantially non-deleterious to the recipient patient.

The term "formulation", as in pharmaceutical formulation, is intended to encompass a product comprising the active ingredient(s) (compound(s) of formula I), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing a compound of the present invention and a pharmaceutical carrier, or a compound of formula I and a pharmaceutically acceptable co-antagonist of MCHR1 useful for the treatment and/or prevention of obesity or a related disease where antagonism of a MCH receptor may be beneficial.

The terms "diseases related to obesity" or "related diseases" as used herein refer to such symptoms, diseases or conditions caused by, exacerbated by, induced by, or adjunct to the condition of being obese. Such diseases, conditions and/or symptoms include but are not limited to eating disorders (bulimia, anorexia nervosa, etc.), diabetes, diabetic complications, diabetic retinopathy, sexual/reproductive disorders, depression, anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, and hyperlipoproteinenamia, stress related disorders including post traumatic stress disorder, substance abuse, including alcohol and drug abuse, and nonpharamcologic disorders such as gambling, sex and internet related addictions.

The term "unit dosage form" refers to physically discrete units suitable as unitary (i.e. individual, separate or separatable) dosages for human subjects and other non-human animals (as described above), each unit containing a predetermined quantity of active material/ingredient (compound of formula I) calculated to produce the desired therapeutic effect, in association with a suitable pharmaceutical carrier.

Certain compounds of the invention may contain an acidic moiety (e.g., carboxylic acid). Therefore, certain compounds of formula I may exist as a pharmaceutical base addition salts or ionic salts. Such salts include those derived from inorganic bases such as ammonium and alkali and alkaline earth metal hydroxides, carbonates, bicarbonates, and the like, as well as acid addition salts derived from basic organic amines such as aliphatic and aromatic amines, aliphatic diamines, hydroxy alkylamines, and the like. Methods of preparing and isolating salts are known to one of skill in the art. Pharmaceutically acceptable salts and common methodology for preparing them are well known to one of skill in the art. See, e.g. P. Stahl, et al. Handbook of Pharmaceutical Salts: Properties, Selections and Use (VCHA/Wiley-VCH, 200); S. M. Berge, et al., "Pharmaceutical Salts" Journal of Pharmaceutical Sciences, Vol. 66, No. 1, January 1977.

Preferred Compounds of the Invention

Certain compounds of the invention are particularly interesting and preferred. The following listing sets out several groups of preferred compounds. It will be understood that each of the listings may be combined with other listings or groupings described herein to create additional groups of preferred compounds.

Preferred $R^1$ Groups

Preferred $R^1$ groups are independently selected from the group consisting of hydrogen, halo, hydroxy, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_3$-$C_8$ cycloalkyl, $C_3$-$C_8$ alkylcycloalkyl, heterocyclic, $C_1$-$C_6$ alkylheterocyclic, phenyl, benzyl, cyano, and $C_1$-$C_4$ alkylNR$^6$R$^{6'}$, and wherein each phenyl, aryl, cycloalkyl or heterocyclic group or subgroup is optionally substituted with 1 to 2 groups independently selected from halo, $C_1$-$C_4$ alkyl, amino, cyano, nitro, $C_1$-$C_6$ haloalkyl, or $C_1$-$C_6$ alkoxy haloalkyl.

Preferred $R^2$ Groups

Preferred $R^2$ groups are independently selected from the group consisting of hydrogen, or $C_1$-$C_6$ alkyl.

Preferred Ar$^1$

Preferred Ar$^1$ groups are selected from optionally substituted $C_3$-$C_8$ cycloalkyl, pyridinyl, indolyl, benzthiazolyl, pyrrolidinyl, imidazolinyl, imidazolidinyl, pyrazolyl, pyrazolidinyl, phenyl, piperidinyl, benzothiophenyl, benzofuranyl, naphthyl, benzimidazolyl, indolinyl, indazolyl, benztriazolyl, quinolinyl, isoquinolinyl, tetrahydroquinolinyl, tetrahydroisoquinolinyl, benzo[1,3]dioxolyl, dihydro-benzo[1,4]dioxinyl, 3,4-dihydro-2H-benzo[1,4]-oxazinyl, each optionally substituted with 1-3 groups independently selected from $C_1$-$C_6$ alkyl, $C_1$-$C_6$ alkylcycloalkyl, $C_1$-$C_6$ haloalkyl, hydroxy, alkoxyalkyl, cyano, halo, aryl, COOR$^6$, and CONR$^6$R$^{6'}$. Particularly preferred Ar$^1$ groups include phenyl, indolyl, benzthiazolyl, benzimidazolyl, benzotriazolyl, imidazolyl, indazolyl, quinolinyl, isoquinolinyl, tetrahydroquinolinyl, tetrahydroisoquinolinyl, benzo[1,3]dioxolyl, dihydro-benzo[1,4]dioxinyl, and 3,4-dihydro-2H-benzo[1,4]-oxazinyl optionally substituted with 1-3 groups independently selected from halogen, —OC$_1$-C$_4$ alkyl, C$_1$-C$_4$ haloalkyl, and —C$_0$-C$_4$ alkylamine.

Preferred $L_1$ Groups

A preferred $L_1$ group is selected from the group consisting of CH$_2$—, —C(O)—, CH$_2$CH$_2$—, —CH$_2$CH$_2$CH$_2$—, —CH$_2$CH$_2$Oalkyl, —SCH$_2$CH$_2$—, —OCH$_2$CH$_2$—, —OCH$_2$CH$_2$CH$_2$—, —O(CH$_2$)$_3$CH$_2$—, —OCH(Et) CH$_2$CH$_2$CH$_2$-, —OCH(iPr)CH$_2$CH$_2$CH$_2$—, -acetylene-CH$_2$—, —OCH(CH$_3$)CH$_2$CH$_2$SCH$_2$—, —O(CH$_2$)$_3$SCH (CH$_3$)—, —O(CH$_2$)$_2$SCH(CF$_3$)—, —OCH(CN)CH$_2$CH$_2$—, —NR$^6$CH$_2$CH$_2$—, —NR$^6$CH$_2$CH$_2$CH$_2$—, —NR$^6$(CH$_2$)$_3$ CH$_2$—, —NR$^6$CH(Et)CH$_2$CH$_2$CH$_2$-, —NR$^6$CH(iPr) CH$_2$CH$_2$CH$_2$, —NR$^6$CH(CH$_3$)CH$_2$CH$_2$SCH$_2$—, —NR$^6$ (CH$_2$)$_2$SCH(CF$_3$)—, —OCH(CH$_3$)CH(CH$_3$)—, —OC (CH$_3$)$_2$CH$_2$—, —OCH$_2$C(CH$_3$)$_2$—, —C(CH$_3$)$_2$CH$_2$CH$_2$—, and —CH$_2$CH$_2$C(CH$_3$)$_2$—, and —NR$^6$CH(CN)CH$_2$CH$_2$—.

Preferred $R^3$ and $R^4$ Groups

Preferred $R^3$ and $R^4$ groups are independently selected from the group consisting of hydrogen, $C_1$-$C_6$ alkyl, $C_2$-$C_6$ alkenyl, $C_3$-$C_8$ cycloalkyl, $C_1$-$C_8$ alkylcycloalkyl, phenyl, aryl, $C_1$-$C_6$ alkylaryl, heterocyclic, $C_1$-$C_6$ alkylheterocyclic, COR$^6$, SO$_2$R$^6$ and (CH$_2$)$_n$SO$_2$R$^6$.

Also preferred are $R^3$ and $R^4$ groups which combine with each other and the nitrogen atom to which they are attached to form an optionally substituted 5-7 member heterocyclic ring; or where one or both of $R^3$ and $R^4$ combine with $L_1$ at a position α, β, or γ to the nitrogen of NR$^3$R$^4$ to form an optionally substituted heterocyclic group selected from the group consisting of optionally substituted morpholino, thiomorpholino, pyrrole, 2H-pyrrole, 2-pyrroline, pyrrolidine, oxazole, oxadiazolyl, thiazole, imidazoline, imidazolidine, pyrazole, pyrazoline, piperazinyl, piperidinyl, pyrazinyl, pyrimidine, azepine, diazepine, pyridinyl, indolyl, N-methylpyrrolidinyl, benzthiazolyl, benzimidazolyl, and benzthiopheneyl.

Most preferred are $R^3$ and $R^4$ groups which singly or in combination with each other and the nitrogen atom to which they are attached form or are represented by groups independently selected from methyl, ethyl, propyl, isopropyl, isobutyl, cyclopentyl, cyclohexyl, N-morpholinyl, benzyl, pyridinyl, pyrrolidinyl, piperidinyl, N-methylpiperidinyl, and N-methylpiperazinyl, 2-methylthiazolyl, N-methylimidazolyl, and 4-piperidinylpiperidine.

Preferred $R^6$ Groups

A preferred $R^6$ or $R^{6'}$ is independently selected from hydrogen, $C_1$-$C_8$ alkyl, phenyl, aryl, alkylaryl, and $C_3$-$C_8$ cycloalkyl.

A more preferred compound of the invention is a compound of formula I wherein $R^1$ is methyl, chloro, methoxy, fluoro, trifluoromethyl, dichloro, N,N-dimethyl, or methylsulfonate;

W is 1 and p is 0 or 1;

$R^2$ is hydrogen; t is 0;

$Ar^1$ is selected from a group consisting of phenyl, benzimidazolyl, 1H-insazolyl, 2-methylindolyl, 3-methoxyphenyl, 2,3-dimethylindolyl, 1-methylindoluyl, benzo-1,4-oxazin, 4-methylquinolinyl-6yl, 2,3-dihydroindolyl, oxazolyl, 3-chlorophenyl, $L^1$ is selected from the group consisting of a bond, —C(O)—, —CH$_2$—, —CH$_2$CH$_2$—, —CH$_2$CH$_2$CH$_2$, —NHCH$_2$CH$_2$, —N(CH$_3$)CH$_2$CH$_2$, —OCH$_2$, —OCH$_2$CH$_2$, —OCH$_2$CH$_2$CH$_2$, and -acetyleneCH$_2$;

Preferably, $R^3$ and $R^4$ are independently selected from the group consisting of methyl, ethyl, isopropyl, cyclohexyl; or $R^3$ and $R^4$ combine with each other or with a carbon atom one to four atoms removed (α, β, or γ position) from the nitrogen of $NR^3R^4$ to form a cyclic ring selected from pyrrole, morpholino, piperidinyl, 4-bipiperidinyl, piperazinyl, pyridinyl, -morpholinyl-2yl, N-methylmorpholinyl-2yl, 3-hydroxypyrrolidin-1-yl, 3-methyl, -3H-imidazole, 1H-1-methylimidazolyl, pyridine-4-one, 4-hydroxy-piperidin-1-yl, pyridinyl, optionally containing 1 or 2 heteroatoms selected from O, N, or S.

An example of a preferred compound of the present invention is a compound selected from the group consisting of:

2-(4-Chloro-phenyl)-5-{4-[2-(isopropyl-methyl-amino)-ethoxy]-3-methoxy-phenyl}-6,7-dihydro-5H-thiazolo[5,4-c]pyridin-4-one, 2-(4-Chloro-phenyl)-5-[1-((S)-pyrrolidine-3-carbonyl)-2,3-dihydro-1H-indol-5-yl]-6,7-dihydro-5H-thiazolo[5,4-c]pyridin-4-one, triflate salt, 2-(4-Chloro-phenyl)-5-[4-(2-diethylamino-ethoxy)-3-methoxy-phenyl]-6,7-dihydro-5H-thiazolo[5,4-c]pyridin-4-one, 2-(4-Chloro-phenyl)-5-[3-methoxy-4-(2-pyrrolidin-1-yl-ethoxy)-phenyl]-6,7-dihydro-5H-thiazolo[5,4-c]pyridin-4-one, 5-[3-Methoxy-4-(3-methyl-3H-imidazol-4-ylmethoxy)-phenyl]-2-(4-trifluoromethoxy-phenyl)-5H-thiazolo[5,4-c]pyridin-4-one, hydrochloride salt, 2-(4-Chloro-phenyl)-5-{2-[methyl-(1-methyl-piperidin-4-yl)-amino]-benzooxazol-5-yl}-6,7-dihydro-5H-thiazolo[5,4-c]pyridin-4-one, hydrochloride salt 5-[3-Methoxy-4-(3-methyl-3H-imidazol-4-ylmethoxy)-phenyl]-2-(4-methoxy-phenyl)-5H-thiazolo[5,4-c]pyridin-4-one, hydrochloride salt, 2-(4-Methoxy-phenyl)-5-[3-methoxy-4-(2-pyrrolidin-1-yl-ethoxy)-phenyl]-6,7-dihydro-5H-thiazolo[5,4-c]pyridin-4-one, 2-(4-Chloro-phenyl)-5-[3-methoxy-4-(2-piperidin-1-yl-ethoxy)-phenyl]-6,7-dihydro-5H-thiazolo[5,4-c]pyridin-4-one, 2-(4-Chloro-phenyl)-5-{3-methoxy-4-[2-(3-oxo-morpholin-4-yl)-ethoxy]-phenyl}-5H-thiazolo[5,4-c]pyridin-4-one, 2-(4-Chloro-phenyl)-5-[4-(2-pyrrolidin-1-yl-ethyl)-3,4-dihydro-2H-benzo[1,4]oxazin-7-yl]-6,7-dihydro-5H-thiazolo[5,4-c]pyridin-4-one, 2-(2,4-Dichloro-phenyl)-5-[3-methoxy-4-(2-pyrrolidin-1-yl-ethoxy)-phenyl]-6,7-dihydro-5H-thiazolo[5,4-c]pyridin-4-one, 2-(4-Chloro-phenyl)-5-{2-[(2-dimethylamino-ethyl)-methyl-amino]-benzooxazol-5-yl}-6,7-dihydro-5H-thiazolo[5,4-c]pyridin-4-one, hydrochloride salt, 2-(4-Chloro-phenyl)-5-{4-[2-(cyclohexyl-methyl-amino)-ethoxy]-3-methoxy-phenyl}-6,7-dihydro-5H-thiazolo[5,4-c]pyridin-4-one, 2-(4-Chloro-phenyl)-5-[4-(3-dimethylamino-propoxy)-3-methoxy-phenyl]-6,7-dihydro-5H-thiazolo[5,4-c]pyridin-4-one, 2-(4-Chloro-phenyl)-5-[4-methyl-2-(2-morpholin-4-yl-ethylamino)-quinolin-6-yl]-6,7-dihydro-5H-thiazolo[5,4-c]pyridin-4-one, 2-(4-Chloro-phenyl)-5-[3-methoxy-4-(2-pyrrolidin-1-yl-ethoxy)-phenyl]-5H-thiazolo[5,4-c]pyridin-4-one, 2-(4-Chloro-phenyl)-5-[4-(2-dimethylamino-ethoxy)-3-methoxy-phenyl]-6,7-dihydro-5H-thiazolo[5,4-c]pyridin-4-one, 2-(4-Chloro-phenyl)-5-[1-(2-pyrrolidin-1-yl-ethyl)-1H-indol-5-yl]-6,7-dihydro-5H-thiazolo[5,4-c]pyridin-4-one, 2-(4-Chloro-phenyl)-5-[3-methoxy-4-(2-pyrrolidin-1-yl-ethoxy)-phenyl]-5H-thiazolo[5,4-c]pyridin-4-one citrate salt, 2-(4-Chloro-phenyl)-5-[3-chloro-4-(2-pyrrolidin-1-yl-ethoxy)-phenyl]-5H-thiazolo[5,4-c]pyridin-4-one, hydrochloride salt, 2-(4-Chloro-phenyl)-5-[3-methoxy-4-(2-pyrrolidin-1-yl-ethoxy)-phenyl]-5H-thiazolo[5,4-c]pyridin-4-one, hydrochloride salt, 2-(4-Chloro-phenyl)-5-[3-methoxy-4-(2-pyrrolidin-1-yl-ethoxy)-phenyl]-5H-thiazolo[5,4-c]pyridin-4-one, 2-(4-Chloro-phenyl)-5-[3-methoxy-4-(3-pyrrolidin-1-yl-propyl)-phenyl]-5H-thiazolo[5,4-c]pyridin-4-one, hydrochloride salt, 2-(4-Chloro-phenyl)-5-[3-methoxy-4-(2-morpholin-4-yl-ethoxy)-phenyl]-5H-thiazolo[5,4-c]pyridin-4-one, hydrochloride salt, 2-(4-Methoxy-phenyl)-5-[3-methoxy-4-(2-pyrrolidin-1-yl-ethoxy)-phenyl]-5H-thiazolo[5,4-c]pyridin-4-one, hydrochloride salt 2-(4-Chloro-phenyl)-5-[1-methyl-3-(2-pyrrolidin-1-yl-ethyl)-1H-indol-6-yl]-6,7-dihydro-5H-thiazolo[5,4-c]pyridin-4-one, hydrochloride salt, 5-[3-Methoxy-4-(2-pyrrolidin-1-yl-ethoxy)-phenyl]-2-(4-trifluoromethoxy-phenyl)-5H-thiazolo[5,4-c]pyridin-4-one, hydrochloride salt, 2-(4-Chloro-phenyl)-5-[3-methoxy-4-(3-pyrrolidin-1-yl-propyl)-phenyl]-5H-thiazolo[5,4-c]pyridin-4-one, 2-(4-Chloro-phenyl)-5-[4-(2-dimethylamino-ethoxy)-3-methoxy-phenyl]-6,7-dihydro-5H-thiazolo[5,4-c]pyridin-4-one, 2-(4-Chloro-phenyl)-5-[3-methoxy-4-(3-methyl-3H-imidazol-4-ylmethoxy)-phenyl]-5H-thiazolo[5,4-c]pyridin-4-one, hydrochloride salt, 2-(4-Chloro-phenyl)-5-[1-(2-pyrrolidin-1-yl-ethyl)-1H-indol-5-yl]-5H-thiazolo[5,4-c]pyridin-4-one, 2-(4-Chloro-phenyl)-5-{4-[2-(2,2-dimethyl-morpholin-4-yl)-ethoxy]-3-methoxy-phenyl}-5H-thiazolo[5,4-c]pyridin-4-one, hydrochloride salt, 5-[4-(2-Dimethylamino-ethoxy)-3-methoxy-phenyl]-2-(4-methoxy-phenyl)-6,7-dihydro-5H-thiazolo[5,4-c]pyridin-4-one, hydrochloride salt, 2-(4-Chloro-phenyl)-5-[1-methyl-3-(2-pyrrolidin-1-yl-ethyl)-1H-indol-6-yl]-6,7-dihydro-5H-thiazolo[5,4-c]pyridin-4-one, 2-(4-Chloro-phenyl)-5-[3-chloro-4-(2-pyrrolidin-1-yl-ethoxy)-phenyl]-6,7-dihydro-5H-thiazolo[5,4-c]pyridin-4-one, hydrochloride salt, 2-(4-Chloro-phenyl)-5-[3-methoxy-4-(3-pyrrolidin-1-yl-propyl)-phenyl]-6,7-dihydro-5H-thiazolo[5,4-c]pyridin-4-one, 2-(4-Chloro-phenyl)-5-[2-methyl-1-(2-pyrrolidin-1-yl-ethyl)-1H-indol-5-yl]-6,7-dihydro-5H-thiazolo[5,4-c]pyridin-4-one, 2-(4-Chloro-phenyl)-5-[3-methoxy-4-(3-pyrrolidin-1-yl-propyl)-phenyl]-6,7-dihydro-5H-thiazolo[5,4-c]pyridin-4-one, hydrochloride salt,
2-(4-Chloro-phenyl)-5-[3-methoxy-4-(3-pyrrolidin-1-yl-prop-1-ynyl)-phenyl]-6,7-dihydro-5H-thiazolo[5,4-c]pyridin-4-one,
5-[3-Methoxy-4-(2-pyrrolidin-1-yl-ethoxy)-phenyl]-2-(4-trifluoromethyl-phenyl)-6,7-dihydro-5H-thiazolo[5,4-c]pyridin-4-one,
2-(4-Chloro-phenyl)-5-{3-methoxy-4-[2-(2,2,6,6-tetramethyl-morpholin-4-yl)-ethoxy]-phenyl}-5H-thiazolo[5,4-c]pyridin-4-one, hydrochloride salt,
2-(4-Chloro-phenyl)-5-[1-(2-pyrrolidin-1-yl-ethyl)-1H-benzoimidazol-5-yl]-6,7-dihydro-5H-thiazolo[5,4-c]pyridinone,
2-(4-Chloro-phenyl)-5-[3-methoxy-4-((R)-1-morpholin-2-ylmethoxy)-phenyl]-6,7-dihydro-5H-thiazolo[5,4-c]pyridin-4-one, hydrochloride salt,
2-(4-Chloro-phenyl)-5-[2,3-dimethyl-1-(2-pyrrolidin-1-yl-ethyl)-1H-indol-5-yl]-6,7-dihydro-5H-thiazolo[5,4-c]pyridin-4-one,
5-[4-(2-[1,4']Bipiperidinyl-1'-yl-ethoxy)-3-methoxy-phenyl]-2-(4-chloro-phenyl)-6,7-dihydro-5H-thiazolo[5,4-c]pyridin-4-one,
2-(4-Chloro-phenyl)-5-[1-(2-morpholin-4-yl-ethyl)-1H-indol-5-yl]-6,7-dihydro-5H-thiazolo[5,4-c]pyridin-4-one, hydrochloride salt, or a pharmaceutically acceptable salt, solvate, enantiomer, or mixture of enantiomers thereof.

Preparing Compounds of the Invention

Scheme 1 shows a synthetic route for preparing a common intermediate VI generally utilized in the preparation of compounds of the invention.

Preparation of the intermediate VI starts with the condensation of thioamide I and β-keto ester II as shown in step 1. This can be achieved in polar solvent (such as MeOH, EtOH or DMF) from about 2 to 24 hours (h) at a temperature range from about room temperature to 80° C. to give a thiazole of formula III.

In step 2, reduction of the ester III to the alcohol IV can be achieved using one of several methods well known in the literature. For example, ester III can be reduced with DIBAL (or other suitable reducing agent like $LiAlH_4$, $NaBH_4$, and LiBH4) in THF (or other aprotic solvent such as ether or toluene) from about 1 to 8 h at a temperature range from about −78° C. to 60° C. Compound IV is isolated by aqueous work-up and purified by means known in the art.

As shown in step 3, carboxylic acid V can be prepared from alcohol IV by dissolving in THF (or ether) at about −78° C., slowly treating with a solution of n-BuLi (or other suitable base such as LDA or HMDA) over about 2 to 4 hours, then treating with a solution of $CO_2$ (g) in THF (or ether). Compound V is isolated by precipitation from a dilute aqueous solution and purified by means known in the art.

The use of a Dean-Stark trap accelerates the reaction by removing $H_2O$ as it is produced.

Step 4 involves lactone formation to give VI using anhydrous conditions. For example, a solution of alcohol V in anhydrous toluene (or THF, benzene, etc.) is treated with an acid catalyst (ex. para-toluenesulfonic acid) and heated to reflux for 4 to 24 hours to cyclize to VI. The use of a Dean-Stark trap accelerates the reaction by removing $H_2O$ as it is produced.

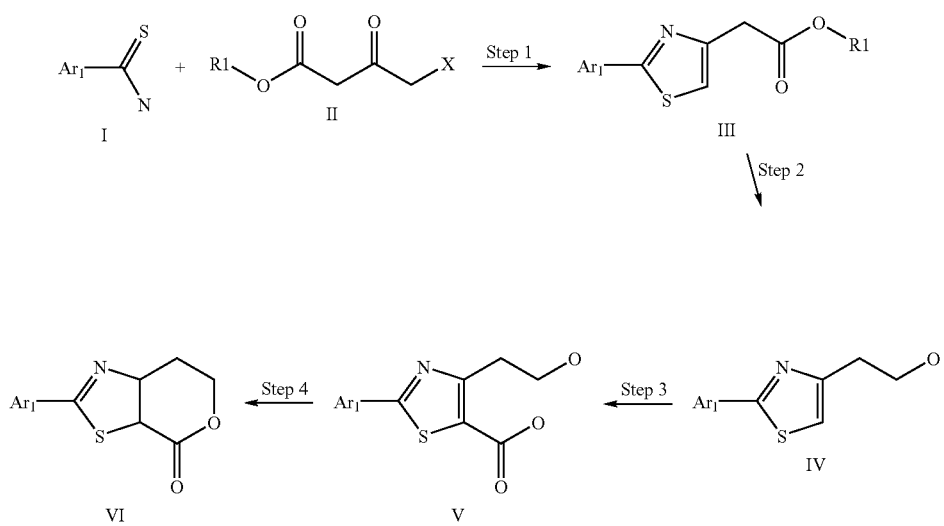

Scheme 2. Synthesis of lactam compounds of formula XIII (Route 1).

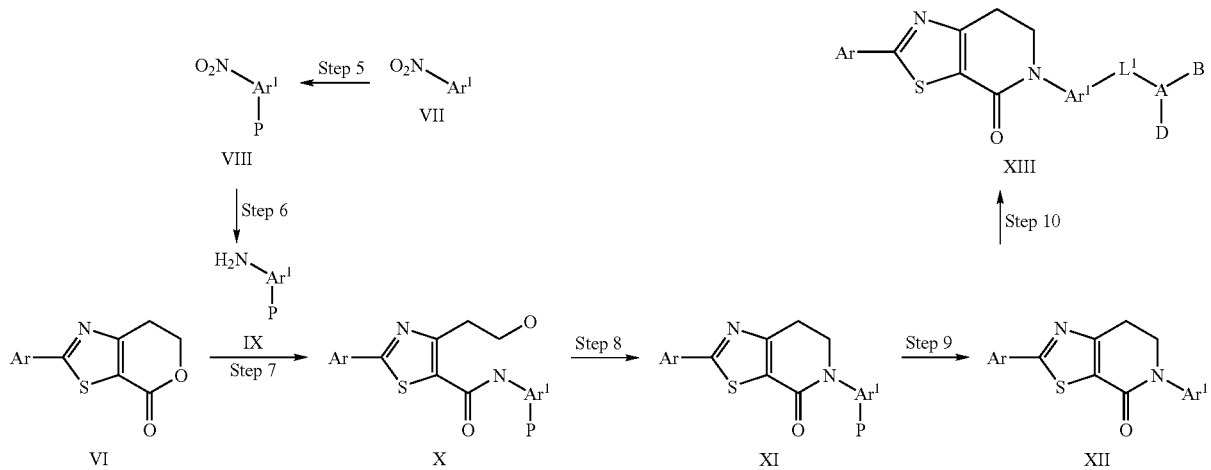

Lactone VI can be elaborated to provide compounds of formula XIII as shown in Scheme 2. In step 5, a nitro compound of formula VII that contains a free OH or NH group is protected with an appropriate group, to give compound of formula VIII that can be removed later in the synthetic sequence. For example, 2-methoxy-4-nitro-phenol is protected as a silyl ether by dissolving the phenol in a polar solvent such as DMF or THF, treating with a base such as sodium hydride, and then adding triisopropylsilyl triflate (or similar silyl reagent like TBSCl, TIPSCl, or TBSOTf). The reactions is stirred within a temperature range of about RT to 50° C. for 1 to 24 hours then isolated via aqueous work-up and purified by means known in the art. Other protecting groups for an OH or NH group can be employed and are familiar to those skilled in the art (see Philip J. Kocienski, "Protecting Groups," Thieme: New York 1994 or Theodora W. Green, "Protective Groups in Organic Synthesis," John Wiley and Sons: New York, 1981 for additional examples).

In step 6, a compound of formula VIII is prepared by reduction of the nitro group to give an amine of formula IX by treatment with 5-10% Pd/C under $H_2$ atmosphere (1 atm) in a suitable solvent (like THF, EtOAc, EtOH or MeOH) from about 2 to 24 hours at room temperature. Several other nitro reduction techniques known in the art can be employed.

Amide formation, as shown in step 7, is accomplished using a typical Weinreb protocol (see Basha, Anwer; Lipton, M.; Weinreb, Steven M. Tetrahedron Letters, 1977, 48, 4171-4174). For example, amine IX is dissolved in an aprotic solvent (such as $CH_2Cl_2$ or toluene) and treated with a 2-2.5M solution of $Me_3Al$ in hexanes. The resulting solution is stirred at a temperature from about 0° C. to room temperature for about 5 to 60 minutes, and then treated with lactone VI. The resulting solution is stirred at a range of between about room temperature and 110° C. for about 3 to 24 hours to give amide X which is isolated by aqueous work-up and purified by trituration with ether or by flash chromatography.

In step 8, lactam XI is prepared under Mitsunobu conditions (Maligres, P. E.; Waters, M. S.; Weissman, S. A.; McWilliams, J. C.; Lewis, S.; Cowen, J.; Reamer, R. A.; Volante, R. P.; Reider, P. J.; Askin, D. J. Het. Chem. 2003, 40 (2), 229-241). For example, amide X is dissolved in a suitable anhydrous solvent (ex. THF, $CH_2Cl_2$, toluene, etc.) and treated with a trialkyl- or triarylphosphine (ex. $Me_3P$, $Bu_3P$, or $Ph_3P$) and dialkylazo-dicarboxylate (ex. DEAD or DIAD) at a suitable temperature (about 0° C. to RT) for about 4 to 24 hours. Compound XI is isolated by aqueous workup and chromatographic purification.

In step 9, the protecting group that was installed in Step 5 is removed using conditions that are appropriate for the type of protecting group used to give compound of formula XII. For example, removal of a silyl ether, such as a triisopropylsilyl group, is achieved by dissolving the silyl ether in a polar solvent like THF or $CH_2Cl_2$ and treating with a fluoride source such as $nBu_4NF$ or HF.pyridine. The reaction is stirred from about 15 minutes to 4 hours at a temperature within a range of about 0 to 50° C. and is isolated by aqueous work-up and purified by means known in the art.

Compounds of formula XIII can be prepared by the alkylation of an NH or OH group (see step 10) by dissolving in a polar solvent (like THF, DMF, DMSO, and NMP) and treating with a base such as NaH or $K_2CO_3$ and an electrophile (e.g. alkyl halide, alkyl mesylate, or alkyl tosylate). The reaction is stirred within a range of about room temperature to about 100° C. from 4-24 hours and then isolated by aqueous work-up and purified by means known in the art.

Scheme 3. Synthesis of lactam compounds of formula XIII (Route 2).

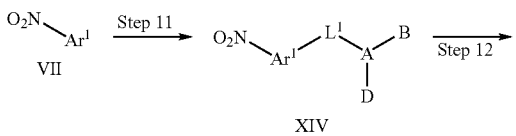

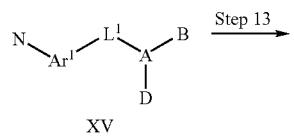

-continued

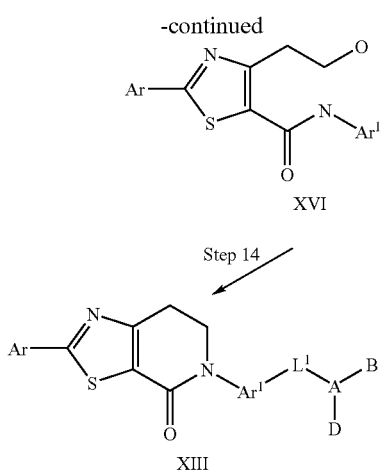

XVI

Step 14

XIII

Scheme 3 shows an alternative route to compounds of formula XIII. In this approach, the alkylation of an NH or OH group occurs early in the synthetic sequence. For example, alkylation of VII as shown in Step 11 occurs under conditions similar to step 8 above to give compounds of formula XIV.

In step 13, the nitro group is reduced to an amine as described in step 5. Also, step 13 and 14 proceed under similar conditions as described in steps 7 and 8, respectively, to ultimately provide compounds of formula XIII.

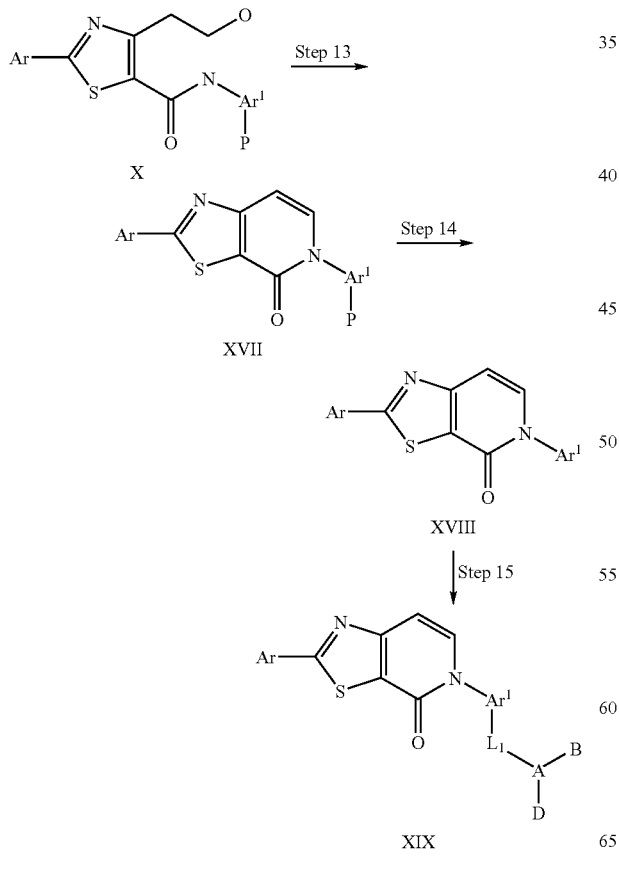

Schemes 4 and 5 show synthetic routes for preparing thiazole-pyridone compounds of the invention and/or precursors thereof.

In step 13 of scheme 4, pyridone XVII is prepared in one step by the oxidation of intermediate alcohol X. For example compound X is dissolved in a suitable polar solvent (e.g. $CH_2Cl_2$, THF) and treated with an oxidizing reagent (e.g. Dess-Martin periodinane, pyridine.$SO_3$, PDC, or under Swern-oxidation conditions). Oxidation conditions are abundantly known to those skilled in the art and can be found in *Comprehensive Organic Transformations*, by R. C. Larock, VCH Publishers, 1989, p. 604-614. Dess-Martin periodinane is the reagent of choice for this transformation and the oxidation is performed at about 0° C. to room temperature from about 1 hour to 3 days. Pyridone XVII is isolated by aqueous workup and chromatographic purification.

In step 14, analogous to step 9 above, removal of the protecting group to reveal an NH or OH group is achieved under similar conditions and the compound of formula XVIII is isolated by aqueous work-up and purified by means known in the art.

Alkylation of the OH or NH group of XVIII (step 15) can occur under basic conditions with an alkylating reagent, as described in step 10 above, or under Mitsunobu conditions to provide compounds of formula XIX.

Alternatively, and as shown in step 16 of Scheme 5, intermediate XVI can be oxidized with the sidechain already installed using similar conditions as described in step 13 above to afford thiazole-pyridone compounds of formula XIX.

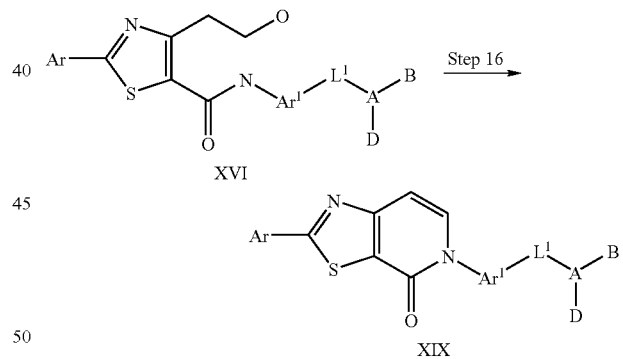

Scheme 6 shows a synthetic route for preparing compounds of the invention from an intermediate acetal wherein $L^1$ is an alkylene of varying carbon chain lengths.

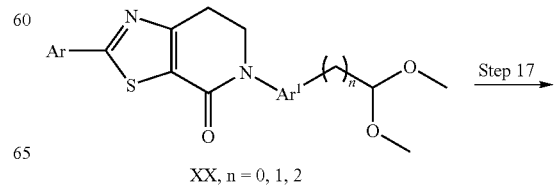

XX, n = 0, 1, 2

-continued

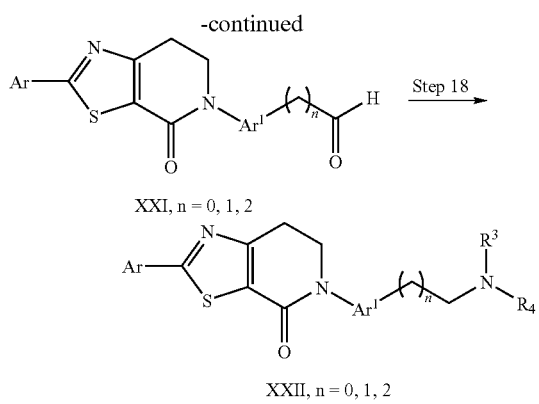

XXI, n = 0, 1, 2

XXII, n = 0, 1, 2

If groups A, B and D (Compound XIII) together define an acetal group (such as A=CH and B=D=OMe or OEt), then hydrolysis to an aldehyde group is performed according to conditions recognized by persons skilled in the art (Scheme 6). For example, in step 17 acetal XX is dissolved in a suitable solvent (e.g. THF, acetone, MeOH) and treated with water and an acid catalyst (e.g. p-toluenesulfonic acid) at reflux for about 4 to 24 hours to give aldehyde XXI. Reductive amination (step 18) is performed by dissolving the aldehyde XXI in dichloroethane or another suitable solvent such as for example, $CH_2Cl_2$ or THF and treated with an 1° or 2° amine and a reducing reagent such as for example $NaCNBH_3$, or $NaBH(OAc)_3$. The mixture is stirred at about RT to 80° C. from about 30 min to 8 hours. Amines of formula XXII are isolated by aqueous workup and purified by means known in the art.

Scheme 7 shows an alternative synthetic route for preparing compounds of the invention and/or precursors thereof. In step 19, lactone VI is treated with a protected amine using conditions previously described in step 7 to give amide XXIII. In step 19, Lactam XXIV is prepared using conditions previously described in step 8. The lactam nitrogen is deprotected, as shown in step 21, using conditions consistent with the type of protecting group that is used. For example, a 3,4-dimethoxy benzyl group is removed under acidic conditions (e.g. p-toluene sulfonic acid or TFA) in a solvent such as toluene at a temperature range of RT to reflux for 0.5 to 4 h. Lactam XXIV is isolated by precipitation from water and purified by means known in the art.

In step 22, the lactam is coupled to an aryl bromide using catalytic cross-coupling conditions such as Buchwald arylation of an amide (see Yin, J.; Buchwald, S. J. *J. Am. Chem. Soc.* 2002, 124 (21), 6043-6048). For example, lactam of formula XXIV is coupled to bromide XXV (where P2 is a protecting group for an OH or NH group) using a base such as for example, $Cs_2CO_3$), a palladium reagent such as. $Pd_2\,dba_3$, and a phosphine ligand such as Xantphos™ in a non-protic solvent (ex. dioxane, toluene, benzene etc.). The reaction is performed at a temperature range of about RT to reflux from about 3 to 24 h and is then isolated by aqueous work-up and purified by means known in the art.

As shown in step 23, the protecting group of XXVII is removed using conditions consistent with the type of protecting group that is used. For example, a silyl ether is removed using a $Bu_4NF$. In addition, a p-toluene sulfonate ester is removed under basic conditions using for example, LiOH in 2:1 dioxane water, to afford a compound of formula XI.

In step 24, alkylation of the free NH or OH group of XII is achieved using conditions previously described in step 8 to afford a compound of formula XIII.

Scheme 7. Synthesis of lactam compounds of formula XIII (Route 3).

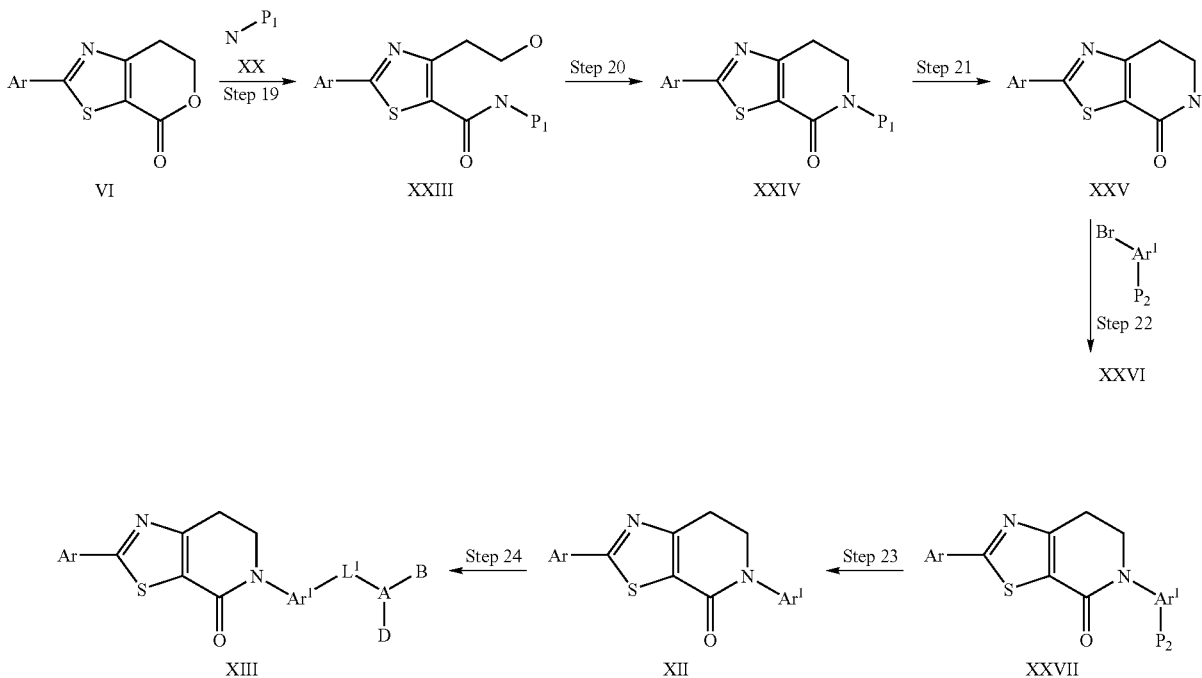

Scheme 8 shows the preferred synthesis of substituted morpholines that are used as reagents in the synthesis of compounds of the invention.

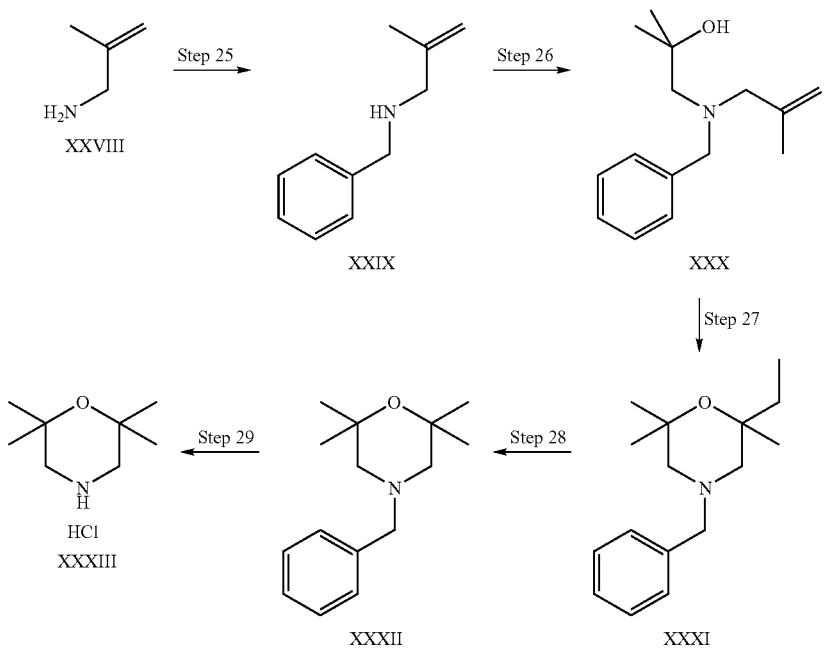

Scheme 8. Synthesis of substituted morpholine analogs.

In step 25, the amino group of methallyl amine (XXVII) is protected with a benzyl group via a reductive amination. Amine XXVIII is dissolved in a polar aprotic solvent like and treated with benzaldehyde. The imine intermediate is then reduced with a reducing reagent like $NaBH_4$ for 10-24 hours at a temperature range of room temperature to 50° C. to give an amine of formula XXIX that is isolated by aqueous work-up and purified by means known in the art.

In step 26, an amine of formula XXIX is alkylated by treating with an epoxide (for example, isobutylene oxide) and Lewis acid such as LiBr at a temperature range from room temperature to 60° C. for 1 to 8 hours to give alcohol of formula XXX. The product is isolated by aqueous work-up and purified by means known in the art.

In step 27, the preferred method for forming the substituted morpholine is via halo-etherification methodology. In this approach, an alcohol of formula XXX is treated with iodine. The reaction is performed in a biphasic mixture of a nonpolar aprotic solvent, such as MTBE, and an aqueous basic solution (for example, 1M $NaHCO_3$) for 12 to 24 h. The iodide of formula XXXI is then isolated by aqueous work-up and purified by means known in the art.

In step 28, the iodide is removed under reducing conditions to give the benzyl morpholine of formula XXXII. Typical conditions to remove an alkyl iodide group are to dissolve the iodide XXXI in a polar solvent such as DMSO and treat with a reducing reagent like $NaBH_4$ for 2 to 6 hours. Morpholine of formula XXXII is isolated by aqueous work-up and purified by means known in the art.

In step 29, the benzyl protecting group is removed under typical reductive conditions that are recognized by persons skilled in the art. For example, compound of formula XXXII is dissolved in suitable solvent (example THF, ETOH), treated with 3% palladium on activated carbon under hydrogen atmosphere that is pressurized up to 60 psi at 40° C. for up to 24 h. Morpholine of formula XXXIII is purified by means known in the art and can be isolated as the hydrochloride salt by treating with an HCl source (ex. 1.0M HCl in ether).

Demonstration of Function

In order to demonstrate that compounds of the present invention have the capacity to bind to and inhibit the function of MCHR1, binding and functional assays were established. All ligands, radioligands, solvents and reagents employed in these assays are readily available from commercial sources or can be readily prepared by those skilled in the art.

The full-length cDNA for human MCHR1 was cloned from a human adult brain cDNA library (Edge Biosystems, Cat. 38356) by standard polymerase chain reaction (PCR) methodology employing the following primers: sense, 5'-GCCACCATGGACCT GGAAGCCTCGCTGC-3'; antisense, 5'-TGGTGCCCTGACTTGGAGGTGTGC-3'. The PCR reaction was performed in a final volume of 50 µl containing 5 µl of a 10× stock solution of PCR buffer, 1 µl of 10 mM dNTP mixture (200 µM final), 2 µl of 50 mM $Mg(SO_4)$ (2 mM final), 0.5 µl of 20 µM solutions of each primer (0.2 µM final), 5 µl of template cDNA containing 0.5 ng DNA, 0.5 µl of Platinum Taq High Fidelity DNA polymerase (Gibco Life Technologies) and 36 µl of $H_2O$. PCR amplification was performed on a Perkin Elmer 9600 thermocycler. After denaturation for 90 sec at 94° C., the amplification sequence consisting of 94° C. for 25 sec, 55° C. for 25 sec and 72° C. for 2 min was repeated 30 times, followed by a final elongation step at 72° C. for 10 min. The desired PCR product (1.1 Kb) was confirmed by agarose gel electrophoresis and the band was extracted from the gel by Geneclean (Bio101) following the manufacturer's instructions. Following extraction, the cDNA fragment was cloned into pCR2.1-TOPO plasmid (Invitrogen Corp) to confirm the identity and sequence.

In order to generate cell lines stably expressing MCHR1, the insert was then subcloned into the Xba I and Not I sites of pcDNA(+)-3.1-neomycin (Invitrogen). After purification by Qiagen Maxi-prep kit (QIAGEN, Inc.), the plasmid was transfected by Fugene 6 (Roche Applied Science) into AV12 cells that had been previously transfected with the promiscuous G protein $G_{\alpha 15}$. The transfected cells were selected by G418 (800 μg/ml) for 10-14 days and single colonies were isolated from culture plates. The G418-resistant colonies were further selected for MCHR1 expression by measuring MCH-stimulated $Ca^{2+}$ transients with a fluorometric imaging plate reader (FLIPR, Molecular Devices).

Typically, individual clones are plated out in 96-well plates at 60,000 cells per well in 100 μl of growth medium (Dulbecco's modified Eagle's medium (DMEM), 5% fetal bovine serum, 2 mM L-glutamine, 10 mM HEPES, 1 mM sodium pyruvate, 0.5 mg/ml Zeocin, and 0.5 mg/ml Geneticin). After 24 hrs at 37° C., medium is removed and replaced with 50 μl of dye loading buffer (Hank's balanced salt solution (HBSS) containing 25 mM HEPES, 0.04% Pluronate 127 and 8 μM Fluo3 Both from Molecular Probes)). After a 60 min loading period at room temperature, dye loading buffer is aspirated and replaced with 100 μl of HEPES/HBBS. Plate is placed in FLIPR and basal readings are taken for 10 sec, at which point 100 μl of buffer containing 2 μM MCH (1 μM final) is added and measurements are taken over 105 sec. To correct for variations between clones in numbers of cells per well, the MCH response is normalized to the response induced by epinephrine.

Both the $^{125}$I-MCH binding and functional GTPγ$^{35}$S binding assays employed membranes isolated from a clone designated as clone 43. Typically, cells from 20 confluent T225 flasks were processed by washing the monolayers in cold phosphate-buffered saline (PBS), scraping the cells into same and re-suspending the cell pellet in 35 ml of 250 mM Sucrose, 50 mM HEPES, pH 7.5, 1 mM $MgCl_2$, 24 μg/ml DNase I, and protease inhibitors (1 Complete® tablet, per 50 ml of buffer prepared, Roche Diagnostics). Alternatively, greater levels of cells could be generated by adapting cell growth to suspension culture in 20 L stirred vessel bioreactors. After incubation on ice for 5 min, cells were disrupted with 20-25 strokes of a Teflon/Glass homogenizer attached to an overhead motorized stirrer, and the homogenate was centrifuged at 40,000 rpm in Beckman Type 70.1 Ti rotor. The pellets were re-suspended in 250 mM Sucrose, 50 mM HEPES, pH 7.5, 1.5 mM $CaCl_2$, 1 mM $MgSO_4$ and protease inhibitors by Teflon/Glass homogenization to achieve a protein concentration of ~3-5 mg/ml (Pierce BCA assay with Bovine serum albumin as standard). Aliquots were stored at −70° C.

Binding of compounds to MCHR1 was assessed in a competitive binding assay employing $^{125}$I-MCH, compound and clone 43 membranes. Briefly, assays are carried out in 96-well Costar 3632 white opaque plates in a total volume of 200 μl containing 25 mM HEPES, pH 7.0, 10 mM $CaCl_2$, 2 mg/ml bovine serum albumin, 0.5% dimethyl sulfoxide (DMSO), 5 μg of clone 43 membranes, 200 pM $^{125}$I-MCH (NEN), 0.625 mg/ml of wheat germ agglutinin scintillation proximity assay beads (WGA-SPA beads, Amersham Inc., now GE Healthcare) and a graded dose of test compound. Non-specific binding is assessed in the presence of 0.1 μM unlabeled MCH. Bound $^{125}$I-MCH is determined by placing sealed plates in a Microbeta Trilux (Perkin Elmer Life and Analytical Sciences Inc.) and counting after a 12 hr delay.

$IC_{50}$ values (defined as the concentration of test compound required to reduce specific binding of $^{125}$I-MCH by 50%) are determined by fitting the concentration-response data to a 4-parameter model (max response, min response, Hill coefficient, $IC_{50}$) using Excel® (Microsoft Corp.). $K_i$ values are calculated from $IC_{50}$ values using the Cheng-Prusoff approximation as described by Cheng et al. (Relationship between the inhibition constant ($K_i$) and the concentration of inhibitor which causes 50% inhibition ($IC_{50}$) of an enzymatic reaction, *Biochem. Pharmacol.*, 22: 3099-3108 (1973)). The $K_d$ for $^{125}$I-MCH is determined independently from a saturation binding isotherm. Exemplified compounds showed a Ki of <1 μM under the binding assay conditions. Specifically, a sample of observed Ki values is provided in Table 1 (below) for demonstration purposes only.

TABLE 1

| Example # | Average MCHR1 Ki (nM) |
|---|---|
| 2 | 39.7 |
| 5 | 10.2 |
| 15 | 19.0 |
| 33 | 5.13 |
| 47 | 3.16 |
| 65 | 35.8 |

Functional antagonism of MCH activity is assesses by measuring the ability of test compound to inhibit MCH-stimulated binding of GTPγ$^{35}$S to clone 43 membranes. Briefly, assays are carried out in Costar 3632 white opaque plates in a total volume of 200 μl containing 50 mM Hepes, pH 7.4, 5 mM $MgCl_2$, 10 μg/ml saponin, 1.0 mg/ml bovine serum albumin, 100 mM NaCl, 3 μM GDP, 0.3 nM GTPγ$^{35}$S, 10 nM MCH (approximately equal to $EC_{90}$), 20 μg of clone 43 membranes, 5.0 mg/ml of wheat germ agglutinin scintillation proximity assay beads (WGA-SPA beads, Amersham Inc., now GE Healthcare) and a graded dose of test compound. The plates are sealed and left for 16-18 hrs at 4° C. After a 1 hr delay to allow plates to equilibrate to ambient temperature, bound GTPγ$^{35}$S is determined by counting in a Microbeta Trilux (Perkin Elmer Life and Analytical Sciences Inc).

$IC_{50}$ values (defined as the concentration of test compound required to reduce MCH-stimulated GTPγ$^{35}$S binding by 50%) are determined by fitting the concentration-response data to a 4-parameter model (max response, min response, Hill coefficient, $IC_{50}$) using Excel (Microsoft). After verifying competitive antagonism by Schild analysis, $K_b$ values are calculated from the $IC_{50}$ values for each antagonist and the $EC_{50}$ for MCH (determined independently) using a modification of the Cheng-Prusoff approximation as described by Leff and Dougal (*Trends Pharmacol. Sci.* (1993) 14: 110-112).

Exemplified compounds showed $IC_{50}$ values of <1 μM under the functional assay conditions disclosed herein.

In order to demonstrate in vivo efficacy, compounds of the invention were administered by oral gavage to diet-induced obese male Long-Evans rats (Harlan, Ind.) weighing 500-550 g. Vehicle consisted of 1% CMC and 0.25% PS-80 in water.

Animals were individually housed in a temperature regulated room (24° C.) with a reverse 12 hour light/dark cycle (dark 10:00/22:00). Water and food (Teklad 95217, Harlan, Wis.) were available ad libitum. Compounds were dosed orally once a day before onset of dark for 3 days. Daily food intake and body weight change were measured for the 3 day period. Exemplified compounds tested at 10 mg/kg showed reduction of 3 day cumulative body weight gain when compared with vehicle-treated controls. Specifically, a sample of observed 3 day cumulative body weight reduction, relative to control, is provided in Table 2 (below) for demonstration purposes only.

TABLE 2

| Example # | Body weight reduction @ 10 mg/Kg versus vehicle control. Data expressed in grams. |
|---|---|
| 42 | 1.7 |
| 47 | 7.2 |
| 52 | 9.6 |

Utility

As antagonists of the MCHR1 binding, a compound of the present invention is useful in treating conditions in human and non-human (especially companion) animals in which the MCHR1 receptor has been demonstrated to play a role. The diseases, disorders or conditions for which compounds of the present invention are useful in treating or preventing include, but are not limited to, diabetes mellitus, hyperglycemia, obesity, hyperlipidemia, hypertriglyceridemia, hypercholesterolemia, atherosclerosis of coronary, cerebrovascular and peripheral arteries, gastrointestinal disorders including peptic ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, neurogenic inflammation of airways, including cough, asthma, depression, prostate diseases such as benign prostate hyperplasia, irritable bowel syndrome and other disorders needing decreased gut motility, diabetic retinopathy, neuropathic bladder dysfunction, elevated intraocular pressure and glaucoma and non-specific diarrhea dumping syndrome. The diseases, disorders or conditions for which compounds of the present invention are useful in treating or preventing also include, stress related disorders including post traumatic stress disorder, substance abuse, including alcohol and drug abuse, and nonpharamcologic disorders such as gambling, sex and internet related addictions. By inhibiting MCH activity the compounds of the present invention provide anorexic effects. That is, the compounds of the invention are useful as appetite suppressants and/or weight loss agents. The compounds of the invention may also be used in combination with other approved therapeutic agents for the treatment, prevention and/or amelioration of obesity and related diseases. In this format, the compounds of the present invention enhance the positive effects of such approved combination treatments while minimizing the side effects due to the potential requirement of lower doses of such combination compounds. Such combination therapies may be delivered individually or in a combined formulation. Examples of compounds useful in combination with a compound of formula I include weight loss agents (Meridia™, Xenical™), cholesterol lowering agents (such as for example lovastatin, simvastatin pravastatin, fluvastatin, and atorvastatin), glucose level control or modulating agents, nerve growth factor agonists (such as for example, axokine), cannabinoid CB-1 antagonist compounds (such as for example rimonanbant) and the like.

In treating non-human, non-companion animals, the compounds of the present invention are useful for reducing weight gain and/or improving the feed utilization efficiency and/or increasing lean body mass.

Formulation

The compound of formula I is preferably formulated in a unit dosage form prior to administration. Therefore, yet another embodiment of the present invention is a pharmaceutical formulation comprising a compound of formula I and a pharmaceutical carrier.

The present pharmaceutical formulations are prepared by known procedures using well-known and readily available ingredients. In making the formulations of the present invention, the active ingredient (formula I compound) will usually be mixed with a carrier, or diluted by a carrier, or enclosed within a carrier which may be in the form of a liquid, tablet, capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders. One of skill in the art is aware of methods, reagents and conditions for preparing various standard formulations or can assess such information without undue experimentation. The compositions of the invention may be formulated so as to provide quick, sustained or delayed release of the active ingredient after administration to the patient.

Dose

The specific dose administered is determined by the particular circumstances surrounding each situation. These circumstances include, the route of administration, the prior medical history of the patient, the pathological condition or symptom being treated, the severity of the condition/symptom being treated, and the age and sex of the recipient. However, it will be understood that the therapeutic dosage administered will be determined by the physician in the light of the relevant circumstances, or by the veterinarian for non-human recipients.

Generally, an effective minimum daily dose of a compound of formula I is about 20 to 200 mg. Typically, an effective maximum dose is about 200 to 1000 mg. The exact dose may be determined, in accordance with the standard practice in the medical arts of "dose titrating" the recipient; that is, initially administering a low dose of the compound, and gradually increasing the dose until the desired therapeutic effect is observed.

Route of Administration

The compounds may be administered by a variety of routes including the oral, rectal, transdermal, subcutaneous, topical, intravenous, intramuscular or intranasal routes. Ap referred route of administration is oral.

Combination Therapy

A compound of formula I may be used in combination with other drugs or therapies that have been approved for the treatment/prevention/suppression or amelioration of the diseases or conditions for which compounds of formula I are useful. Such other drug(s) may be administered, by a route and in an amount commonly used therefor, contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those that also contain one or more other active ingredients, in addition to a compound of formula I. Examples of other active ingredients that may be combined (upon approval) with a compound of formula I, and either administered separately or in the same pharmaceutical composition, include, but are not limited to:

(a) insulin sensitizers including (i) PPARγ agonists such as the glitazones (e.g. troglitazone, pioglitazone, englitazone, MCC-555, BRL9653 and the like), and compounds disclosed in WO97/27857, 97/28115, 97/28137 and 97/27847; (ii) biguanides such as metformin;

(b) insulin or insulin mimetics;

(c) sulfonylureas such as tolbutamide and glipizide;

(d) alpha-glucosidase inhibitors (such as acarbose);

(e) cholesterol lowering agents such as
   i. HMG-CoA reductase inhibitors (lovastatin, simvastatin pravastatin, fluvastatin, atorvastatin, and other statins),
   ii. sequestrants (cholestyramine, colestipol and a dialkylaminoalkyl derivatives of a cross-linked dextran),
   iii. nicotinyl alcohol nicotinic acid or a salt thereof,
   iv. proliferator-activator receptor a agonists such as fenofibric acid derivatives (gemfibrozil, clofibrat, fenofibrate and benzafibrate),
   v. inhibitors of cholesterol absorption for example β-sitosterol and (acyl CoA:cholesterol acyltransferase) inhibitors for example melinamide,
   vi. probucol,
   vii. vitamin E, and
   viii. thyromimetics;

(f) PPARδ agonists such as those disclosed in WO97/28149;

(g) Anti obesity compounds such as fenfluramine, dexfenfluramine, phentermine, sibutramine, orlistat, axokine, rimonanbant, etc;

(h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(i) PPARα agonists such as described in WO 97/36579 by Glaxo;

(j) PPARγ antagonists as described in WO97/10813; and (k) serotonin reuptake inhibitors such as fluoxetine and sertraline (l) antipsychotic agents such as for example olanzapine.

EXAMPLES

The following examples are only illustrative of the preparation protocols and Applicants' ability to prepare compounds of the present invention based on the schemes presented or modifications thereof. The examples are not intended to be exclusive or exhaustive of compounds made or obtainable.

Materials and Method

Solvents and reagents were used as purchased from chemical suppliers and reactions were conducted at ambient atmosphere unless otherwise stated. Mass spectrum data was obtained on a Micromass Platform LCZ spectrometer using electrospray (ES) ionization. NMR data was obtained on a Varian 400 MHz spectrometer and is reported in ppm. A CEM Discover microwave reactor was used where indicated. Common abbreviations used throughout the experimentals are: methanol (MeOH), ethanol (EtOH), ethyl acetate (EtOAc), dichloromethane ($CH_2Cl_2$), dimethylformamide (DMF), tetrahydrofuran (THF), and room temperature (RT).

Preparation 1

Triisopropyl-(2-methoxy-4-nitro-phenoxy)-silane

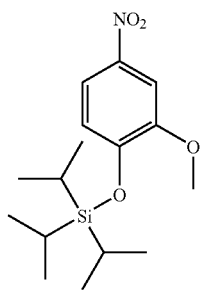

Dissolve 4-nitroguiacol (50.0 g, 295.6 mmol) in DMF (anhydrous, 1000 mL) and cool the solution to 0-5° C. then slowly treat with NaH (60% in mineral oil, 13.4 g, 335.0 mmol) keeping the temp. <10° C. Stir the yellow-orange solution mechanically at room temp. for ca. 30 min. then cool to 0-5° C. Treat the mixture with TIPS triflate (90.0 mL, 334.8 mmol), keeping the temp. <10° C., then stir at room temp. overnight. Quench the mixture with 14% aqueous $NH_4Cl$ (1000 mL) then extract with EtOAc (3×1000 mL). Combine the organic solutions, wash with brine (1000 mL), and concentrate in vacuo to give a light yellow oil that was purified by flash chromatography, using 100% hexanes then 10% EtOAc/hexanes, to give the title compound as a yellow oil (95.8 g, 99.6% yield). MS (ES+) 326.2 (M+1)+.

Preparation 2

3-Methoxy-4-triisopropylsilanyloxy-Phenylamine

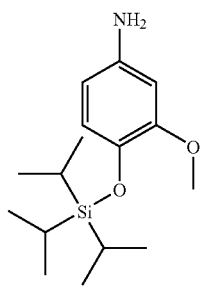

Dissolve triisopropyl-(2-methoxy-4-nitro-phenoxy)-silane (95.7 g, 294.0 mmol) in EtOH (1800 mL) and add 5% Pd/C (10.0 g). Hydrogenate the slurry at room temperature under 50 psi hydrogen for 8 h. Filter the slurry through a pad of Celite® and rinse with EtOH. Concentrate the filtrate in vacuo to give a brown oil. Purify by flash chromatography, using a gradient from 100% hexanes to 20% EtOAc/hexanes, to give the title compound as a brown solid (67.4 g, 77.6% yield). MS (ES+) 296.2 (M+1)+.

Preparation 3

[2-(4-chloro-phenyl)-thiazol-4-yl]-acetic acid ethyl ester

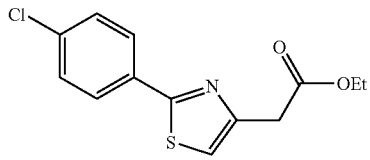

Dissolve 4-chlorothiobenzamide (74.0 g, 431.1 mmol) in absolute EtOH (470 ml, absolute). Add ethyl-4-chloroacetoacetate (58.0 ml, 70.1 g, 426.0 mmol) to the solution. stir mechanically at reflux for 2 h. Allow the reaction to cool to room temperature and dilute with water (1000 ml). Extract the mixture with Et$_2$O (2000 ml, then 2×500 ml). Combine the organic layers and wash with brine (950 ml). Concentrate the organic layer in vacuo to give an oil weighing 121.8 g. The oil solidifies on standing.

Suspend the solid in isopropyl alcohol (610 ml) and heat the slurry to 35° C. at which temperature all the solids dissolve. Charge the solution with water (1830 mL) and allow to cool to room temperature. At approximately 32° C., precipitation occurs. Stir the resulting slurry mechanically at room temperature for 4.5 h and filter. Dry the solid in a vacuum oven at 35° C. for 2 days to give a solid weighing 107.3 g (89.4% yield). MS (ES+) 282.1 (M)$^+$.

Preparation 4

[2-(4-Methoxy-phenyl)-thiazol-4-yl]-acetic acid ethyl ester

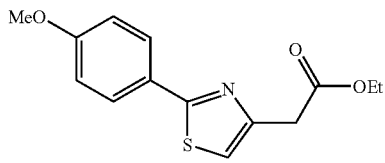

Prepare the title compound by essentially following the procedure as described in Preparation 7, using 4-methoxythiobenzamide. MS (ES+) 278.2 (M+1)$^+$. $^1$H NMR (400 MHz, CDCl$_3$): δ 7.82 (d, J=8.8 Hz, 2H), 7.11 (s, 1H), 6.93 (d, J=8.8 Hz, 2H), 4.21 (q, J=7.0 Hz, 2H), 3.87 (s, 2H), 3.85 (s, 3H), 1.29 (t, J=7.0 Hz, 3H).

Preparation 5

2-[2-(4-chloro-phenyl)-thiazol-4-yl]-ethanol

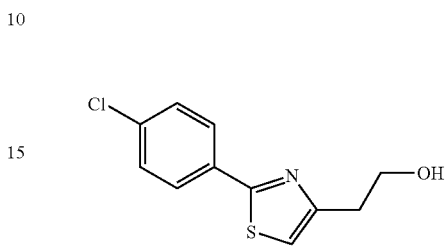

Dissolve [2-(4-chloro-phenyl)-thiazol-4-yl]-acetic acid ethyl ester (107.4 g, 381.2 mmol) in THF (800 mL) and cool to 0-5° C. Add DIBAL (1.0 M in THF, 800 mL, 800 mmol) slowly over approximately 3.5 h (somewhat exothermic) keeping the temp. <5° C. Allow the reaction to warm to room temperature with mechanical stirring overnight. Cool the reaction to 0-5° C. and slowly add more DIBAL (150 mL) over approximately 15 min keeping the temperature <5° C. Stir the reaction solution at room temperature for 2.5 b. Cool to 0-5° C. and slowly add over 5 h aqueous saturated Rochelle's salt (2900 mL, very exothermic at first, minor gas evolution) keeping the temperature <10° C. The mixture solidifies after approximately 150 mL has been added. It becomes more fluid and then solidifies again as the addition continues. Extract the mixture with EtOAc (2×3300 mL). Combine the organic layers and concentrate in vacuo to give an oil weighing 112.9 g. Take the oil up in toluene (600 mL), concentrate in vacuo and repeat. Dry the residue on a vacuum pump for 6 h to give a residue weighing 107.4 g (110% yield). MS (ES+) 240.1 (M)$^+$. 1H NMR (400 MHz, CDCl$_3$): δ 7.84 (dt, J=8.4, 2.2 Hz, 2H), 7.39 (dt, J=8.4, 2.2 Hz, 2H), 6.98 (s, 1H), 3.98 (m, 2H), 3.44 (bs, 1H), 3.02 (t, J=5.5 Hz, 2H).

Preparation 6

2-[2-(4-Methoxy-phenyl)-thiazol-4-yl]-ethanol

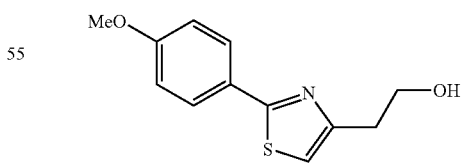

Prepare the title compound by essentially following the procedure as described in Preparation 5, using [2-(4-methoxy-phenyl)-thiazol-4-yl]-acetic acid ethyl ester. MS (ES+) 236.2 (M+1)$^+$. $^1$H NMR (400 MHz, CDCl$_3$): δ 7.88 (d, J=8.8 Hz, 2H), 6.95 (d, J=8.8 Hz, 2H), 6.91 (s, 1H), 3.98 (t, J=5.3 Hz, 2H), 3.85 (s, 3H), 3.03 (t, J=5.3 Hz, 2H).

Preparation 7

2-(4-chloro-phenyl)-4-(2-hydroxy-ethyl)-thiazole-5-carboxylic acid

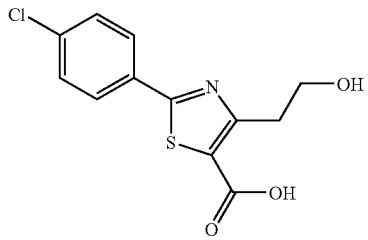

Suspend 2-[2-(4-chloro-phenyl)-thiazol-4-yl]-ethanol (107 g gross, 91 g net, 380 mmol) in THF (1210 mL). Decant the solution from the undissolved solids. Cool the THF solution to −75° C. Evacuate under vacuum and purge with nitrogen three times. Add n-butyl lithium (1.6 M in hexanes, 530 mL, 848 mmol) slowly over 4 h keeping the temp. <−70° C. Then add the cold solution (at −75° C.) slowly via cannulae over 3.5 h to a flask containing THF at −75° C. that has been saturated with $CO_2$ gas (approximately 390 g) keeping the temp. <−60° C. (addition is very exothermic). Charge the resulting brown slurry with additional $CO_2$ gas (approximately 355 g). Allowed the reaction to come to room temperature while stirring mechanically at room temperature overnight.

Add 1N HCl (2100 mL+900 mL), cool the slurry to 16° C. and filter. Rinse the resulting solid with hexane (1400 mL) and dry on the filter funnel with vacuum and a stream of nitrogen to give a solid weighing 81.3 g (75.4% yield). MS (ES+) 284.0 (M+1)$^+$. $^1$H NMR (400 MHz, DMSO-d6): δ 7.96 (dt, J=8.8, 2.2 Hz, 2H), 7.55 (dt, J=8.4, 2.2 Hz, 2H), 3.74 (t, J=7.0 Hz, 2H), 3.35 (s, 1H), 3.26 (t, J=7.0 Hz, 2H).

Preparation 8

4-(2-Hydroxy-ethyl)-2-(4-methoxy-phenyl)-thiazole-5-carboxylic acid

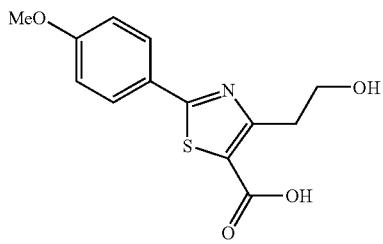

Prepare the titled compound by essential following the procedure as described in Preparation 7, using 2-[2-(4-methoxy-phenyl)-thiazol-4-yl]-ethanol. MS (ES+) 280.2 (M+1)$^+$. $^1$H NMR (400 MHz, CD$_3$OD): δ 7.92 (d, J=8.8 Hz, 2H), 7.02 (d, J=8.8 Hz, 2H), 3.92 (t, J=7.0 Hz, 2H), 3.86 (s, 3H), 3.38 (t, J=7.0 Hz, 2H).

Preparation 9

2-(4-Chloro-phenyl)-4-(2-methoxy-ethyl)-thiazole-5-carboxylic acid methyl ester

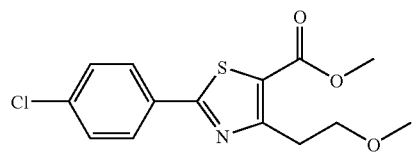

Add a 1.0 M solution of sufuryl chloride in dichloromethane (20.0 mL, 20.0 mmol) dropwise to a solution of 5-methoxy-3-oxo-pentanoic acid methyl ester (3.0 g, 18.8 mmol) in dichloromethane (20.0 mL) at 0° C. and stir under nitrogen at 0° C. for 2 h. Concentrate the reaction mixture on a rotavap (rotary evaporator), keeping the bath temperature at RT. Add 4-chlorothiobenz-amide (3.67 g, 21.5 mmol) to the residue, followed by methanol (30.0 mL) and heat to 60° C. for 18 h. Quench the reaction with water and extract with EtOAc (2×). Combine the organic portions, wash with brine, dry over MgSO$_4$, filter, and concentrate under vacuum. Purify by flash chromatography on silica gel, using a gradient of EtOAc/Hexane (0-60%) to give the title compound (3.3 g, 57%). Exact mass=311.0, MS (ES+) 312.0 (M+1). $^1$H NMR (CDCl$_3$): δ 7.89 (d, 2H, J=8.8 Hz), 7.40 (d, 2H, J=8.8 Hz), 3.88 (s, 3H), 3.82 (t, 2H, J=6.8 Hz), 3.47 (t, 2H, J=6.8 Hz), 3.38 (s, 3H).

Prepare the compounds below, Preparations 9b to 9f, by essentially following the procedure as described in Preparation 13, using the appropriate thiobenzamide as starting material.

| Prep | Product (Chemical Name) | Structure | MS (ES+) or NMR |
|---|---|---|---|
| 9b | 4-(2-Methoxy-ethyl)-2-phenyl-thiazole-5-carboxylic acid methyl ester | 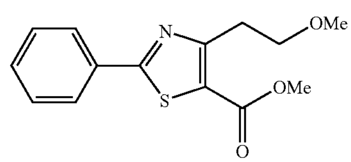 | 278.2 (M + 1)$^+$. |

| Prep | Product (Chemical Name) | Structure | MS (ES+) or NMR |
|---|---|---|---|
| 9c | 2-(3-Chloro-phenyl)-4-(2-methoxy-ethyl)-thiazole-5-carboxylic acid methyl ester | 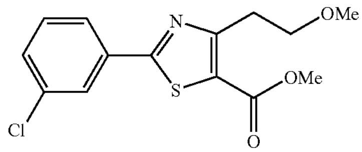 | 312.3 (M + 1)$^+$ |
| 9d | 4-(2-Methoxy-ethyl)-2-(4-trifluoromethyl-phenyl)-thiazole-5-carboxylic acid methyl ester | 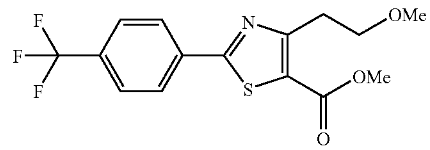 | 346.3 (M + 1)$^+$ |
| 9e | 2-(2,4-Dichloro-phenyl)-4-(2-methoxy-ethyl)-thiazole-5-carboxylic acid methyl ester | 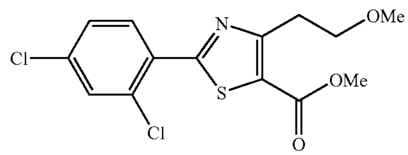 | $^1$H NMR (400 MHz, CDCl$_3$) δ: 8.34 (d, 1H, J = 7.3 Hz), 7.52 (d, 1H, J = 2.0 Hz), 7.36 (dd, 1H, J = 2.0, 9.0 Hz), 3.90 (s, 3H), 3.83 (t, 2H, J = 6.9 Hz), 3.49 (t, 2H, J = 6.9 Hz). |
| 9f | 2-(4-Fluoro-phenyl)-4-(2-methoxy-ethyl)-thiazole-5-carboxylic acid methyl ester | 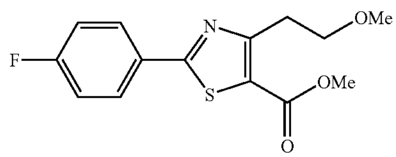 | 296.3 (M + 1)$^+$ |

Preparation 10

5-Acetoxy-3-oxo-pentanoic acid ethyl ester

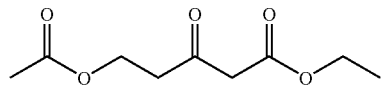

In a 2 L round bottom flask with stir bar, dissolve acetic acid 3-buten-1-yl ester (50 g, 438.1 mmol) in 1.5 L of dichloromethane and cool to −78° C. Vigorously bubble ozone through the reaction solution for about 2 h at which time the solution becomes very deeply colored (blue/purple). Bubble ozone through for an additional 5 min. Discontinue the ozone and bubble in oxygen until the color fades completely (about 15 min). To the reaction, which is maintained at a temperature of −78° C., add dimethyl sulfide (83.8 g, 99.0 mL, 1.35 mole). Allow to warm to ambient temperature overnight. Concentrate the reaction in vacuo to provide acetic acid 3-oxo-propyl ester. Use the material as is, with no further purification or characterization.

Charge a round-bottom flask with tin(II) chloride (16.6 g, 0.088 mol), purge with nitrogen, and add dichloroethane (300 mL) by cannula. Add ethyl diazoacetate (92 mL, 0.88 mol) by cannula and stir 10 min. Add a solution of acetic acid 3-oxo-propyl ester (0.44 mol) in CH$_2$Cl$_2$ (600 mL) slowly by cannula over 1 h, then stir the reaction in a 50° C. oil bath for 3 h. Concentrate under vacuum, add saturated aqueous NaHCO$_3$ and remove the organic phase. Extract the aqueous portion with EtOAc (2×). Wash the combined organic portions with brine, dry over MgSO$_4$, filter through Celite®, and concentrate under vacuum. Purify by flash chromatography on silica gel, eluting with a gradient of EtOAc/hexane 8%-25% to give the title compound (27.8 g, 31%), exact mass 202.08, mass spectrum (ES) 225.1 (M+Na). $^1$H NMR (CDCl$_3$): δ 4.34 (t, J=6.1 Hz, 2H), 4.20 (q, J=7.1 Hz, 2H), 3.46 (s, 2H), 2.89 (t, J=6.1 Hz, 2H), 2.03 (s, 3H), 1.28 (t, J=7.1 Hz, 3H).

Preparation 11

5-Acetoxy-2-bromo-3-oxo-pentanoic acid ethyl ester

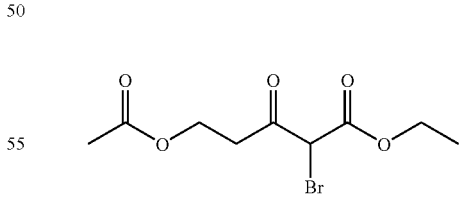

Purge a round-bottom flask containing 5-acetoxy-3-oxo-pentanoic acid ethyl ester (11.3 g, 55.9 mmol) with nitrogen, add acetonitrile (250 mL) by cannula and chill in an ice water bath. Add copper(II) bromide (13.1 g, 58.7 mmol) neat and stir 5 min under nitrogen. Add [hydroxy(tosyloxy)iodo]benzene (23.0 g, 58.7 mmol) neat, stir 5 min and quench with water. Extract with ether (3×), wash combined organics with brine, dry over MgSO$_4$, filter and concentrate under vacuum. Purify by flash chromatography on silica gel, using a gradient of EtOAc/hexane (8%-30%) to give the title compound (6.56 g, 42%). $^1$H NMR (CDCl$_3$): δ 4.78 (s, 1H), 4.35 (t, J=6.2 Hz, 2H), 4.29 (q, J=7.1 Hz, 2H), 3.12 (q, J=5.7 Hz, 2H), 2.04 (s, 3H), 1.32 (t, J=7.1 Hz, 3H).

Preparation 12

2-(4-Chloro-phenyl)-6,7-dihydro-pyrano[4,3-d]thiazol-4-one

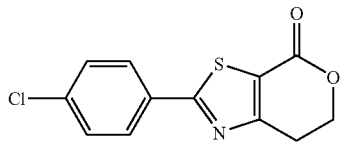

Method 1: Purge a round-bottom flask containing 4-chloro-thiobenzamide (5.23 g, 18.6 mmol), with nitrogen, and add acetonitrile (50 mL) by syringe. Add a solution of 5-acetoxy-2-bromo-3-oxo-pentanoic acid ethyl ester (3.83 g, 22.3 mmol) in acetonitrile (15 mL) by syringe and stir at RT under nitrogen for 1 h. Concentrate under vacuum to a solid, dilute with toluene (100 mL), water (5 drops) and add p-toluenesulfonic acid monohydrate (7.08 g, 37.2 mmol) neat. Attach a fractional distillation apparatus with collection flask and set in 120° C. oil bath. After first distillate is collected at approximately 80° C. (monitored at head of distillation column) increase oil bath temperature in 5 degree increments to 140° C. until reaction has been concentrated to one-half volume. Remove from heat, neutralize with saturated aqueous NaHCO$_3$, extract with EtOAc (3×), dry over MgSO$_4$, filter and concentrate under vacuum. Purify by flash chromatography on silica gel, using a gradient of EtOAc in CH$_2$Cl$_2$ (0%-10%) to give the title compound (2.48 g, 48%). Exact mass=265.0, MS (ES+) 266.0 (M+1)$^+$. $^1$H NMR (CDCl$_3$): δ 7.93 (dt, J=8.4, 2.1 Hz, 2H), 7.46 (dt, J=8.4, 2.2 Hz, 2H), 4.67 (t, J=6.4 Hz, 2H), 3.23 (t, J=6.4 Hz, 2H).

Method 2: Add 1.0 M solution of boron tribromide in dichloromethane (21.0 mL, 21.0 mmol) dropwise to a solution of 2-(4-chloro-phenyl)-4-(2-methoxy-ethyl)-thiazole-5-carboxylic acid methyl ester (6.0 g, 19.3 mmol) in dichloromethane (60.0 mL) at −78° C. and stir under nitrogen at 0° C. for 3 h. Quench reaction mixture with ether (50.0 mL) and water (50.0 mL), stir for additional 30 min and concentrate. Dilute residue with water and extract EtOAc (2×). Combine EtOAc, wash with brine, dry over MgSO$_4$, filter, and concentrate under vacuum. Add p-TsOH (7.0 g, 36.8 mmol) and toluene (100.0 mL) to the residue, reflux at 110° C. for 18 h, and concentrate the reaction mixture. Add saturated NaHCO$_3$ solution and extract with EtOAc (2×). Combine EtOAc, wash with brine, dry over MgSO$_4$, filter, and concentrate under vacuum. Purify by flash chromatography on silica gel, using a gradient of MeOH/dichloromethane (0-5%) to give the title compound (1.5 g, 29%).

Method 3: Combine 2-(4-chloro-phenyl)-4-(2-hydroxyethyl)-thiazole-5-carboxylic acid (81.2 g, 286.2 mmol) with p-TsOH monohydrate (32.0 g, 168.2 mmol) in toluene (1200 mL). Heat the resulting slurry to reflux, eventually reaching a temperature of approximately 112° C. Stir the resulting tan solution mechanically at reflux for 2 h while using a Dean-Stark trap to collect water. Allow the reaction to cool to room temperature and add saturated aqueous NaHCO$_3$ (1700 mL) and EtOAc (1700 mL). Separate the layers and extract the aqueous layer with EtOAc (2×1700 mL). Combine the organic layers, wash with brine (1700 mL) and concentrate in vacuo. Take up the resulting solid in CH$_2$Cl$_2$ (500 mL) and concentrate in vacuo, repeating with CH$_2$Cl$_2$ twice more to obtain 60.1 g (79.2% yield).

Prepare the compounds below, Preparations 12b to 12f, by essentially following the procedure as described in Preparation 12, Method 2, using the appropriate (2-methoxy-ethyl)-thiazole-5-carboxylic acid methyl ester as starting material.

| Prep | Product (Chemical Name) | Structure | MS (ES+) |
|---|---|---|---|
| 12b | 2-Phenyl-6,7-dihydro-pyrano[4,3-d]thiazol-4-one | 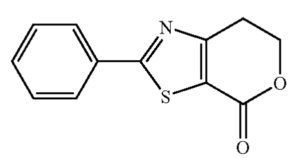 | 232.2 (M + 1)$^+$ |
| 12c | 2-(3-Chloro-phenyl)-6,7-dihydro-pyrano[4,3-d]thiazol-4-one | 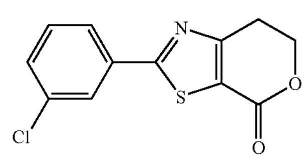 | 266.2 (M + 1)$^+$ |
| 12d | 2-(4-Trifluoromethyl-phenyl)-6,7-dihydro-pyrano[4,3-d]thiazol-4-one | 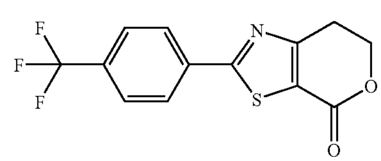 | 300.3 (M + 1)$^+$ |

| Prep | Product (Chemical Name) | Structure | MS (ES+) |
|---|---|---|---|
| 12e | 2-(2,4-Dichloro-phenyl)-6,7-dihydro-pyrano[4,3-d]thiazol-4-one | 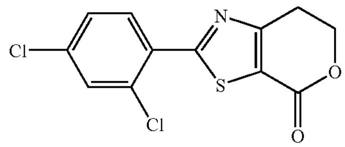 | 300.0 (M + 1)+ |
| 12f | 2-(4-Fluoro-phenyl)-6,7-dihydro-pyrano[4,3-d]thiazol-4-one | 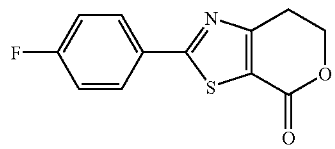 | 250.2 (M + 1)+ |

12g: 2-(4-Methoxy-phenyl)-6,7-dihydro-pyrano[4,3-d]thiazol-4-one

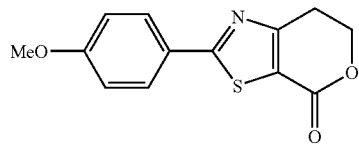

Prepare the title compound by essentially following the procedure of Example 12, Method 3, using 4-(2-hydroxy-ethyl)-2-(4-methoxy-phenyl)-thiazole-5-carboxylic acid. MS (ES+) 262.2 (M+1)+. $^1$H NMR (400 MHz, CDCl$_3$): δ 7.94 (d, J=9.2 Hz, 2H), 6.98 (d, J=9.2 Hz, 2H), 4.66 (t, J=6.2 Hz, 2H), 3.88 (s, 3H), 3.21 (t, J=6.2 Hz, 2H).

Preparation 13 tert-Butyl-(2-methoxy-4-nitro-phenoxy)-dimethyl-silane

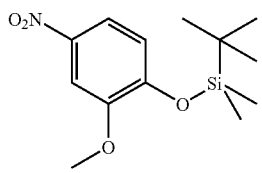

Add tert-butyl-dimethylsilylchloride (14 g, 90 mmol) to a solution of 4-nitroguaiacol (5 g, 30 mmol) in DMF (250 mL) and then add imidazole (6.13 g, 90 mmol). Stir the mixture at room temperature for 16 h. Quench the reaction mixture with water (150 mL). Extract with diethyl ether (3×200 mL). Wash the combined organic portions with water, brine, and dry over MgSO$_4$. Filter and concentrate to a residue. Purify the residue by silica gel flash chromatography, eluting with 15% ethylacetate:hexanes to give the title compound (8.053 g, 95%) as a pale yellow oil. MS (ES+) 284.1 (M+1)+. $^1$H NMR (CDCl$_3$): δ 7.79 (dd, J=7.8 Hz, 2.7 Hz, 1H), 7.26 (d, J=2.7 Hz, 1H), 6.69 (d, J=7.8 Hz 1H), 3.85 (s, 3H), 0.96 (s, 9H), 0.18 (s, 6H).

Preparation 14

1-(2,2-Dimethoxy-ethoxy)-4-nitro-benzene

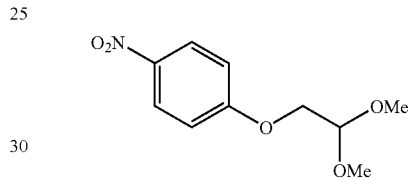

Dissolve glycolaldehyde dimethylacetal (5 g, 47.12 mmol) in dry DMF (100 mL) and cool to 0° C. Add portion-wise NaH (60% dispersion, 1.88 g, 47.12 mmol). Heat the reaction mixture to 100° C. overnight. Add water (200 mL) and extract with EtOAc (3×50 mL). Dry the organic layer with Na$_2$SO$_4$, filter, and concentrate. Purify by silica gel chromatography, eluting with 0-50% EtOAc in hexanes to give the title compound as a wet yellow solid (7.96 g, 74%). $^1$H NMR (CDCl$_3$): δ 8.23 (d, J=8.8 Hz, 2H), 7.02 (d, J=8.8 Hz, 2H), 4.77 (t, J=4.8 Hz, 1H), 4.12 (d, J=5.3 Hz, 2H), 3.50 (s, 6H).

Preparation 15

2,2-Dimethyl-propionic acid 2-methoxy-4-nitro-phenyl ester

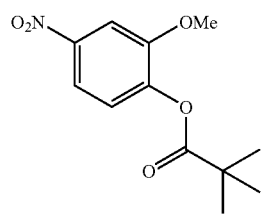

Dissolve trimethylacetyl chloride (3.64 mL, 29.56 mmol) in dry pyridine (100 mL). Add 4-nitroguaiacol (5.0 g, 29.56 mmol) followed by addition of DMAP (100 mg) and stir overnight. Remove the pyridine via reduced pressure and then add 1N HCl solution to give a white solid precipitate which is collected by vacuum filtration and washed with water to give the title compound as a white solid (7.4 g, 99%).

$^1$H NMR (CDCl$_3$): δ 7.87 (dd, J=8.8, 2.6 Hz, 1H), 7.82 (d, J=2.6 Hz, 1H), 7.15 (d, J=8.8 Hz, 1H), 3.91 (s, 3H), 1.37 (s, 9H).

Preparation 16

1-(2,2-Dimethoxy-ethoxy)-2-mehoxy-4-nitro-benzene

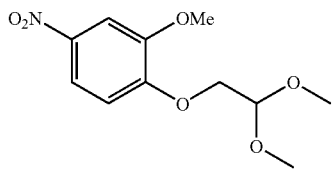

To an oven-dried round bottom flask, add 2-methoxy-4-nitro-phenol (2.45 g, 14.5 mmol) and purge with nitrogen. Add DMF (25 mL) by syringe, followed by K$_2$CO$_3$ (3.0 g, 21.7 mmol) and KI (catalytic) neat. Stir 30 min at room temperature and add 2-bromo-1,1-dimethoxy-ethane (1.9 mL, 15.9 mmol) by syringe. Attach a reflux condenser and stir overnight in a 120° C. oil bath. Quench with water, extract with ether (3×), dry over MgSO$_4$, filter and concentrate under vacuum. Add xylenes and concentrate again under vacuum. Purify by flash chromatography on silica gel using a gradient of EtOAc/hexane (20% to 60%) to give the title compound as a white residue (2.55 g, 68%). Exact mass=257.1, MS (ES+) 258.2 (M+1)$^+$. $^1$H NMR (CDCl$_3$): δ 7.88 (dd, J=9.1, 2.8 Hz, 1H), 7.74 (d, J=2.8 Hz, 1H), 6.94 (d, J=9.1 Hz, 1H), 4.77 (t, J=5.2 Hz, 1H), 4.13 (d, J=4.9 Hz, 2H), 3.93 (s, 3H), 3.48 (s, 6H).

Preparation 17

4-(2-Methoxy-4-nitro-phenyl)-morpholine

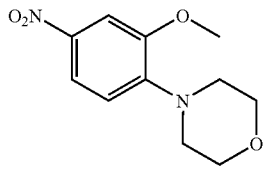

Mix morpholine (1.50 mL, 17.20 mmol) and 1-chloro-2-methoxy-4-nitro-benzene (1.06 g, 5.65 mmol) and heat to 100° C. for 4 h while stirring. Cool the solution to room temperature, then partition between EtOAc (40 mL) and 1N HCl (20 mL). Wash the organic solution with water (20 mL) and brine (20 mL), dry, filter, and concentrate. Purify the crude material by flash chromatography, using a linear gradient of 100% hexanes to 50% EtOAc/hexanes, to give the title compound as a yellow solid (250 mg, 18%). MS (ES+) 239.0 (M+1)$^+$. $^1$H NMR (400 MHz, CDCl$_3$) δ: 7.86 (dd, 1H, J=8.8, 2.6 Hz), 7.71 (d, 1H, J=2.2 Hz), 6.87 (d, 1H, J=9.2 Hz), 3.94 (s, 31), 3.87 (m, 4H), 3.21 (m, 4H).

Preparation 18

1-(2-Methoxy-4-nitro-phenyl)-piperidin-4-ol

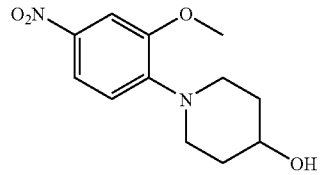

Prepare the title compound by essentially following the procedure as described for Preparation 17, using 4-hydroxypiperidine. MS (ES+) 253.0 (M+1)$^+$. $^1$H NMR (400 MHz, CDCl$_3$) δ 7.83 (dd, 1H, J=8.8, 2.6 Hz), 7.69 (d, 1H, J=2.6 Hz), 6.88 (d, 1H, J=9.2 Hz), 3.99 (s, 1H), 3.94 (s, 3H), 3.90 (m, 1H), 3.56-3.50 (m, 2H), 2.99-2.91 (m, 2H), 2.07-2.00 (m, 2H), 1.79-1.69 (m, 2H).

Preparation 19

1-Prop-2-ynyl-pyrrolidine

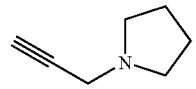

Add propargyl bromide (18.0 g, 120.0 mmol) dropwise at 0° C. to a solution of pyrrolidine (23.0 g, 323.0 mmol) in ether (50 mL). Stir for 18 h at room temperature and filter the reaction to remove the solids. Dilute the filtrate with water and extract with ether. Dry the ether with brine, then Na$_2$SO$_4$, and concentrate on a rotary evaporator at low temperature to give the title compound (10.0 g, 77%). MS (ES+) 110 (M+1)$^+$. $^1$H NMR (400 MHz, DMSO-d6): δ 3.33 (d, 2H, J=2.2 Hz), 2.53 (m, 4H), 2.12 (t, 1H, J=2.4 Hz), 1.72 (m, 4H).

Preparation 20

1-[3-(2-Methoxy-4-nitro-phenyl)-prop-2-ynyl]-pyrrolidine

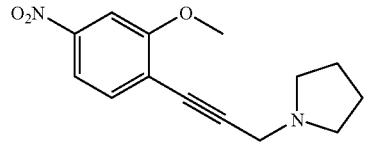

Dissolve 1-iodo-2-methoxy-4-nitro-benzene (618 mg, 2.21 mmol) in acetonitrile (10 mL) and treat sequentially with 1-prop-2-ynyl-pyrrolidine (352 mg, 3.22 mmol), Et$_3$N (2 mL), CuI (77 mg, 0.404 mmol) and Pd(PPh$_3$)$_4$ (360 mg, 0.311 mmol). Stir the mixture at room temperature for 3 h, then dilute with EtOAc (50 mL) and wash with saturated NaHCO$_3$ (30 mL). Dry, filter and concentrate the organic solution. Purify the crude material by flash chromatography, using a linear gradient of 50% EtOAc/hexanes to 100% EtOAc, to give the title compound as an orange oil (292 mg, 51%). MS (ES+) 261.1 (M+1)+. $^1$H NMR (400 MHz, CDCl$_3$) δ: 7.77 (dd, 1H, J=8.3, 2.2 Hz), 7.70 (d, 1H, J=2.2 Hz), 7.50 (d, 1H, J=8.3 Hz), 3.95 (s, 3H), 3.72 (s, 2H), 2.75-2.70 (m, 4H), 1.87-1.83 (m, 4H).

Preparation 21

1-(3,3-Diethoxy-prop-1-ynyl)-2-methoxy-4-nitro-benzene

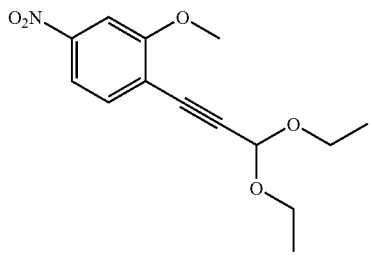

Prepare the title compound by essentially following the procedure as described for Preparation 20, using propargylaldehyde diethylacetal. $^1$H NMR (400 MHz, CDCl$_3$) δ: 7.78 (dd, 1H, J=8.6, 2.0 Hz), 7.70 (d, 1H, J=2.0 Hz), 7.55 (d, 1H, J=8.8 Hz), 5.52 (s, 1H), 3.95 (s, 3H), 3.87-3.78 (m, 2H), 3.71-3.63 (m, 2H), 1.27 (t, 6H, J=7.0 Hz).

Preparation 22

1-(2-Methoxy-4-nitro-phenyl)-4-triisopropylsilanyloxy-piperidine

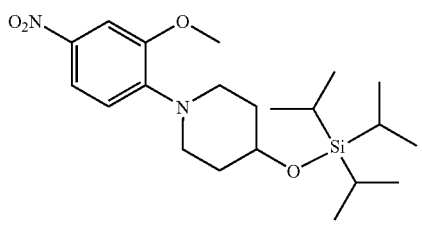

Dissolve 1-(2-methoxy-4-nitro-phenyl)-piperidin-4-ol (1.19 g, 4.72 mmol) in DMF (25 mL), followed by addition of triisopropylsilyl-trifluoromethanesulfonate (1.50 mL, 5.56 mmol) and Et$_3$N (0.80 mL, 5.87 mmol). Stir the solution at room temperature for 2 h, then add water (50 mL) and extract with EtOAc (2×50 mL). Combine the organic solutions and wash with water (2×30 mL) and brine (30 mL), then dry, filter, and concentrate. Purify the crude material by flash chromatography, using a linear gradient of 100% hexanes to 20% EtOAc/hexanes, to give the title compound as a yellow solid (1.55 g, 80%). MS (ES+) 409.3 (M+1)+. $^1$H NMR (400 MHz, CDCl$_3$) δ: 7.84 (dd, 1H, J=8.8, 2.6 Hz), 7.68 (d, 1H, J=2.6 Hz), 6.89 (d, 1H, J=8.8 Hz), 4.07-4.01 (m, 1H), 3.93 (s, 3H), 3.45-3.38 (m, 2H), 3.13-3.06 (m, 2H), 1.99-1.91 (m, 2H), 1.81-1.73 (m, 2H), 1.07-1.06 (m, 21H).

Preparation 23

3-Methoxy-4-(3-pyrrolidin-1-yl-propyl)phenylamine

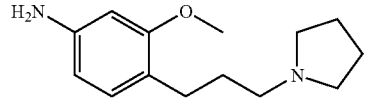

Dissolve 1-[3-(2-methoxy-4-nitro-phenyl)-prop-2-ynyl]-pyrrolidine (292 mg, 1.12 mmol) in EtOH (5 mL) and treat with 5% Pd/C. Purge the black mixture with hydrogen, then stir overnight at room temperature under a hydrogen atmosphere (1 atm). Filter the black mixture through a pad of Celite® and wash the solids with additional EtOH (20 mL). Concentrate the filtrate to give the title compound as an oil (240 mg, 91%). MS (ES+) 235.2 (M+1)+. $^1$H NMR (400 MHz, CDCl$_3$) δ: 6.88 (d, 1H, J=8.3 Hz), 6.22-6.18 (m, 2H), 3.73 (s, 3H), 3.55 (s, 2H), 2.53-2.41 (m, 8H), 1.79-1.72 (m, 6H).

Preparation 24

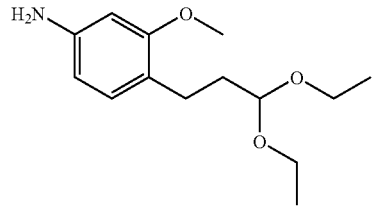

4-(3,3-Diethoxy-propyl)-3-methoxy-phenylamine

Prepare the title compound using procedures as essentially described for Preparation 23. $^1$H NMR (400 MHz, CDCl$_3$) δ: 6.89 (d, 1H, J=8.3 Hz), 6.23-6.20 (m, 2H), 4.48 (t, 1H, J=5.9 Hz), 3.75 (s, 3H), 3.68-3.60 (m, 2H), 3.64 (br s, 2H), 3.52-3.44 (m, 2H), 2.57-2.52 (m, 2H), 1.80-1.89 (m, 2H), 1.20 (t, 6H, J=7.0 Hz).

Preparation 25

7-Nitro-4H-benzo[1,4]oxazin-3-one

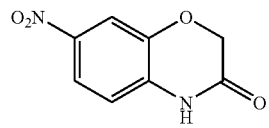

Mix 2-amino-5-nitro-phenol (10.0 g, 64.9 mmol) and NaHCO$_3$ (13.1 g, 155.7 mmol) in 4-methyl-pentan-2-one (40 mL) and water (40 mL). Cool the mixture to 0° C. and slowly add chloroacetyl chloride (6.0 mL, 75.3 mmol) with stirring. After the addition is complete, reflux the mixture for 5 h. Cool the mixture to room temperature and let stand for 2.5 days.

Collect the light yellow solid, wash with water and dry in a vacuum oven at 80° C. for 3 h. MS (ES−) 193.1 (M−1)⁻. ¹H NMR (400 MHz, DMSO-d6): δ 11.31 (s, 1H), 7.90 (dd, 1H, J=8.8, 2.2 Hz), 7.76 (d, 1H, J=2.6 Hz), 7.06 (d, 1H, J=8.8 Hz), 4.72 (s, 2H).

Preparation 26

7-Nitro-3,4-dihydro-2H-benzo[1,4]oxazine

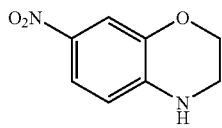

Mix 7-nitro-4H-benzo[1,4]oxazin-3-one (2.00 g, 10.3 mmol) in THF (10 mL) and treat with BH₃.THF (1.0M in THF, 35 mL). Heat the solution to reflux for 30 min, then cool to 0° C. and quench with 1N HCl (20 mL). Stir the solution for 30 min, then concentrate to ½ volume. Collect the orange solid, wash with water, and dry under vacuum to give the title compound (1.66 g, 89%). MS (ES+) 181.1 (M+1)⁺, MS (ES−) 179.2 (M−1)⁻. ¹H NMR (400 MHz, DMSO-d6): δ 7.68 (dd, 1H, J=8.8, 2.6 Hz), 7.53 (s, 1H), 7.47 (d, 1H, J=2.6 Hz), 6.63 (d, 1H, J=9.2 Hz), 4.15 (t, 2H, J=4.4 Hz), 3.44-3.40 (m, 2H), Preparation 27

5-nitro-1-(2-pyrrolidin-1-yl-ethyl)-1H-indole

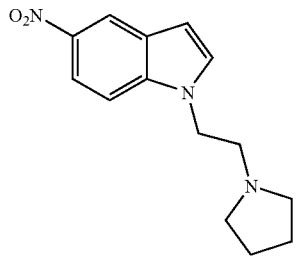

Dissolve 1-(2-chloro-ethyl)-pyrrolidine hydrochloride (2.36 g, 13.9 mmol) and 5-nitro-1H-indole (1.50 g, 9.23 mmol) in DMF (25 mL) and carefully treat with sodium hydride (60% dispersion, 1.50 g, 37.5 mmol). Stir the mixture at room temperature overnight, then dilute with cold water (100 mL) and extract with EtOAc (3×50 mL). Was the combined organic portions with water (2×50 mL) and brine (50 mL). Dry, filter and concentrate under vacuum. Purify the crude material by flash chromatography, using 100% acetone as eluant, to give the title compound as a yellow oil (2.08 g, 87%). MS (ES+) 260.1 (M+1)⁺. ¹H NMR (400 MHz, CDCl₃): δ 8.57 (d, 1H, J=2.2 Hz), 8.10 (dd, 1H, J=9.2, 2.2 Hz), 7.37 (d, 1H, J=9.2 Hz), 7.30 (d, 1H, J=3.1 Hz), 6.67 (d, 1H, J=3.1 Hz), 4.29 (t, 2H, J=7.3 Hz), 2.89 (t, 2H, J=7.0 Hz), 2.54 (m, 4H), 1.78 (m, 4H).

Prepare the compounds below, Preparations 28 to 36, by essentially following the procedure as described in Preparation 27, using the appropriate nitroaryl or nitroheterocycle.

| Prep | Product (Chemical Name) | Structure | MS (ES+) |
|---|---|---|---|
| 28 | 5-Nitro-1-(2-pyrrolidin-1-yl-ethyl)-1H-benzoimidazole | 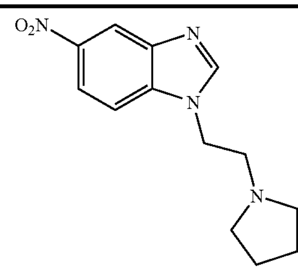 | 261.1 (M + 1)⁺ |
| 29 | 5-Nitro-1-(2-pyrrolidin-1-yl-ethyl)-1H-indazole | 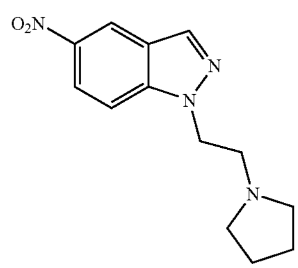 | 261.1 (M + 1)⁺ |
| 30 | 5-Nitro-2-(2-pyrrolidin-1-yl-ethyl)-2H-indazole | 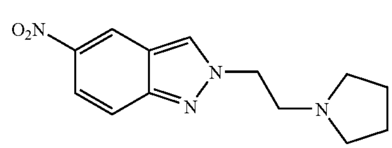 | 261.1 (M + 1)⁺ |

-continued

| Prep | Product (Chemical Name) | Structure | MS (ES+) |
|---|---|---|---|
| 31 | 2-Methyl-5-nitro-1-(2-pyrrolidin-1-yl-ethyl)-1H-indole | 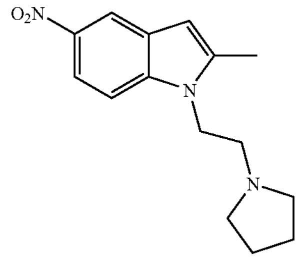 | 274.2 (M + 1)+ |
| 32 | 2,3-Dimethyl-5-nitro-1-(2-pyrrolidin-1-yl-ethyl)-1H-indole | 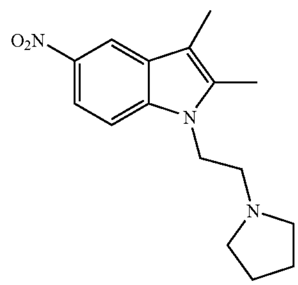 | 288.1 (M + 1)+. |
| 33 | 1-[2-(2-Chloro-4-nitro-phenoxy)-ethyl]-pyrrolidine | 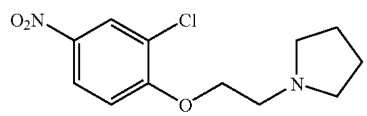 | 271.0 (M + 1)+ |
| 34 | 5-Nitro-1-(2-pyrrolidin-1-yl-ethyl)-2-trifluoromethyl-1H-benzoimidazole | 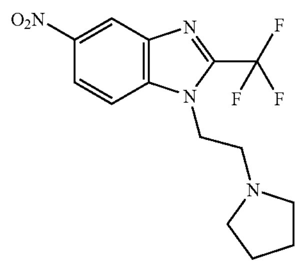 | 329.1 (M + 1)+ |
| 35 | 7-Nitro-4-(2-pyrrolidin-1-yl-ethyl)-3,4-dihydro-2H-benzo[1,4]oxazine | 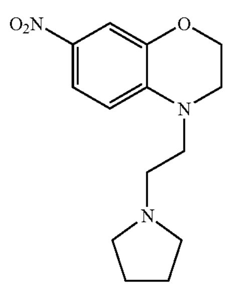 | 278.2 (M + 1)+ |
| 36 | 1-[2-(4-Nitro-phenoxy)-ethyl]-pyrrolidine | 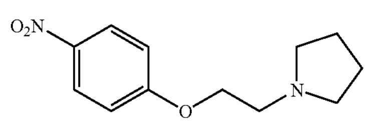 | 237.2 (M + 1)+ |

Preparation 37

(R)-1-(2-Methoxy-4-nitro-phenyl)-3-triisopropylsilanyloxy-pyrrolidine

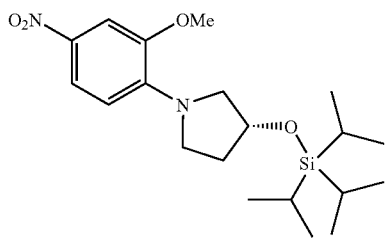

Combine 1-chloro-2-methoxy-4-nitro-benzene (10 g, 53.3 mmol) and (3R)-3-pyrrolidinol (9.3 g, 106.6 mmol). Heat the mixture to 100° C. overnight. Cool the mixture and dissolve in CH$_2$Cl$_2$ (200 mL) and wash with 1N NaOH (100 mL). Wash the extract with brine (3×50 mL). Dry the organic layer with Na$_2$SO$_4$, filter, and concentrate to give the intermediate pyrrolidinol as a crude dark reddish wet solid (12.17 g, 95%). MS (ES+) 239.1 (M+1)$^+$.

Dissolve the crude (R)-1-(2-methoxy-4-nitro-phenyl)-pyrrolidin-3-ol (10.9 g, 45.5 mmol) in dry pyridine (50 mL) and chill to 0° C. Add chloro-triisopropyl-silane (19.8 mL, 91 mmol) dropwise and then heat to 80° C. overnight. Remove the pyridine via reduced pressure and then wash the crude material with NaHSO$_3$ solution and extract with EtOAc (3×100 mL). Combine the organic solutions, then dry and concentrate to give the crude product. Purify over a silica plug with hexanes (300 mL) and flush with 10% EtOAc in hexanes (800 mL) to give the title compound as a reddish oil (17.85 g, 99%). MS (ES+) 395.2 (M+1)$^+$. $^1$H NMR (400 MHz, CDCl$_3$): δ 7.81 (dd, J=8.8, 2.2 Hz, 1H), 7.63 (d, J=2.2 Hz, 1H), 6.45 (d, J=88 Hz, 1H), 4.57-4.52 (m, 1H), 3.84 (s, 3H), 3.84-3.78 (m, 1H), 3.72-3.64 (m, 1H), 3.61-6.53 (m, 1H), 3.45 (dd, J=11.0, 2.2 Hz, 1H), 2.06-1.92 (m, 2H), 1.04-1.01 (m, 21H).

Preparation 38

1-(6-Nitro-1H-indol-3-yl)-2-pyrrolidin-1-yl-ethane-1,2-dione

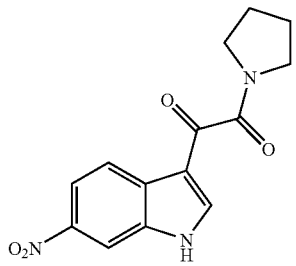

Add oxalyl chloride (11.6 g, 90.6 mmol) dropwise to a solution of 6-nitroindole (10.6 g, 65.4 mmol) in ether (100 mL). Stir at room temperature for 18 h, filter the precipitate formed, and dry. Dissolve the precipitate in CH$_2$Cl$_2$ (100 mL), cool to −20° C., and add pyrrolidine (16.0 mL, 191.5 mmol) dropwise. Warm to room temperature and stir for 2 h. Filter the solid from the reaction, wash several times with ether, and dry to give the title compound (8.5 g, 45%). MS (ES+) 288 (M+1)+.

Preparation 39

1-(1-Methyl-6-nitro-1H-indol-3-yl)-2-pyrrolidin-1-yl-ethane-1,2-dione

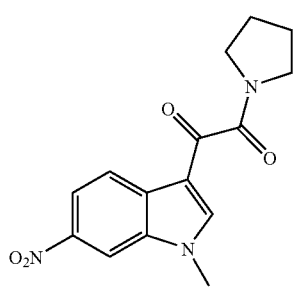

Add NaH (0.83 g, 20.8 mmol) to a solution of 1-(6-nitro-1H-indol-3-yl)-2-pyrrolidin-1-yl-ethane-1,2-dione (5.0 g, 17.42 mmol) in THF (60 mL). Stir at room temperature for 10 min, add iodomethane (1.18 mL, 19.2 mmol), and continue stirring for 18 h. Dilute with water and extract with EtOAc (2×). Filter the solid that formed between the layers during the extraction. Dry organic portion, concentrate, and combine the solids. Triturate the solid with ether, filter, and dry to obtain the title compound (5.20 g, 99%). $^1$H NMR (400 MHz, DMSO-d6): δ 8.59 (m, 2H), 8.30 (d, 1H, J=8.8 Hz), 8.17 (dd, 1H, J=8.8, 2.2 Hz), 4.01 (s, 3H), 3.48 (t, 2H, J=6.8 Hz), 3.41 (t, 2H, J=6.4 Hz), 1.85 (m, 4H).

Preparation 40

1-Methyl-6-nitro-3-(2-pyrrolidin-1-yl-ethyl)-1H-indole

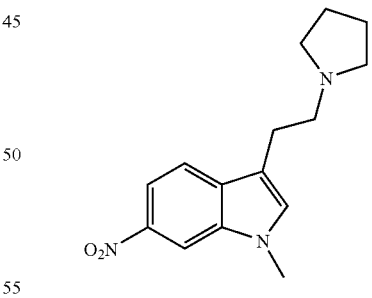

Treat a solution of 1-(1-methyl-6-nitro-1H-indol-3-yl)-2-pyrrolidin-1-yl-ethane-1,2-dione (5.0 g, 17.4 mmol) in THF (20 mL) with BH$_3$.THF (70 mL of 1N in THF, 70 mmol) and stir at room temperature for 18 h. Concentrate the reaction mixture and add EtOH (100 mL) followed by 5N HCl (20 mL) and reflux for 6 h. Concentrate and dilute with 1N NaOH (100 mL). Extract with CH$_2$Cl$_2$ (2×), then extract with EtOAc (2×). Combine the organics, dry, and concentrate. Purify by flash chromatography using 0-10% 2N NH$_3$/MeOH in CH$_2$Cl$_2$, to give the title compound (2.5 g, 53%). $^1$H NMR (400 MHz, DMSO-d6): δ 8.26 (d, 1H, J=2.2 Hz), 7.98 (dd, 1H, J=8.8, 1.8 Hz), 7.61 (d, 1H, is J=8.8 Hz), 7.19 (s, 1H), 3.84 (s, 3H), 2.97 (t, 2H, J=8.1 Hz), 2.76 (t, 2H, J=8.1 Hz), 2.61 (m, 4H), 1.83 (m, 4H).

Preparation 41

1-(2-Methoxy-4-nitro-benzyl)-4-methyl-piperazine

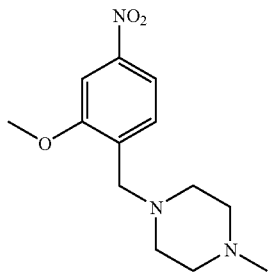

To a round bottom flask or vial containing 2-methoxy-4-nitro-benzaldehyde (1.0 g, 5.5 mmol), add dichloroethane (40 mL), 1-methylpiperazine (1.0 ml, 8.3 mmol), and sodium triacetoxyborohydride (3.5 g, 16.5 mmol). Stir at room temperature overnight. Quench with saturated aqueous NaHCO$_3$ and extract with CH$_2$Cl$_2$ (1×) and EtOAc (2×). Combine the organic portions, dry over MgSO$_4$, filter, and concentrate under vacuum. Purify the residue by flash chromatography on silica gel using a gradient of MeOH (0.005% NH$_4$OH)/CH$_2$Cl$_2$ (5% to 10%) to give the title compound. MS (ES+) 266.0 (M+1)$^+$. $^1$H NMR (CDCl$_3$): δ 7.80 (dd, J=8 Hz, 2 Hz, 1H), 7.66 (d, J=2 Hz, 1H), 7.56 (J=8 Hz, 1H), 3.89 (s, 3H), 3.58 (s, 2H), 2.52 (br. 4H), 2.45 (br, 2H), 2.28 (s, 3H).

Preparation 42

1-(2-Pyrrolidin-1-yl-ethyl)-1H-indol-5-ylamine

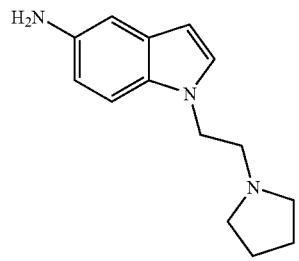

Dissolve 5-nitro-1-(2-pyrrolidin-1-yl-ethyl)-1H-indole (375 mg, 1.45 mmol) in ethanol (15 mL) and add 5% Pd/C (149 mg). Purge the black mixture with hydrogen (1 atm) and stir overnight under a hydrogen atmosphere. Filter the black mixture through Celite® and wash the solids with additional ethanol (~10 mL). Concentrate the filtrate to give the title compound as a yellow solid. MS (ES+) 230.2 (M+1)$^+$. $^1$H NMR (400 MHz, CDCl$_3$): δ: 7.17 (d, 1H, J=8.8 Hz), 7.05 (d, 1H, J=3.1 Hz), 6.92 (d, 1H, J=2.2 Hz), 6.67 (dd, 1H, J=8.3, 2.2 Hz), 6.29 (d, 1H, J=3.1 Hz), 4.21 (t, 2H, J=7.5 Hz), 3.37 (s, 2H), 2.86 (t, 2H, J=7.5 Hz), 2.55 (m, 4H), 1.79 (m, 4H).

Prepare the compounds below, Preparations 43 to 59, essentially following the procedure as described in Preparation 42 using the appropriate nitro compound which is previously prepared or commercially available.

| Prep | Product (Chemical Name) | Structure | MS (ES+) and/or NMR |
|---|---|---|---|
| 43 | 1-(2-Pyrrolidin-1-yl-ethyl)-1H-benzoimidazol-5-ylamine | 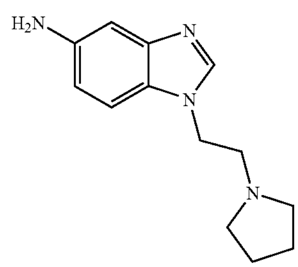 | 231.2 (M + 1)$^+$ |
| 44 | 1-(2-Pyrrolidin-1-yl-ethyl)-1H-indazol-5-ylamine | 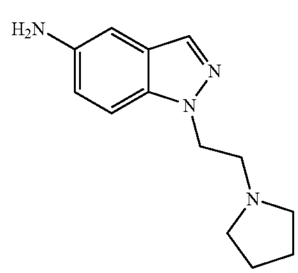 | 231.2 (M + 1)$^+$ |

-continued

| Prep | Product (Chemical Name) | Structure | MS (ES+) and/or NMR |
|---|---|---|---|
| 45 | 2-(2-Pyrrolidin-1-yl-ethyl)-2H-indazol-5-ylamine | 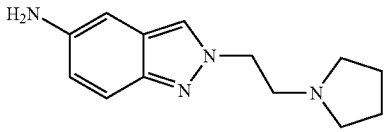 | 231.2 (M + 1)+ <br> 1H NMR (400 MHz, CDCl3): δ 7.70 (s, 1H), 7.52 (d, 1H, J = 9.2 Hz), 6.78 (dd, 1H, J = 9.2, 2.2 Hz), 6.73 (d, 1H, J = 2.2 Hz), 4.46 (t, 2H, J = 7.0 Hz), 3.53 (s, 2H), 3.05 (t, 4H, J = 6.8 Hz), 2.53 (m, 4H). |
| 46 | 2-Methyl-1-(2-pyrrolidin-1-yl-ethyl)-1H-indol-5-ylamine | 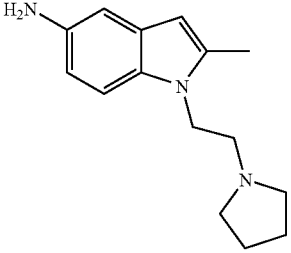 | 244.2 (M + 1)+. |
| 47 | 4-(2,2-Dimethoxy-ethoxy)-3-methoxy-phenylamine | 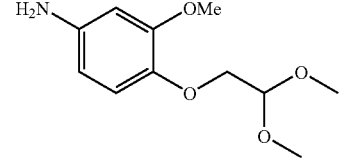 | 227.1 (M)+. |
| 48 | 3-Methoxy-4-(4-methyl-piperazin-1-ylmethyl)-phenylamine | 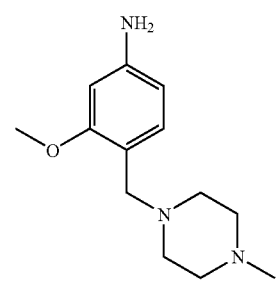 | 236.1 (M + 1)+ |
| 49 | 3-Methoxy-4-(2-pyrrolidin-1-yl-ethoxy)-phenylamine | 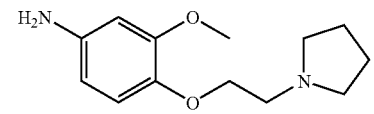 | 237.3 (M + 1)+ |
| 50 | 2,3-Dimethyl-1-(2-pyrrolidin-1-yl-ethyl)-1H-indol-5-ylamine | 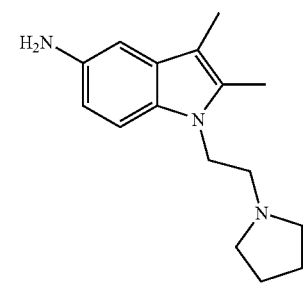 | 258.3 (M + 1)+ |

-continued

| Prep | Product (Chemical Name) | Structure | MS (ES+) and/or NMR |
|---|---|---|---|
| 51 | 6-(4-Methyl-piperazin-1-yl)-pyridin-3-ylamine | 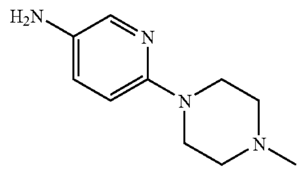 | 193.3 (M + 1)+ |
| 52 | 1-(2-Pyrrolidin-1-yl-ethyl)-2-trifluoromethyl-1H-benzoimidazol-5-ylamine | 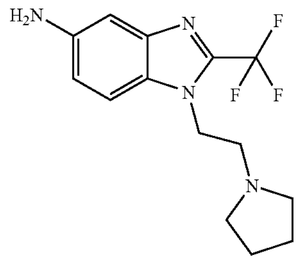 | 299.1 (M + 1)+. |
| 53 | 1-Methyl-3-(2-pyrrolidin-1-yl-ethyl)-1H-indol-6-ylamine | 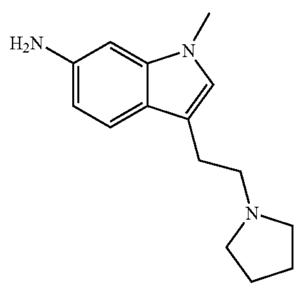 | 244.2 (M + 1)+. |
| 54 | 3-Methoxy-4-triisopropylsilanyloxy-phenylamine | 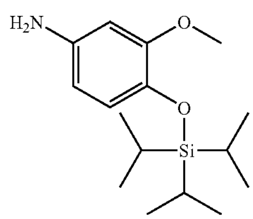 | 296.1 (M + 1)+ |
| 55 | 4-(2-Pyrrolidin-1-yl-ethyl)-3,4-dihydro-2H-benzo[1,4]oxazin-7-ylamine | 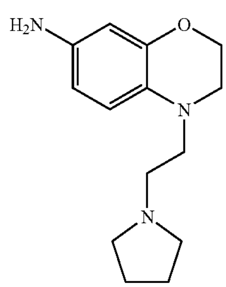 | 248.2 (M + 1)+ |
| 56 | 4-(2-Pyrrolidin-1-yl-ethoxy)-phenylamine | 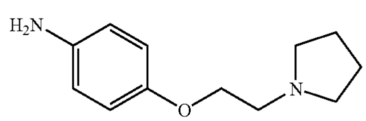 | 207.5 (M + 1)+ |
| 57 | 3-Methoxy-4-morpholin-4-yl-phenylamine | 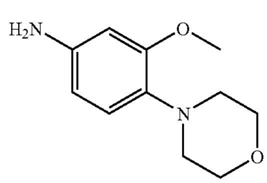 | 209.3 (M + 1)+. |

| Prep | Product (Chemical Name) | Structure | MS (ES+) and/or NMR |
|---|---|---|---|
| 58 | 4-(2,2-Dimethoxy-ethoxy)-phenylamine | 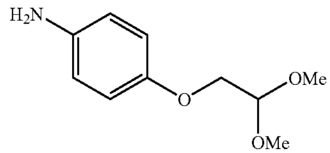 | $^1$H NMR (400 MHz, CDCl$_3$) δ: 6.76 (m, 2H), 6.21 (m, 2H), 4.68 (t, 1H, J = 5.4 Hz), 3.93 (d, 2H, J = 5.0 Hz), 3.44 (s, 3H), 3.38 (br s, 2H). |
| 59 | 4-(tert-Butyl-dimethyl-silanyloxy)-3-methoxy-phenylamine | 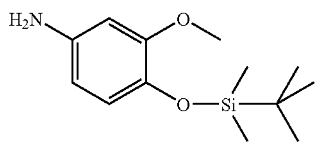 | $^1$H NMR (400 MHz, CDCl$_3$) δ: 6.65 (d, 1H, J = 7.9 Hz), 6.30 (d, 1H, J = 2.6 Hz), 6.21 (dd, 1H, J = 8.4, 2.6 Hz), 3.79 (s, 2H), 3.74 (s, 3H), 0.97 (s, 9H), 0.11 (s, 6H). |

Preparation 60

5-Nitro-1-triisopropylsilanyl-1H-indole

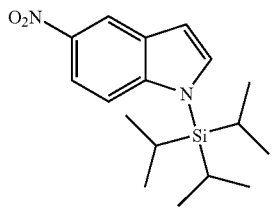

Dissolve 5-nitro-1H-indole (5.00 g, 30.8 mmol) in DMF (100 mL) and treat with NaH (1.62 g, 40.5 mmol). Stir the mixture at room temperature for 1 h and then add triisopropyl-silyl-trifluoromethanesulfonate (9.15 mL, 33.9 mmol). Stir the mixture for an additional 2 h then dilute with water (100 mL) and 1N HCl (40 mL), then extract with EtOAc (3×100 mL). Combine the organic solutions and wash with water (2×50 mL) and brine (50 mL). Dry, filter and concentrate the organic solution and purify the crude material by flash chromatography, using a linear gradient of 100% hexanes to 20% EtOAc/hexanes as eluant, to give the title compound as a clear yellow oil (6.30 g, 64%). $^1$H NMR (400 MHz, CDCl$_3$) δ: 8.56 (d, 1H, J=2.6 Hz), 8.05 (dd, 1H, J=9.0, 2.4 Hz), 7.51 (d, 1H, J=9.2 Hz), 7.38 (d, 1H, J=3.1 Hz), 6.78 (d, 1H, J=3.5 Hz), 1.74-1.66 (m, 3H), 1.14 (d, 18H, J=7.9 Hz).

Preparation 61

5-Nitro-1-triisopropylsilanyl-2,3-dihydro-1H-indole

Prepare the title compound by essentially following procedures as described for Preparation 60, using 5-nitroindoline. MS (ES+) 320.1 (M)$^+$. $^1$H NMR (400 MHz, CDCl$_3$): δ 7.95 (dd, 1H, J=8.8, 2.6 Hz), 7.92-7.90 (m, 1H), 6.56 (d, 1H, J=9.2 Hz), 3.86 (t, 2H, J=8.8 Hz), 3.08 (t, 2H, J=8.8 Hz), 1.46 (m, 3H), 1.14 (d, 18H, J=7.5 Hz).

Prepare the compounds below, Preparations 62-65, by essentially following the procedure as described in Preparation 42.

Preparation 62

1-Triisopropylsilanyl-2,3-dihydro-1H-indol-5-ylamine

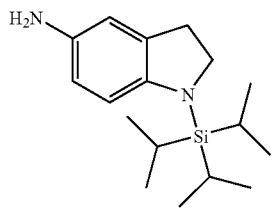

MS (ES+) 290.2 (M)+. ¹H NMR (400 MHz, CDCl₃): δ 6.62-6.27 (m, 3H), 3.66 (s, 2H), 2.89 (s, 2H), 1.45-1.33 (m, 3H), 1.10 (d, 18H, J=7.5 Hz).

Preparation 63

1-Triisopropylsilanyl-1H-indol-5-yl amine

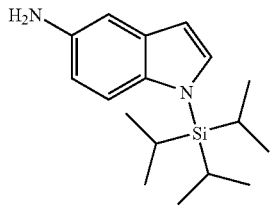

¹H NMR (400 MHz, CDCl₃): δ 7.29 (d, 1H, J=8.8 Hz), 7.16 (d, 1H, J=3.1 Hz), 6.92 (d, 1H, J=2.6 Hz), 6.59 (dd, 1H, J=8.8, 2.2 Hz), 6.43 (d, 1H, J=3.1 Hz), 1.69-1.61 (m, 3H), 1.12 (d, 18H, J=7.5 Hz).

Preparation 64

2,2-Dimethyl-propionic acid 4-amino-2-methoxy-phenyl ester

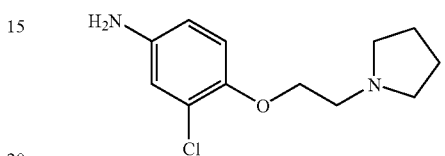

¹H NMR (400 MHz, CDCl₃): δ 6.76 (d, J=8.8 Hz, 1H), 6.31 (d, J=2.6 Hz, 1H), 6.25 (dd, J=8.8, 2.2 Hz, 1H), 3.74 (s, 3H), 1.34 (s, 9H).

Preparation 65

(R)-3-Methoxy-4-(3-triisopropylsilanyloxy-pyrrolidin-1-yl)-phenylamine

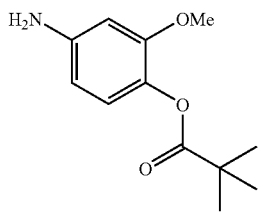

Dissolve (R)-1-(2-Methoxy-4-nitro-phenyl)-3-triisopropylsilanyloxy-pyrrolidine (12 g, 30.4 mmol) in EtOH (200 mL) and add 5% Pd/C (1.26 g). Purge the black mixture with hydrogen (1 atm) and stir overnight under a hydrogen atmosphere at ambient temperature at 60 psi. Filter the black mixture through Celite® and wash the solids with additional EtOH (100 mL). Concentrate the filtrate to give the title compound as a dark brown oil. ¹H NMR (400 MHz, CDCl₃): δ 6.76 (d, 1H, J=8.8 Hz), 6.31 (d, 1H, J=2.6 Hz), 6.25 (dd, 1H, J=8.8, 2.6 Hz), 3.74 (s, 3H), 1.34 (s, 9H). Note: title compound decomposed rapidly. Store compound in freezer immediately after use. MS (ES+) 365.2 (M+1)+.

Preparation 66

3-Chloro-4-(2-pyrrolidin-1-yl-ethoxy)-phenylamine

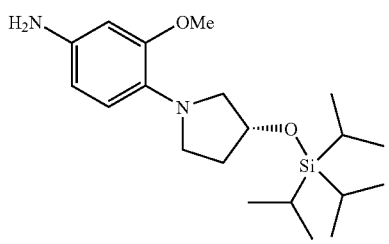

Add sodium borohydride (0.58 g, 15.26 mmol) to a solution of 1-[2-(2-chloro-4-nitro-phenoxy)-ethyl]-pyrrolidine (0.83 g, 3.07 mmol) and NiCl₂.6H₂O (1.45 g, 6.12 mmol) in MeOH (20 mL). Stir at room temperature for 2 h and add 10% NH₄OH solution. Extract with CH₂Cl₂ and then EtOAc, combine the organics, dry, and concentrate. Purify by flash chromatography using 0-10% 2N NH₃/MeOH in CH₂Cl₂, to give the title compound (0.5 g, 69%). MS (ES+) 241.2 (M+1)+. ¹H NMR (400 MHz, CDCl₃): δ 6.78 (d, 1H, J=8.4 Hz), 6.72 (d, 1H, J=3.1 Hz), 6.51 (dd, 1H, J=8.4, 3.1 Hz), 4.07 (t, 2H, J=6.2 Hz), 3.47 (s, 2H), 2.90 (t, 2H, J=6.2 Hz), 2.64 (m, 4H), 1.79 (m, 4H).

Preparation 67

2-(4-Chloro-phenyl)-4-(2-hydroxy-ethyl)-thiazole-5-carboxylic acid [3-methoxy-4-(4-triisopropylsilanyloxy-piperidin-1-yl)-phenyl]-amide

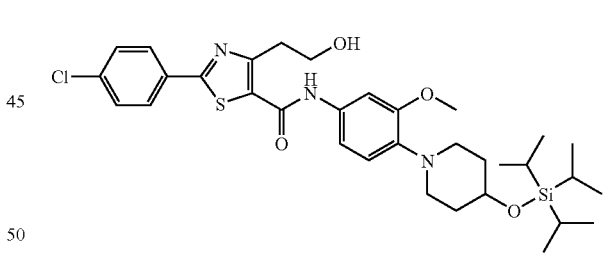

Dissolve 1-(2-Methoxy-4-nitro-phenyl)-4-triisopropylsilanyloxy-piperidine (1.53 g, 3.74 mmol) in THF (30 mL) and add 5% Pd/C then stir the slurry at room temperature under a hydrogen atmosphere for 3 h. Filter the black mixture through a pad of Celite® and concentrate the filtrate in vacuo to give 3-methoxy-4-(4-triisopropylsilanyloxy-piperidin-1-yl)-phenylamine (1.42 g, 100%) that was used immediately.

Dissolve the above 3-methoxy-4-(4-triisopropylsilanyloxy-piperidin-1-yl)-phenylamine (1.41 g, 3.72 mmol) in CH₂Cl₂ and add a trimethylaluminum solution (2.0M in hexanes, 2.25 mL, 4.50 mmol). Stir the solution at room temperature for 1 h, then add solid 2-(4-chloro-phenyl)-6,7-dihydro-pyrano[4,3-d]thiazol-4-one (1.01 g, 3.80 mmol) and continue stirring at room temperature overnight. Carefully quench reaction with saturated Rochelle's salt solution (15 mL) and stir at room temperature for 1 h. Extract the mixture with CH$_2$Cl$_2$ (3×20 mL). Combine all organic solutions, dry, filter, and concentrate in vacuo. Purify the crude material by flash chromatography using 2N NH$_3$/MeOH in CH$_2$Cl$_2$ as eluent to give the title compound as a sold (1.00 g, 42%). MS (ES+) 644.0 (M+1)+, (ES−) 642.3 (M−1)−. $^1$H NMR (400 MHz, CDCl$_3$): δ 10.76 (s, 1H), 8.00 (d, 2H, J=8.4 Hz), 7.60 (d, 2H, J=8.8 Hz), 7.35 (d, 1H, J=2.2 Hz), 7.13 (dd, 1H, J=8.8, 2.2 Hz), 6.88 (d, 1H, J=8.8 Hz), 5.78 (t, 1H, J=4.4 Hz), 3.94-3.86 (m, 3H), 3.78 (s, 3H), 3.21-3.13 (m, 4H), 2.78-2.70 (m, 2H), 1.93-1.85 (m, 2H), 1.67-1.57 (m, 2H), 1.06-1.04 (m, 21H).

Preparation 68

(R)-2-(4-Chloro-phenyl)-4-(2-hydroxy-ethyl)-thiazole-5-carboxylic acid [3-methoxy-4-(3-triisopropylsilanyloxy-pyrrolidin-1-yl)-phenyl]-amide

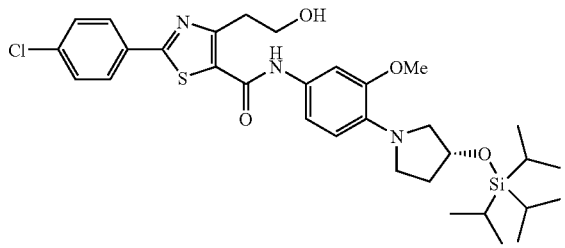

Charge an oven-dried round bottom flask with (R)-3-methoxy-4-(3-triisopropylsilanyloxy-pyrrolidin-1-yl)-phenylamine (750 mg, 2.05 mmol), purge with nitrogen, and dilute with CH$_2$Cl$_2$ (11 mL). Add trimethylaluminum (2M in hexanes, 1.03 mL, 2.05 mmol) dropwise by syringe and stir 20 min at room temperature. Add solid 2-(4-chloro-phenyl)-6,7-dihydro-pyrano[4,3-d]thiazol-4-one (364 mg, 1.37 mmol) to the reaction mixture and stir overnight at ambient temperature. Absorb the reaction mixture on silica gel and purify by silica gel flash chromatography, using a gradient of EtOAc/hexane (0-100%) to give the title compound (1.02 g, 73%). MS (ES+) 630.1 (M+1)+. $^1$H NMR (CDCl$_3$): δ 9.88 (bs, 1H), 7.82 (d, J=8.8 Hz, 2H), 7.48 (bs, 1H), 7.37 (d, J=8.8 Hz, 2H), 6.88 (d, J=8.4 Hz, 1H), 6.69 (bs, 1H), 4.60-4.52 (m, 1H), 4.19-4.11 (m, 2H), 3.81 (s, 3H), 3.69-3.58 (m, 1H), 3.39-3.29 (m, 1H), 3.26 (t, J=5.3 Hz, 2H), 3.20-3.02 (m, 2H), 2.21-2.08 (m, 1H), 1.93-1.83 (m, 1H), 1.59 (bs, 1H), 1.12-0.95 (m, 21H).

Preparation 69

2-(4-Chloro-phenyl)-4-(2-hydroxy-ethyl)-thiazole-5-carboxylic acid [1-(2-pyrrolidin-1-yl-ethyl)-1H-indol-5-yl]-amide

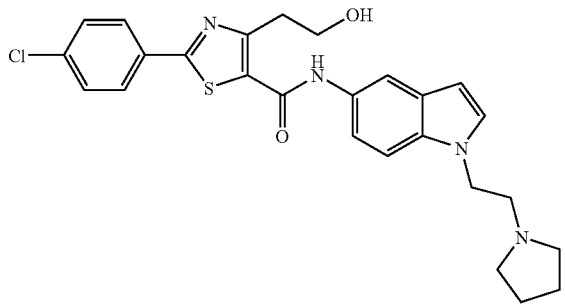

Dissolve 1-(2-pyrrolidin-1-yl-ethyl)-1H-indol-5-ylamine (247 mg, 1.08 mmol) in CH$_2$Cl$_2$ (5 mL), cool to 0° C., and treat with a solution of trimethylaluminum (2.0 M in hexanes, 0.7 mL, 1.40 mmol). Stir the solution at 0° C. for 15 min and then at room temperature for 30 min. Add 2-(4-chloro-phenyl)-6,7-dihydro-pyrano[4,3-d]thiazol-4-one (272 mg, 1.02 mmol) neat and stir the reaction at room temperature overnight. Carefully quench the mixture with saturated Rochelles salt solution (5 mL) and stir at room temperature for 1 h. Dilute with additional saturated Rochelles salt solution (10 mL) and extract with CH$_2$Cl$_2$ (3×20 mL). Combine the organic portions, dry, filter, and concentrate under vacuum. Triturate the crude solid with diethyl ether to give the title compound as a white powder (400 mg, 75%). MS (ES+) 495.1 (M+1)+ MS (ES−) 493.2 (M−1)−. $^1$H NMR (400 MHz, DMSO-d6): δ 10.78 (s, 1H), 8.01 (d, 2H, J=8.3 Hz), 7.92 (s, 1H), 7.60 (d, 2H, J=8.8 Hz), 7.46 (d, 1H, J=8.8 Hz), 7.40 (d, 1H, J=3.1 Hz), 7.34 (dd, 1H, J=8.8, 1.8 Hz), 6.41 (d, 1H, J=3.1 Hz), 5.84 (m, 1H), 4.26 (t, 2H, J=6.6 Hz), 3.91 (q, 2H, J=5.3 Hz), 3.21 (t, 2H, J=5.9 Hz), 2.78 (t, 2H, J=6.8 Hz), 2.46 (s, 4H), 1.65 (m, 4H).

Prepare the compounds below, Preparations 70 to 88, by essentially following the procedure as described in Preparation 69. Preparation 82 was made using 4-methyl-N$^2$-(2-morpholin-4-yl-ethyl)quinoline-2,6-diamine (Krahler, S. E.; Burger, A. J. Am. Chem. Soc., 1941, 63 2367-71).

Preparation 70

2-(4-Chloro-phenyl)-4-(2-hydroxy-ethyl)-thiazole-5-carboxylic acid [1-(2-pyrrolidin-1-yl-ethyl)-1H-benzoimidazol-5-yl]-amide

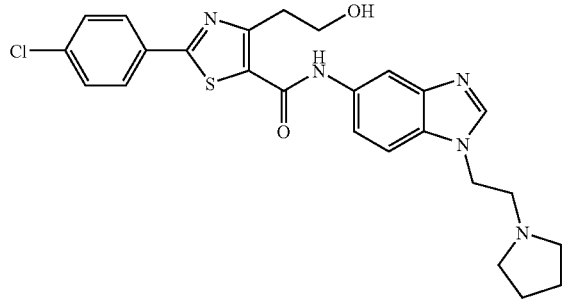

MS (ES+) 496.0 (M+1)+, (ES−) 494.2 (M−1)−.

Preparation 71

2-(4-Chloro-phenyl)-4-(2-hydroxy-ethyl)-thiazole-5-carboxylic acid [1-(2-pyrrolidin-1-yl-ethyl)-1H-indazol-5-yl]-amide

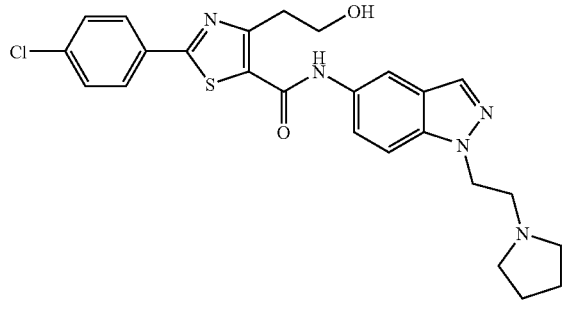

MS (ES+) 496.0 (M+1)+, (ES−) 494.2 (M−1)−.

Preparation 72

2-(4-Chloro-phenyl)-4-(2-hydroxy-ethyl)-thiazole-5-carboxylic acid [2-(2-pyrrolidin-1-yl-ethyl)-2H-indazol-5-yl]-amide

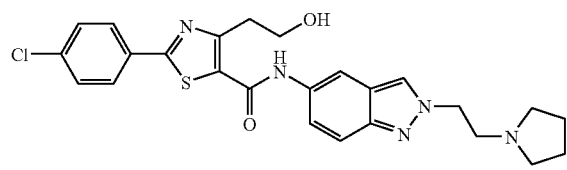

MS (ES+) 496.0 (M+1)$^+$, (ES−) 494.2 (M−1)$^−$.

Preparation 73

2-(4-Chloro-phenyl)-4-(2-hydroxy-ethyl)-thiazole-5-carboxylic acid [2-methyl-1-(2-pyrrolidin-1-yl-ethyl)-1H-indol-5-yl]-amide

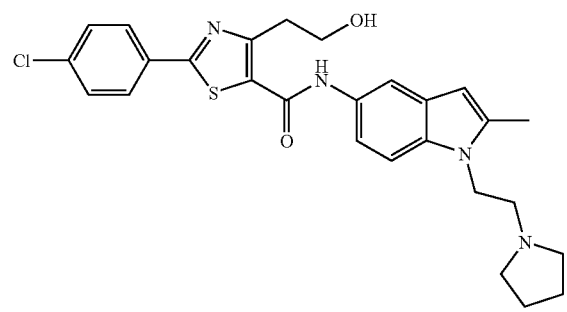

MS (ES+) 509.0 (M+1)$^+$, (ES−) 507.0 (M−1)$^−$.

Preparation 74

2-(4-Chloro-phenyl)-4-(2-hydroxy-ethyl)-thiazole-5-carboxylic acid [2,3-dimethyl-1-(2-pyrrolidin-1-yl-ethyl)-1H-indol-5-yl]-amide

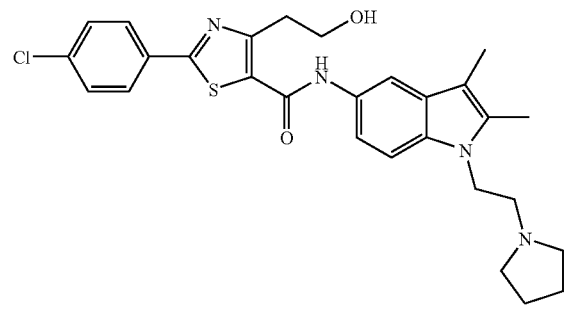

MS (ES+) 523.1 (M+1)$^+$.

Preparation 75

2-(4-Chloro-phenyl)-4-(2-hydroxy-ethyl)-thiazole-5-carboxylic acid [1-methyl-3-(2-pyrrolidin-1-yl-ethyl)-1H-indol-6-yl]-amide

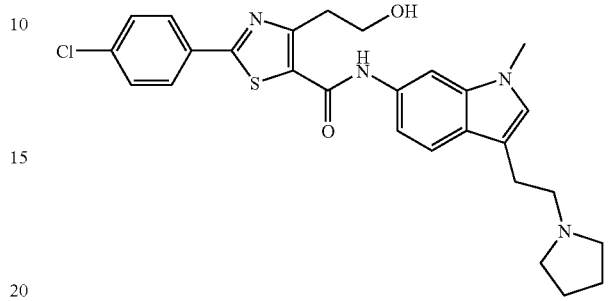

MS (ES+) 509.1 (M+1)$^+$.

Preparation 76

2-(4-Chloro-phenyl)-4-(2-hydroxy-ethyl)-thiazole-5-carboxylic acid [1-(2-pyrrolidin-1-yl-ethyl)-2-trifluoromethyl-1H-benzoimidazol-5-yl]-amide

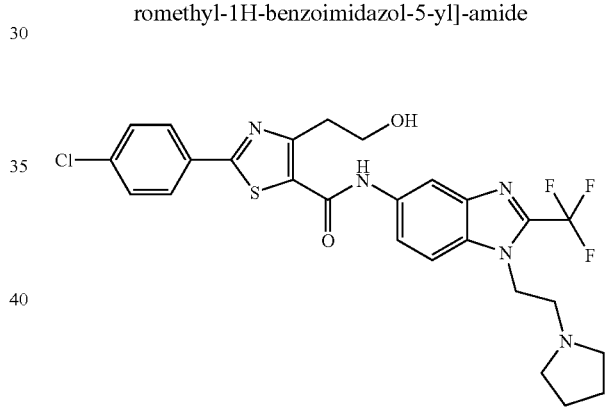

MS (ES+) 564.1 (M+1)$^+$.

Preparation 77

2-(4-Chloro-phenyl)-4-(2-hydroxy-ethyl)-thiazole-5-carboxylic acid (3-methoxy-4-triisopropylsilanyloxy-phenyl)-amide

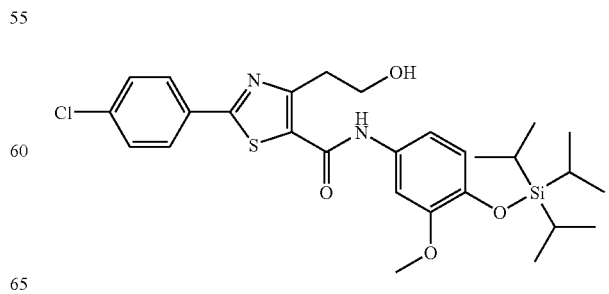

MS (ES+) 561.1 (M+1)$^+$.

Preparation 78

2-(4-Chloro-phenyl)-4-(2-hydroxy-ethyl)-thiazole-5-carboxylic acid [6-(4-methyl-piperazin-1-yl)-pyridin-3-yl]-amide

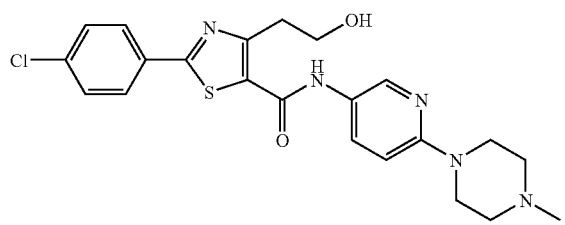

MS (ES+) 458.0 (M+1)+.

Preparation 79

2-(4-Chloro-phenyl)-4-(2-hydroxy-ethyl)-thiazole-5-carboxylic acid [3-chloro-4-(2-pyrrolidin-1-yl-ethoxy)-phenyl]-amide

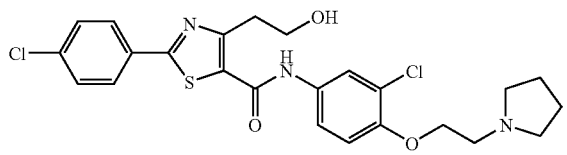

MS (ES+) 506.0 (M+1)+.

Preparation 80

2-(4-Chloro-phenyl)-4-(2-hydroxy-ethyl)-thiazole-5-carboxylic acid [4-(2-pyrrolidin-1-yl-ethyl)-3,4-dihydro-2H-benzo[1,4]oxazin-7-yl]-amide

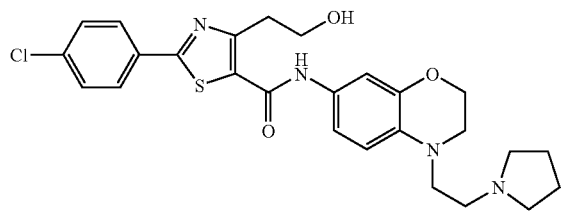

MS (ES+) 513.0 (M+1)+, (ES−) 511.2 (M−1)−.

Preparation 81

2-(4-Chloro-phenyl)-4-(2-hydroxy-ethyl)-thiazole-5-carboxylic acid [3-methoxy-4-(3-pyrrolidin-1-yl-propyl)-phenyl]-amide

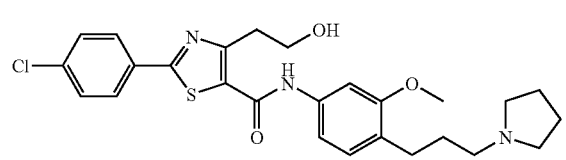

MS (ES+) 500.4 (M+1)+.

Preparation 82

2-(4-Chloro-phenyl)-4-(2-hydroxy-ethyl)-thiazole-5-carboxylic acid [4-methyl-2-(2-morpholin-4-yl-ethylamino)-quinolin-6-yl]-amide

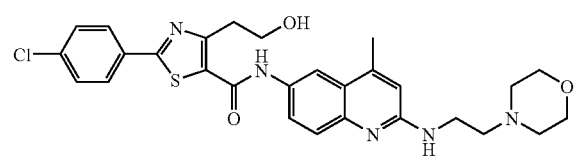

MS (ES+) 552.1 (M+1)+.

Preparation 83

2-(4-Chloro-phenyl)-4-(2-hydroxy-ethyl)-thiazole-5-carboxylic acid [4-(3,3-diethoxy-propyl)-3-methoxy-phenyl]-amide

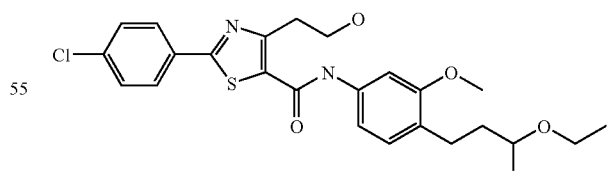

$^1$H NMR (400 MHz, CDCl$_3$): δ 9.99 (s, 1H), 7.85 (d, 2H, J=8.8 Hz), 7.54 (d, 1H, J=1.8 Hz), 7.41 (d, 2H, J=8.3 Hz), 7.04 (d, 1H, J=7.9 Hz), 6.87 (dd, 1H, J=8.1, 2.0 Hz), 4.50 (t, 1H, J=5.9 Hz), 4.19 (t, 2H, J=5.3 Hz), 3.82 (s, 3H), 3.69-3.60 (m, 2H), 3.53-3.45 (m, 2H), 3.29 (t, 2H, J=5.3 Hz), 2.62 (t, 2H, J=7.9 Hz), 1.91-1.81 (m, 2H), 1.23-1.17 (m, 6H).

Preparation 84

2-(4-Chloro-phenyl)-4-(2-hydroxy-ethyl)-thiazole-5-carboxylic acid [4-(2-pyrrolidin-1-yl-ethoxy)-phenyl]-amide

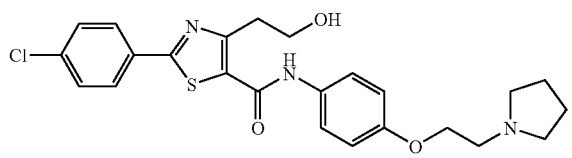

MS (ES+) 472.0 (M+1)⁺, 470.0 (M−1)⁻.

Preparation 85

2-(4-Chloro-phenyl)-4-(2-hydroxy-ethyl)-thiazole-5-carboxylic acid (3-methoxy-4-morpholin-4-yl-phenyl)-amide

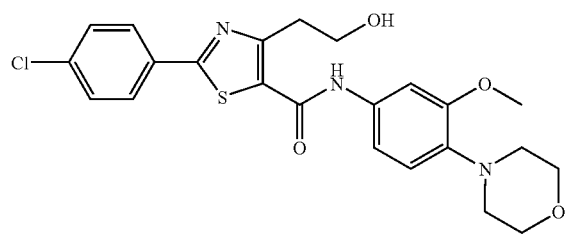

MS (ES+) 474.0 (M+1)+, (ES−) 472.3 (M−1)−.

Preparation 86

2-(4-Chloro-phenyl)-4-(2-hydroxy-ethyl)-thiazole-5-carboxylic acid (1-triisopropylsilanyl-1H-indol-5-yl)-amide

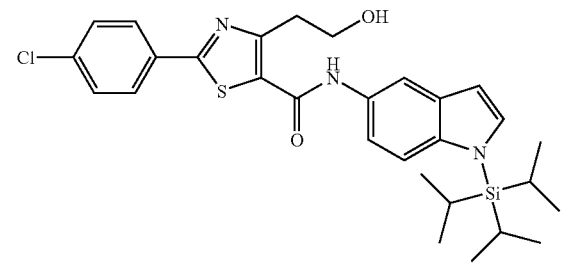

MS (ES+) 554.1 (M+1)⁺, 552.3 (M−1)⁻.

Preparation 87

2-(4-Chloro-phenyl)-4-(2-hydroxy-ethyl)-thiazole-5-carboxylic acid (1-triisopropylsilanyl-2,3-dihydro-1H-indol-5-yl)-amide

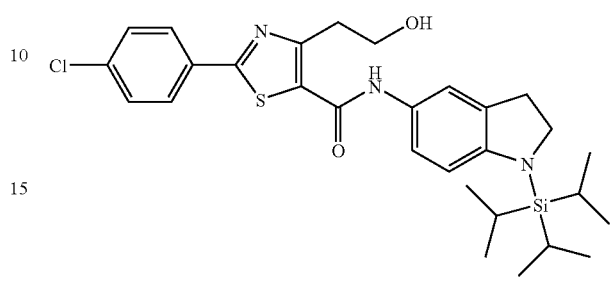

MS (ES+) 556.0 (M+1)⁺.

Preparation 88

2-(4-Chloro-phenyl)-4-(2-hydroxy-ethyl)-thiazole-5-carboxylic acid 3,4-dimethoxy-benzylamide

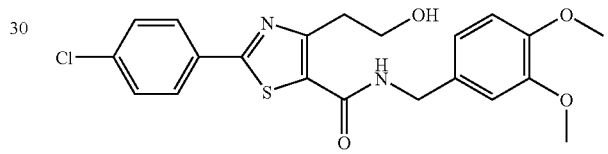

MS (ES+) 433.0 (M+1)⁺, MS (ES−) 431.0 (M−1)−. ¹H NMR (CDCl₃): δ 9.13 (t, 1H, J=5.7 Hz), 7.96 (d, 2H, J=8.8 Hz), 7.58 (d, 2H, J=8.8 Hz), 6.94 (d, 1H, J=1.8 Hz), 6.91 (d, 1H, J=7.9 Hz), 6.85 (dd, 1H, J=8.4, 1.8 Hz), 5.29 (t, 1H, J=4.6 Hz), 4.40 (d, 2H, J=5.7 Hz), 3.82-3.76 (m, 2H), 3.71 (s, 3H), 3.70 (s, 3H), 3.15 (t, 2H, J=6.2 Hz).

Preparation 89

2-(4-Chloro-phenyl)-4-(2-hydroxy-ethyl)-thiazole-5-carboxylic acid [4-(2,2-dimethoxy-ethoxy)-3-methoxy-phenyl]-amide

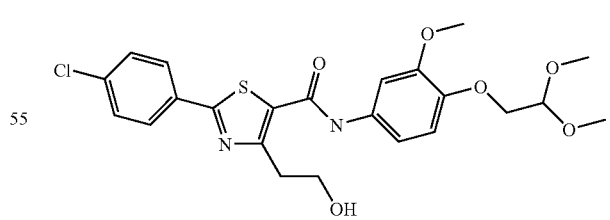

Method 1; Charge an oven-dried round bottom flask with 4-(2,2-dimethoxy-ethoxy)-3-methoxy-phenylamine (0.65 g, 2.88 mmol), purge with nitrogen, and dilute with toluene (5 mL). Add trimethylaluminum (2 M in hexanes, 1.44 mL, 2.88 mmol) dropwise by syringe and stir 5 min at room temperature. Add 2-(4-chloro-phenyl)-6,7-dihydro-pyrano[4,3-d]thiazol-4-one (0.51 g, 1.91 mmol) in toluene (20 mL), attach a reflux condenser and stir overnight in an 80° C. oil bath. Allow to cool to ambient temperature and add 1N HCl, extracting with EtOAc (3×). Dry the combined organic portions over MgSO$_4$, filter, and concentrate under vacuum. Purify by flash chromatography on silica gel, using a gradient of EtOAc/hexane (20%-70%) to give the title compound (0.78 g, 83%). Exact mass=492.1, MS (ES+) 493.4 (M+1)$^+$. $^1$H NMR (CDCl$_3$): δ 9.91 (s, 1H), 7.88 (dt, J=8.5, 2.2 Hz, 2H), 7.57 (ap d, 1H), 7.42 (dt, J=8.5, 2.2 Hz, 2H), 6.94 (dd, J=8.8, 2.4 Hz, 1H), 6.87 (d, J=8.8 Hz, 1H), 4.75 (t, J=5.2 Hz, 1H), 4.22 (t, J=5.2 Hz, 2H), 4.03 (d, J=5.2 Hz, 2H), 3.87 (s, 3H), 3.46 (s, 6H), 3.31 (t, J=5.2 Hz, 2H).

Prepare the compounds Preparations 90 and 91, by essentially following the procedures as described in Preparation 89, Method 1.

Preparation 90

2-(4-Chloro-phenyl)-4-(2-hydroxy-ethyl)-thiazole-5-carboxylic acid [4-(tert-butyl-dimethyl-silanyloxy)-3-methoxy-phenyl]-amide

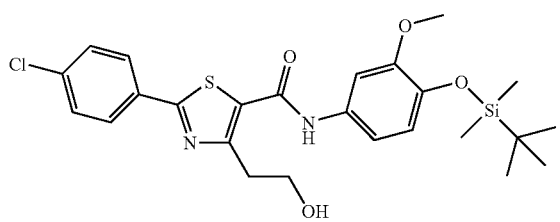

Exact mass 518, mass spectrum (ES) 519.3 (M+1)$^+$.

Preparation 91

2-(4-Chloro-phenyl)-4-(2-hydroxy-ethyl)-thiazole-5-carboxylic acid [3-methoxy-4-(4-methyl-piperazin-1-ylmethyl)-phenyl]-amide

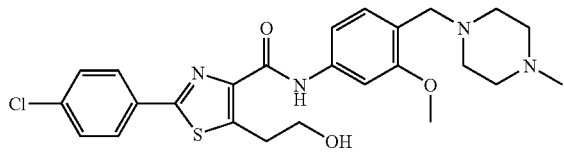

Exact mass: 500.0, MS (ES+): 501.3 (M+1)$^+$.

Preparation 92

2,2-Dimethyl-propionic acid 4-{[4-(2-hydroxy-ethyl)-2-(4-methoxy-phenyl)-thiazole-5-carbonyl]-amino}-2-methoxy-phenyl ester

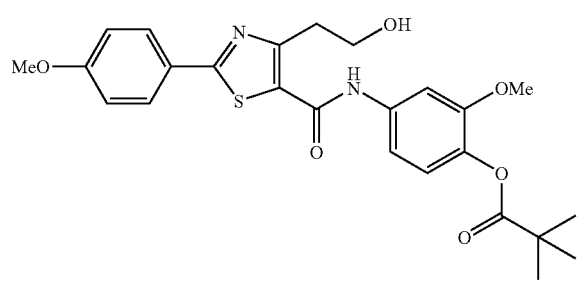

Method 2: Prepare the title compound by essentially following procedures as described in Preparation 89, Method 1, except the reaction mixture is run overnight at ambient temperature. Quench the reaction mixture with 1N HCl (20 mL) and extract with CH$_2$Cl$_2$ (3×10 mL). Dry the combined organic portions with Na$_2$SO$_4$, filter, and concentrate. Purify by flash chromatography on silica gel, using a gradient of EtOAc/hexane (20%-70%) to give the title compound. MS (ES+) 485.2 (M+1)$^+$. $^1$H NMR (CDCl$_3$): δ 10.01 (s, 1H), 7.90 (d, J=9.2 Hz, 2H), 7.70 (d, J=1.8 Hz, 1H), 6.95 (dd, J=8.4, 2.2 Hz, 2H), 6.92 (d, J=1.8 Hz, 1H), 6.91 (d, J=8.4 Hz, 1H), 4.18 (t, J=5.3 Hz, 2H), 3.85 (s, 3H), 3.79 (s, 3H), 3.29 (t, J=5.3 Hz, 2H), 1.36 (s, 9H).

Preparation 93

4-(2-Hydroxy-ethyl)-2-(4-methoxy-phenyl)-thiazole-5-carboxylic acid [4-(2,2-dimethoxy-ethoxy)-3-methoxy-phenyl]-amide

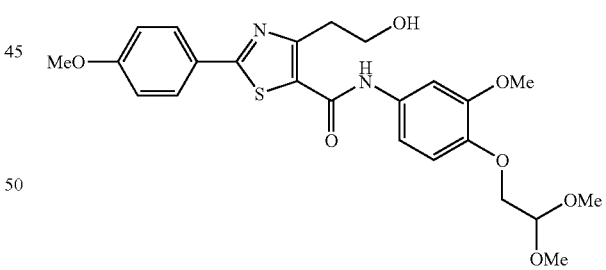

Method 3: Prepare the titled compound by essentially following procedures as described in Preparation 89, Method 1, except run the reaction overnight at ambient temperature. Cool the reaction mixture and add 1N NaOH (25 mL), extract with EtOAc (3×10 mL). Filter the solid precipitate from the partitioned aqueous/organic layer to give the title compound as a fine yellow powder. MS (ES+) 489.2 (M+1)$^+$. $^1$H NMR (d$_4$-MeOH): δ 7.92 (d, J=8.8 Hz, 2H), 7.44 (d, J=2.2 Hz, 1H), 7.11 (dd, J=8.8, 2.2 Hz, 1H), 7.03 (d, J=8.8 Hz, 2H), 6.95 (d, J=8.8 Hz, 1H), 4.70 (t, J=5.3 Hz, 1H), 4.05 (t, J=5.3 Hz, 2H), 3.99 (d, J=5.3 Hz, 2H), 3.86 (d, J=4.4 Hz, 6H), 3.44 (s, 6H), 3.25 (t, J=5.7 Hz, 2H).

Preparation 94

4-(2-Hydroxy-ethyl)-2-phenyl-thiazole-5-carboxylic acid [4-(2,2-dimethoxy-ethoxy)-phenyl]-amide

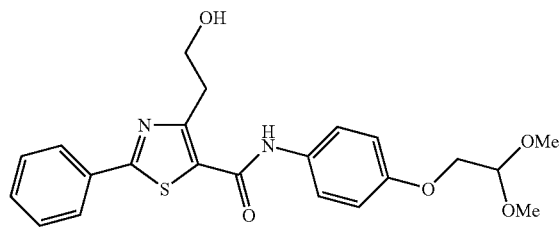

Method 4: Prepare the title compound by essentially following the procedures as described in Preparation 89, Method 1, using 4-(2,2-dimethoxy-ethoxy)-phenylamine (385 mg, 1.95 mmol) and 2-phenyl-6,7-dihydro-pyrano[4,3-d]thiazol-4-one (300 mg, 1.30 mmol). Heat the reaction mixture for 1 h at 70° C. (no reflux condenser is needed). Cool the reaction mixture and add water (20 mL), then extract with EtOAc (3×10 mL). Dry the organic layer with $Na_2SO_4$, filter, and concentrate. Purify on silica gel chromatography with 0-100% EtOAc in hexanes to give the title compound as a light brown solid. MS (ES+) 429.2 (M+1)$^+$, (ES−) 427.2 (M−1)$^-$.

Preparation 95

2-(3-Chloro-phenyl)-4-(2-hydroxy-ethyl)-thiazole-5-carboxylic acid [4-(2,2-dimethoxy-ethoxy)-3-methoxy-phenyl]-amide

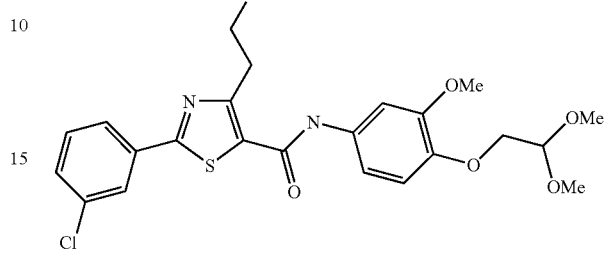

Method 5: Prepare the title compound by essentially following procedures as described in Preparation 89, Method 1, using the following alternate work-up. Dilute with 1N NaOH, and extract with EtOAc (3×10 mL). Dry with $Na_2SO_4$, filter, and concentrate. Add minimal amounts of $CH_2Cl_2$ to extract color and then add hexanes to give a solid precipitate. Collect the solid via vacuum filtration. Wash the solid with hexanes to give the title compound. MS (ES+) 493.2 (M+1)$^+$.

Prepare the following compounds, Preparations 96 to 98, by essentially following the procedures as described in Preparation 95, Method 5.

| Prep | Product (Chemical Name) | Structure | MS (ES+) |
|---|---|---|---|
| 96 | 4-(2-Hydroxy-ethyl)-2-(4-trifluoromethyl-phenyl)-thiazole-5-carboxylic acid [4-(2,2-dimethoxy-ethoxy)-3-methoxy-phenyl]-amide | 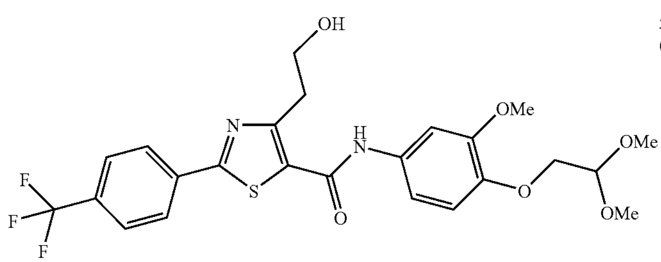 | 527.2 (M + 1)$^+$ |
| 97 | 2-(2,4-Dichloro-phenyl)-4-(2-hydroxy-ethyl)-thiazole-5-carboxylic acid [4-(2,2-dimethoxy-ethoxy)-3-methoxy-phenyl]-amide | 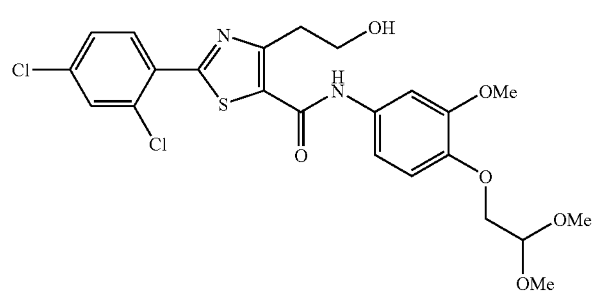 | 527 (M + 1)$^+$ |

-continued

| Prep | Product (Chemical Name) | Structure | MS (ES+) |
|---|---|---|---|
| 98 | 2-(4-Fluoro-phenyl)-4-(2-hydroxy-ethyl)-thiazole-5-carboxylic acid [4-(2,2-dimethoxy-ethoxy)-3-methoxy-phenyl]-amide | 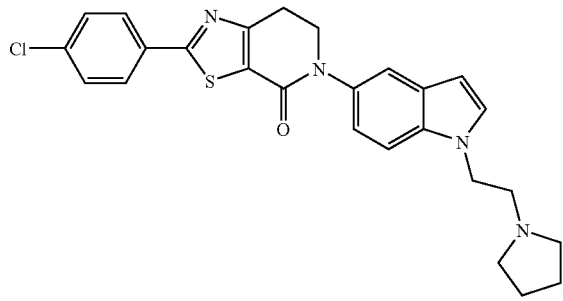 | 477.2 (M + 1)+ |

Example 1

2-(4-Chloro-phenyl)-5-[1-(2-pyrrolidin-1-yl-ethyl)-1H-indol-5-yl]-6,7-dihydro-5H-thiazolo[5,4-c]pyridin-4-one Method 1: Dissolve 2-(4-chloro-phenyl)-4-(4-hydroxyethyl)-thiazole-5-carboxylic acid [1-(2-pyrrolidin-1-yl-ethyl)-1H-indol-5-yl]-amide (390 mg, 0.79 mmol) in THF (8.0 mL) and cool to 0° C. Treat the solution with tributylphosphine (0.255 mL, 1.03 mmol) and diisopropylazodicarboxylate (0.205 mL, 1.04 mmol). Warm the solution to room temperature and stir overnight. Dilute the solution with EtOAc (50 mL) and wash with water (25 mL) and brine (25 mL). Dry the organic portion, filter and concentrate under vacuum. Purify the crude material by flash chromatography, using 8% 2N NH$_3$/MeOH in CHCl$_3$, to give a foam. Triturate the foam with ether to give the title compound as a yellow solid (289 mg, 77%). MS (ES+) 477.4 (M+1)+. $^1$H NMR (400 MHz, DMSO-d6): δ 8.06 (d, 2H, J=8.8 Hz), 7.62 (d, 2H, J=8.8 Hz), 7.49-7.53 (m, 2H), 7.44 (d, 1H, J=3.1 Hz), 7.13 (dd, 1H, J=8.8, 2.2 Hz), 6.43 (d, 1H, J=3.1 Hz), 4.29 (t, 2H, J=6.6 Hz), 4.11 (t, 2H, J=6.8 Hz), 3.29 (t, 2H, J=6.8 Hz), 2.80 (t, 2H, J=6.8 Hz), 2.49 (m, 4H), 1.66 (m, 4H).

Prepare Example 2 to 13 and Preparations 99 to 106 by essentially following the procedures as described in Example 1, Method 1, using the appropriate intermediate 4-hydroxyethyl-thiazole.

Example 2

2-(4-Chloro-phenyl)-5-[1-(2-pyrrolidin-1-yl-ethyl)-1H-benzoimidazol-5-yl]-6,7-dihydro-5H-thiazolo[5,4-c]pyridin-4-one

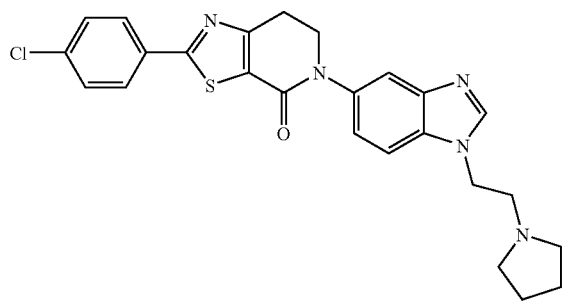

MS (ES+) 478.4 (M+1)+. $^1$H NMR (400 MHz, CDCl$_3$): δ 8.03 (s, 1H), 7.93 (d, 2H, J=8.8 Hz), 7.72 (d, 1H, J=1.8 Hz), 7.43-7.46 (m, 3H), 7.34-7.38 (m, 1H), 4.37 (s, 2H), 4.18 (t, 2H, J=7.0 Hz), 3.32 (t, 2H, J=7.0 Hz), 2.99 (s, 2H), 2.61 (s, 4H), 1.82 (s, 4H).

Example 3

2-(4-Chloro-phenyl)-5-[1-(2-pyrrolidin-1-yl-ethyl)-1H-indazol-5-yl]-6,7-dihydro-5H-thiazolo[5,4-c]pyridin-4-one

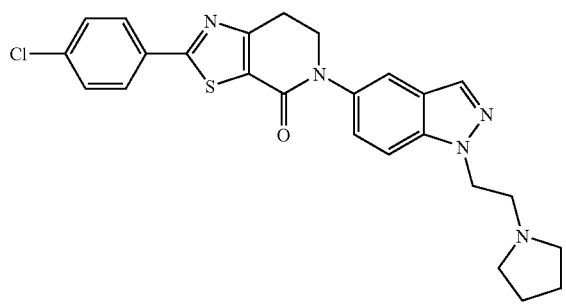

MS (ES+) 478.4 (M+1)+. $^1$H NMR (400 MHz, CDCl$_3$): δ 7.98 (s, 1H), 7.93 (d, 2H, J=8.8 Hz), 7.65 (d, 1H, J=1.3 Hz), 7.48 (d, 1H, J=8.8 Hz), 7.44 (d, 2H, J=8.8 Hz), 7.39 (dd, 1H, J=9.0, 2.0 Hz), 4.55 (t, 2H, J=7.5 Hz), 4.16 (t, 2H, J=7.0 Hz), 3.32 (t, 2H, J=7.0 Hz), 3.01 (t, 2H, J=7.3 Hz), 2.58 (s, 4H), 1.78 (m, 4H).

Example 4

2-(4-Chloro-phenyl)-5-[2-(2-pyrrolidin-1-yl-ethyl)-2H-indazol-5-yl]-6,7-dihydro-5H-thiazolo[5,4-c]pyridin-4-one

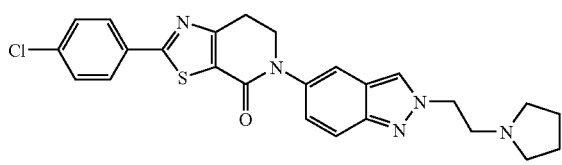

MS (ES+) 478.4 (M+1)+. $^1$H NMR (400 MHz, DMSO-d6): δ 8.42 (d, 1H, J=0.9 Hz), 8.06 (d, 2H, J=8.8 Hz), 7.67-7.69 (m, 1H), 7.60-7.64 (m, 3H), 7.25 (dd, 1H, J=9.0, 2.0 Hz), 4.54 (t, 2H, J=6.4 Hz), 4.14 (t, 2H, J=6.8 Hz), 3.28 (t, 2H, J=7.0 Hz), 2.97 (t, 2H, J=6.4 Hz), 2.47 (s, 4H), 1.65 (m, 4H).

Example 5

2-(4-Chloro-phenyl)-5-[2-methyl-1-(2-pyrrolidin-1-yl-ethyl)-1H-indol-5-yl]-6,7-dihydro-5H-thiazolo[5,4-c]pyridin-4-one

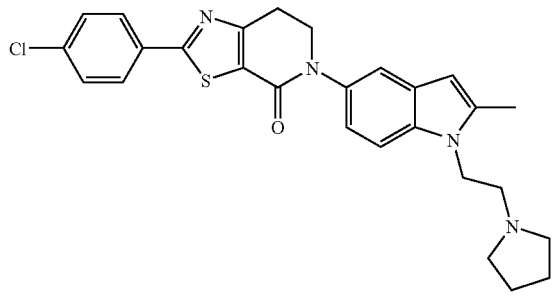

MS ES+) 491.1 (M+1)+. $^1$H NMR (400 MHz, DMSO-d6): δ 8.05 (d, 2H, J=7.9 Hz), 7.62 (d, 2H, J=8.3 Hz), 7.37-7.42 (m, 2H), 7.06 (d, 1H, J=8.3 Hz), 6.22 (s, 1H), 4.23 (s, 2H), 4.09 (t, 2H, J=6.6 Hz), 3.27 (s, 2H), 2.69 (s, 2H), 2.43 (s, 3H), 1.69 (s, 4H), 1.69 (s, 4H).

Example 6

2-(4-Chloro-phenyl)-5-[3-methoxy-4-(4-methyl-piperazin-1-ylmethyl)-phenyl]-6,7-dihydro-5H-thiazolo[5,4-c]pyridin-4-one MS (ES+) 483.3 (M+1)+. $^1$H NMR (CDCl$_3$): δ 7.92 (d, J=7.4 Hz, 2H), 7.44 (d, J=7.4 Hz, 2H), 7.39 (d, J=8.0 Hz, 1H), 6.92 (d, J=1.8 Hz, 1H), 6.86 (dd, J=8.0 Hz, 1.8 Hz, 1H), 4.11 (t, J=5.2. Hz, 2H), 3.82 (s, 3H), 3.55 (s, 2H), 3.28 (t, J=5.2 Hz, 2H), 2.62-2.44 (m, 8H), 2.29 (s, 3H).

Example 7

2-(4-Chloro-phenyl)-5-[2,3-dimethyl-1-(2-pyrrolidin-1-yl-ethyl)-1H-indol-5-yl]-6,7-dihydro-5H-thiazolo[5,4-c]pyridin-4-one MS (ES+) 505 (M+1)+. $^1$H NMR (400 MHz, CDCl$_3$: δ 7.94 (d, 2H, J=8.3 Hz), 7.44 (m, 3H), 7.27 (d, 1H, J=10.1 Hz), 7.10 (dd, 1H, J=8.6, 2.0 Hz), 4.24 (brs, 2H), 4.15 (t, 2H, J=6.8 Hz), 3.31 (t, 2H, J=7.0 Hz), 2.77 (brs, 2H), 2.63 (brs, 4H), 2.37 (s, 3H), 2.22 (s, 3H), 1.85 (brs, 4H).

Example 8

2-(4-Chloro-phenyl)-5-[1-methyl-3-(2-pyrrolidin-1-yl-ethyl)-1H-indol-6-yl]-6,7-dihydro-5H-thiazolo[5,4-c]pyridin-4-one MS (ES+) 491.1 (M+1)+. $^1$H NMR (400 MHz, CDCl$_3$): δ 7.93 (d, 2H, J=8.3 Hz), 7.63 (d, 1H, J=8.3 Hz), 7.45 (d, 2H, J=8.3 Hz), 7.29 (s, 1H), 7.04 (d, 1H, J=8.3 Hz), 6.92 (s, 1H), 4.17 (t, 2H, J=7.0 Hz), 3.72 (s, 3H), 3.32 (t, 2H, J=6.8 Hz), 2.99 (t, 2H, J=8.1 Hz), 2.78 (t, 2H, J=8.1 Hz), 2.63 (m, 4H), 1.84 (m 4H).

Example 9

2-(4-Chloro-phenyl)-5-[4-(2-pyrrolidin-1-yl-ethyl)-3,4-dihydro-2H-benzo[1,4]oxazin-7-yl]-6,7-dihydro-5H-thiazolo[5,4-c]pyridin-4-one

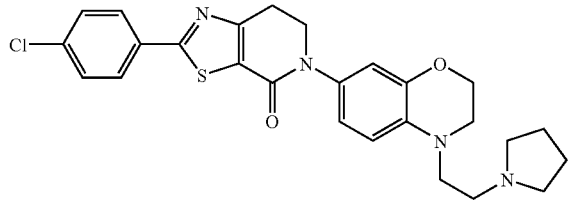

MS (ES+) 495.0 (M+1)+. $^1$H NMR (400 MHz, DMSO-d6): δ 8.03 (d, 2H, J=8.4 Hz), 7.61 (d, 2H, J=8.4 Hz), 6.78 (dd, 1H, J=8.6, 2.4 Hz), 6.73-6.67 (m, 2H), 4.16 (t, 2H, J=4.0 Hz), 3.99 (t, 2H, J=7.0 Hz), 3.42-3.37 (m, 4H), 3.22 (t, 2H, J=7.0 Hz), 2.61 (t, 2H, J=6.8 Hz), 2.52-2.47 (m, 4H), 1.68 (s, 4H).

Example 10

2-(4-Chloro-phenyl)-5-[3-methoxy-4-(3-pyrrolidin-1-yl-propyl)-phenyl]-6,7-dihydro-5H-thiazolo[5,4-c]pyridin-4-one

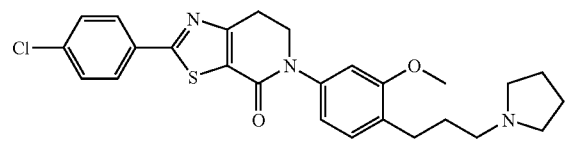

MS (ES+) 482.0 (M+1)+. $^1$H NMR (400 MHz, CDCl$_3$): δ 7.93 (d, 2H, J=8.3 Hz), 7.45 (d, 2H, J=7.9 Hz), 7.16 (d, 1H, J=7.9 Hz), 6.89 (d, 1H, J=1.8 Hz), 6.82 (dd, 1H, J=7.9, 2.2 Hz), 4.12 (t, 2H, J=6.8 Hz), 3.82 (s, 3H), 3.29 (t, 2H, J=7.0 Hz), 2.65 (t, 2H, J=7.7 Hz), 2.54 (s, 6H), 1.87-1.77 (m, 6H).

Example 11

2-(4-Chloro-phenyl)-5-[4-methyl-2-(2-morpholin-4-yl-ethylamino)-quinolin-6-yl]-6,7-dihydro-5H-thiazolo[5,4-c]pyridin-4-one

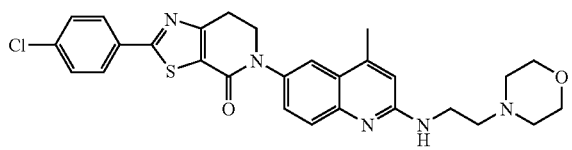

MS (ES+) 534.0 (M+1)+. $^1$H NMR (400 MHz, DMSO-d6): δ 8.07 (d, 2H, J=8.3 Hz), 7.71 (s, 1H), 7.63 (d, 2H, J=8.3 Hz), 7.49 (s, 2H), 6.84 (m, 1H), 6.67 (s, 1H), 4.18 (t, 2H, J=6.8 Hz), 3.59 (t, 4H, J=4.4 Hz), 3.54-3.48 (m, 2H), 3.35-3.28 (m, 2H), 2.51 (m, 2H), 2.44 (m, 7H).

Example 12

2-(4-Chloro-phenyl)-5-[4-(2-pyrrolidin-1-yl-ethoxy)-phenyl]-6,7-dihydro-5H-thiazolo[5,4-c]pyridin-4-one

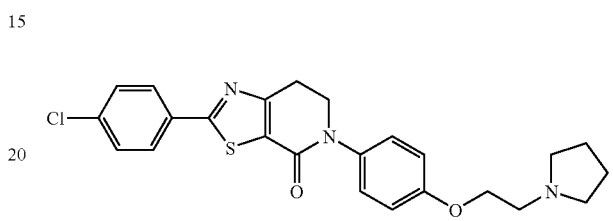

MS (ES+) 454.0 (M+1)+. $^1$H NMR (400 MHz, CDCl$_3$): δ 7.93 (d, 2H, J=8.8 Hz), 7.45 (d, 2H, J=8.8 Hz), 7.25 (d, 2H, J=8.8 Hz), 6.96 (d, 2H, J=8.8 Hz), 4.15 (t, 2H, J=5.7 Hz), 4.08 (t, 2H, J=7.0 Hz), 3.28 (t, 2H, J=6.8 Hz), 2.94 (s, 2H), 2.67 (s, 4H), 1.83 (s, 4H).

Example 13

2-(4-Chloro-phenyl)-5-(3-methoxy-4-morpholin-4-yl-phenyl)-6,7-dihydro-5H-thiazolo[5,4-c]pyridin-4-one, hydrochloride salt

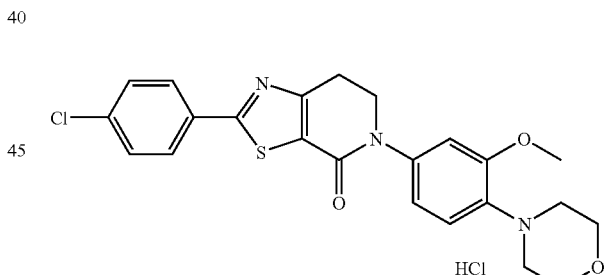

Prepare the hydrochloride salt of the free base by mixing 2-(4-chloro-phenyl)-5-(3-methoxy-4-morpholin-4-yl-phenyl)-6,7-dihydro-5H-thiazolo[5,4-c]pyridin-4-one (273 mg, 0.599 mmol) in MeOH (4 mL) and adding a 1.0M HCl/ether (0.7 mL, 0.70 mmol) solution. After all solids dissolve, cool the solution to −20° C. for 4 days. Collect the white precipitate by filtration, wash with ether, and dry under vacuum to give the title compound as a white solid (275 mg, 57%). MS (ES+) 456.0 (M+1)+. $^1$H NMR (400 MHz, DMSO-d6): δ 8.05 (d, 2H, J=8.4 Hz), 7.62 (d, 2H, J=8.4 Hz), 7.18 (s, 1H), 7.12 (s, 1H), 7.00-6.96 (m, 1H), 5.69 (s, 1H), 4.10 (t, 2H, J=7.0 Hz), 3.86-3.80 (m, 7H), 3.27 (t, 2H, J=7.0 Hz), 3.20-3.12 (m, 4H).

Preparation 99

2-(4-Chloro-phenyl)-5-[4-(2,2-dimethoxyethoxy)-3-methoxy-phenyl]-6,7-dihydro-5H-thiazolo[5,4-c]pyridin-4-one

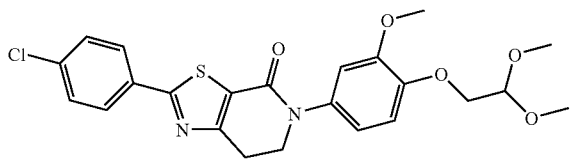

Exact mass=474.1, MS (ES+) 475.2 (M+1)$^+$. $^1$H NMR (CDCl$_3$): δ 7.93 (d, J=8.5 Hz, 2H), 7.45 (d, J=8.5 Hz, 2H), 6.97-6.93 (m, 2H), 6.83 (dd, J=8.5, 2.5 Hz, 1H), 4.76 (t, J=5.2 Hz, 1H), 4.09 (t, J=7.0 Hz, 2H), 4.06 (d, J=5.2 Hz, 2H), 3.86 (s, 3H), 3.46 (s, 6H), 3.29 (t, J=7.0 Hz, 2H).

Preparation 100

5-[4-(2,2-Dimethoxy-ethoxy)-3-methoxy-phenyl]-2-(4-methoxy-phenyl)-6,7-dihydro-5H-thiazolo[5,4-c]pyridin-4-one

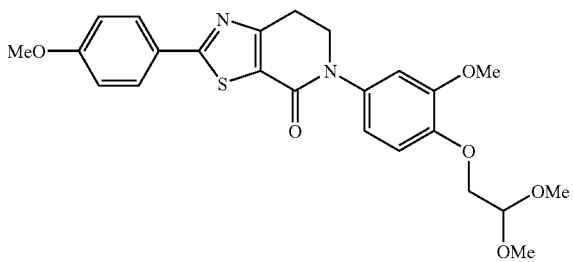

MS (ES+) 471.3 (M+1)$^+$. $^1$H NMR (CDCl$_3$): δ 8.01 (d, J=8.8 Hz, 2H), 7.00 (d, J=9.2 Hz, 2H), 6.96-6.99 (m, 2H), 6.81-6.87 (m, 1H), 4.76 (t, J=5.3 Hz, 1H), 4.09 (t, J=7.0 Hz, 2H), 4.06 (d, J=5.3 Hz, 2H), 3.89 (s, 3H), 3.86 (s, 3H), 3.46 (s, 6H), 3.34 (t, J=7.0 Hz, 2H).

Preparation 101

5-[4-(2,2-Dimethoxy-ethoxy)-phenyl]-2-phenyl-6,7-dihydro-5H-thiazolo[5,4-c]pyridin-4-one

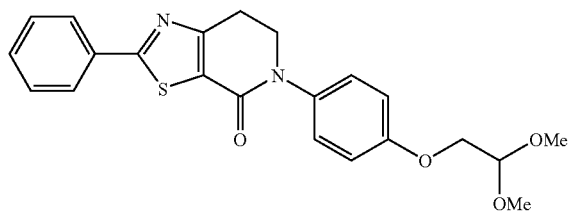

MS (ES+) 411.2 (M+1)$^+$. $^1$H NMR (CDCl$_3$): δ 8.02 (d, J=7.9 Hz, 2H), 7.52-7.49 (m, 3H), 7.31 (d, J=9.2 Hz, 2H), 7.00 (d, J=8.8 Hz, 2H), 4.77 (t, J=5.3 Hz, 1H), 4.12 (t, J=6.6 Hz, 2H), 4.06 (d, J=5.3 Hz, 2H), 3.50 (s, 6H), 3.33 (t, J=7.0 Hz, 2H).

Preparation 102

5-[4-(tert-Butyl-dimethyl-silanyloxy)-3-methoxy-phenyl]-2-(4-chloro-phenyl)-6,7-dihydro-5H-thiazolo[5,4-c]pyridin-4-one

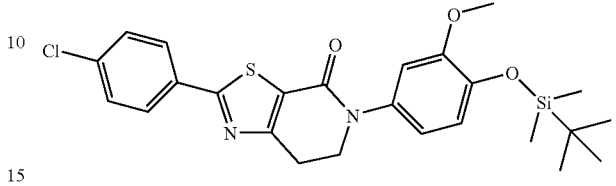

Exact mass=500.1, MS (ES+) 501.3 (M+1)$^+$. $^1$H NMR (CDCl$_3$): δ7.93 (d, J=8.6 Hz, 2H), 7.44 (d, J=8.6 Hz, 2H), 6.90 (d, J=8.4 Hz, 1H), 6.86 (d, J=8.4 Hz, 1H), 6.75 (dd, J=8.4, 2.5 Hz, 1H), 4.09 (t, J=7.0 Hz, 2H), 3.81 (s, 3H), 3.28 (t, J=7.0 Hz, 2H), 1.00 (s, 9H), 0.17 (s, 6H).

Preparation 103

2-(4-Chloro-phenyl)-5-(3-methoxy-4-triisopropylsilanyloxy-phenyl)-6,7-dihydro-5H-thiazolo[5,4-c]pyridin-4-one

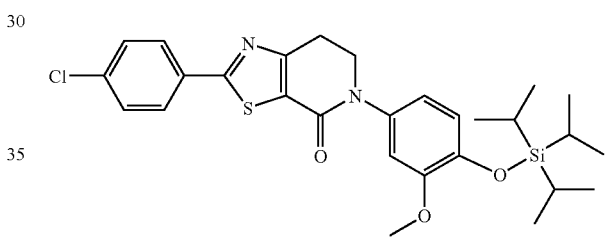

MS (ES+) 543.4 (M+1)$^+$. $^1$H NMR (400 MHz, CDCl$_3$): δ 7.92 (d, 2H, J=8.4 Hz), 7.43 (d, 2H, J=8.8 Hz), 6.86 (m, 2H), 6.72 (dd, 1H, J=8.4, 2.6 Hz), 4.07 (t, 2H, J=6.8 Hz), 3.78 (s, 3H), 3.26 (t, 2H, J=6.8 Hz), 1.23 (m, 3H), 1.08 (d, 18H, J=7.5 Hz).

Preparation 104

2-(4-Chloro-phenyl)-5-[3-methoxy-4-(4-triisopropyl-silanyloxy-piperidin-1-yl)-phenyl]-6,7-dihydro-5H-thiazolo[5,4-c]pyridin-4-one

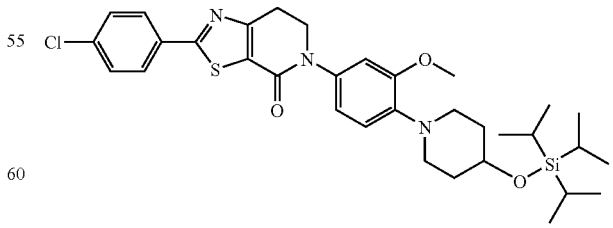

MS (ES+) 626.0 (M+1)+. $^1$H NMR (400 MHz, CDCl$_3$): δ 7.92 (d, 2H, J=8.8 Hz), 7.44 (d, 2H, J=8.4 Hz), 6.96 (d, 1H, J=8.4 Hz), 6.88 (d, 1H, J=2.2 Hz), 6.84 (dd, 1H, J=8.4, 2.6 Hz), 4.09 (t, 2H, J=7.0 Hz), 4.00-3.94 (m, 1H), 3.86 (s, 3H), 3.27 (t, 4H, J=7.0 Hz), 2.90-2.83 (m, 2H), 2.01-1.93 (m, 2H), 1.84-1.75 (m, 2H), 1.08-1.06 (m, 21H).

Preparation 105

2-(4-Chloro-phenyl)-5-(1-triisopropylsilanyl-2,3-dihydro-1H-indol-5-yl)-6,7-dihydro-5H-thiazolo[5,4-c]pyridin-4-one

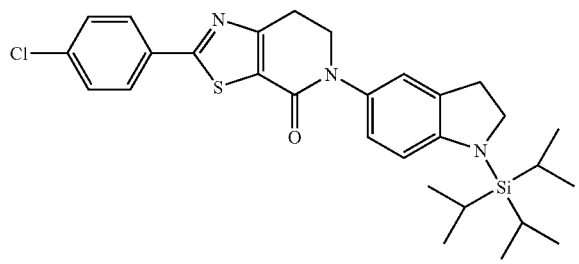

MS (ES+) 538.0 (M+1)+. 1H NMR (400 MHz, CDCl3): δ 7.91 (d, 2H, J=8.3 Hz), 7.43 (d, 2H, J=8.3 Hz), 7.05-7.03 (m, 1H), 6.86 (dd, 1H, J=8.3, 2.2 Hz), 6.61 (d, 1H, J=8.8 Hz), 4.04 (t, 2H, J=6.8 Hz), 3.74 (t, 2H, J=8.6 Hz), 3.23 (t, 2H, J=6.8 Hz), 3.00 (t, 2H, J=8.8 Hz), 1.47-1.38 (m, 3H), 1.13 (d, 18H, J=7.5 Hz).

Preparation 106

2-(4-Chloro-phenyl)-5-(3,4-dimethoxy-benzyl)-6,7-dihydro-5H-thiazolo[5,4-c]pyridin-4-one

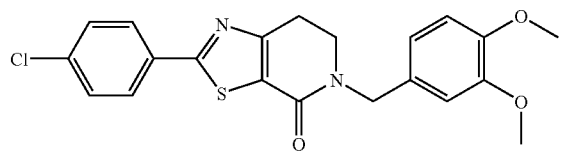

MS (ES+) 415.0 (M+1)+. 1H NMR (CDCl3): δ 7.88 (d, 2H, J=8.4 Hz), 7.41 (d, 2H, J=8.8 Hz), 6.88-6.85 (m, 2H), 6.81 (d, 1H, J=8.8 Hz), 4.66 (s, 2H), 3.86 (s, 3H), 3.85 (s, 3H), 3.58 (t, 2H, J=7.0 Hz), 3.07 (t, 2H, J=7.0 Hz).

Preparation 107

2-(3-Chloro-phenyl)-5-[4-(2,2-dimethoxy-ethoxy)-3-methoxy-phenyl]-6,7-dihydro-5H-thiazolo[5,4-c]pyridin-4-one

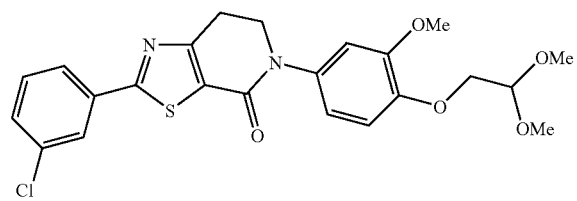

Method 2: Prepare the title compound by essentially following procedures as described for Example 1, Method 1, with the following exceptions. When the reaction is complete remove the solvent via reduced pressure. Dissolve the residue in minimal amounts of CH2Cl2, then add hexanes until a solid precipitates. Collect the solid via vacuum filtration. Wash the solid with hexanes several times to give the title compound. MS (ES+) 475.2 (M+1)+. 1H NMR (CDCl3): δ 8.02 (s, 1H), 7.85 (d, J=7.5 Hz, 1H), 7.49-7.39 (m, 2H), 6.97-6.93 (m, 2H), 6.87-6.82 (m, 1H), 4.77 (t, J=5.4 Hz, 1H), 4.10 (t, J=7.0 Hz, 2H), 4.07 (d, J=4.8 Hz, 2H), 3.86 (s, 3H), 3.46 (s, 6H), 3.30 (t, J=7.0 Hz, 2H).

Prepare the compounds below, Preparation 108 to 110, by essentially following the procedure as described in Preparation 107, Method 2, using the appropriate 4-hydroxy-ethyl-thiazole intermediate.

Preparation 108

5-[4-(2,2-Dimethoxy-ethoxy)-3-methoxy-phenyl]-2-(4-trifluoromethyl-phenyl)-6,7-dihydro-5H-thiazolo[5,4-c]pyridin-4-ne

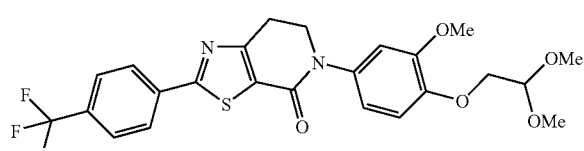

MS (ES+) 509.2 (M+1)+.

Preparation 109

2-(2,4-Dichloro-phenyl)-5-[4-(2,2-dimethoxy-ethoxy)-3-methoxy-phenyl]-6,7-dihydro-5H-thiazolo[5,4-c]pyridin-4-one

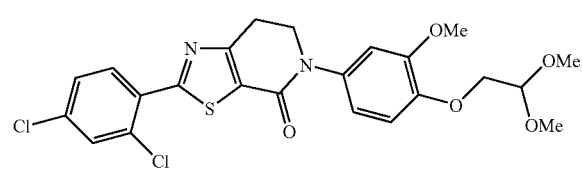

MS (ES+) 509.0 (M+1)+.

Preparation 110

5-[4-(2,2-Dimethoxy-ethoxy)-3-methoxy-phenyl]-2-(4-fluoro-phenyl)-6,7-dihydro-5H-thiazolo[5,4-c]pyridin-4-one

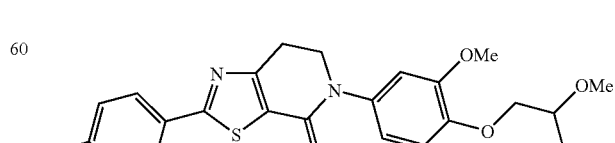

MS (ES+) 459.2 (M+1)+.

Preparation 111

{4-[2-(4-Chloro-phenyl)-4-oxo-6,7-dihydro-4H-thiazolo[5,4-c]pyridin-5-yl]-2-methoxy-phenoxy}-acetaldehyde

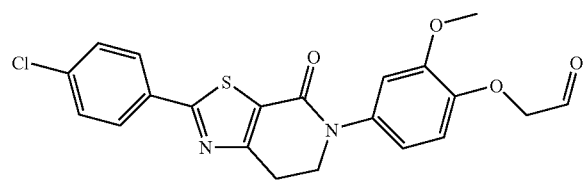

Method 1: Combine 2-(4-chloro-phenyl)-5-[4-(2,2-dimethoxy-ethoxy)-3-methoxy-phenyl]-6,7-dihydro-5H-thiazolo[5,4-c]pyridin-4-one (0.695 g, 1.46 mmol), p-toluenesulfonic acid (0.224 g, 1.16 mmol), acetone (10 mL) and water (2 mL). Attach a reflux condenser and stir at 70° C. overnight. Concentrate under vacuum, neutralize with saturated aqueous NaHCO$_3$, and extract with EtOAc (3×). Wash the combined organic portions with brine, dry over MgSO$_4$, and concentrate under vacuum to give the title compound. $^1$H NMR (CDCl$_3$): δ 9.90 (s, 1H), 7.93 (d, J=8.6 Hz, 2H), 7.45 (d, J=8.6 Hz, 2H), 7.01-6.84 (m, 3H), 4.62 (d, J=1.2 Hz, 2H), 4.13-4.05 (m, 2H), 3.86 (s, 3H), 3.30 (t, J=6.1 Hz, 2H).

Preparation 112

{2-Methoxy-4-[2-(4-methoxy-phenyl)-4-oxo-6,7-dihydro-4H-thiazolo[5,4-c]pyridin-5-yl]-phenoxy}-acetaldehyde

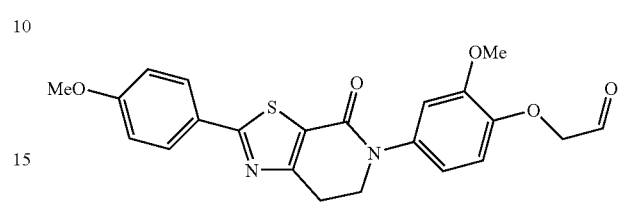

Method 2: Dissolve 5-[4-(2,2-Dimethoxy-ethoxy)-3-methoxy-phenyl]-2-(4-methoxy-phenyl)-6,7-dihydro-5H-thiazolo[5,4-c]pyridin-4-one (145 mg, 0.309 mmol) in THF (2 ml) and 1N HCl solution (360 µl). Heat to 50-60° C. overnight (no reflux condenser used). Cool reaction mixture, filter solid via vacuum filtration and wash solid with H$_2$O to give the title compound. MS (ES+) 425.4 (M+1)$^+$.

Prepare the compounds in the table below, Preparations 113 to 117, by essentially following the procedure as described in Preparation 112, Method 2 using the appropriate starting acetal.

| Prep | Name | Structure | MS |
|---|---|---|---|
| 113 | {4-[2-(4-Methoxy-phenyl)-4-oxo-6,7-dihydro-4H-thiazolo[5,4-c]pyridin-5-yl]-phenoxy}-acetaldehyde | 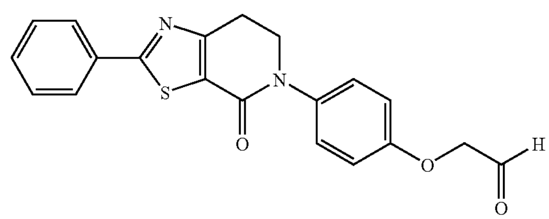 | MS (ES+) 397.2 (M + MeOH)$^+$. |
| 114 | {4-[2-(3-Chloro-phenyl)-4-oxo-6,7-dihydro-4H-thiazolo[5,4-c]pyridin-5-yl]-2-methoxy-phenoxy}-acetaldehyde | 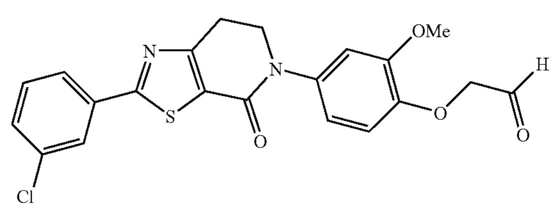 | MS (ES+) 429.0 (M + 1)$^+$. |
| 115 | {2-Methoxy-4-[4-oxo-2-(4-trifluoromethyl-phenyl)-6,7-dihydro-4H-thiazolo[5,4-c]pyridin-5-yl]-phenoxy}-acetaldehyde; compound with methane | 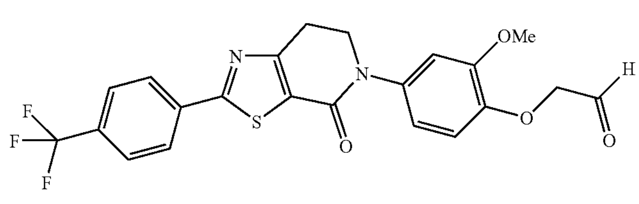 | (ES+) 463.3 (M + 1)$^+$. |

| Prep | Name | Structure | MS |
|---|---|---|---|
| 116 | {4-[2-(2,4-Dichloro-phenyl)-4-oxo-6,7-dihydro-4H-thiazolo[5,4-c]pyridin-5-yl]-2-methoxy-phenoxy}-acetaldehyde | 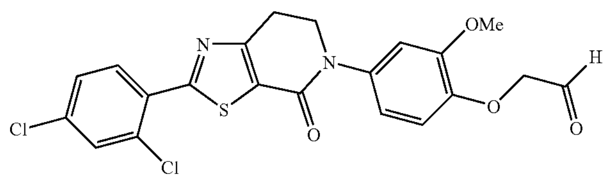 | MS (ES+) 463.0 (M + 1)+. |
| 117 | {4-[2-(4-Fluoro-phenyl)-4-oxo-6,7-dihydro-4H-thiazolo[5,4-c]pyridin-5-yl]-2-methoxy-phenoxy}-acetaldehyde | 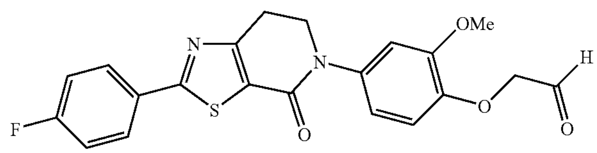 | MS (ES+) 413.3 (M + 1)+. |

General Procedure 1

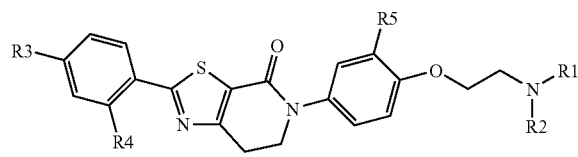

To a round bottom flask or vial containing {4-[2-(4-chloro-phenyl)-4-oxo-6,7-dihydro-4H-thiazolo[5,4-c]pyridin-5-yl]-2-methoxy-phenoxy}-acetaldehyde (0.064 g, 0.15 mmol) add dichloroethane (1.5 mL), a secondary amine (1.2 molar equivalent), and sodium triacetoxyborohydride (1.1 molar equivalent). Stir at room temperature overnight. Quench with saturated aqueous NaHCO$_3$, extract with CH$_2$Cl$_2$ (1×), EtOAc (2×), dry over MgSO$_4$, filter and concentrate under vacuum. Purify by flash chromatography on silica gel, using a gradient of MeOH (2 N NH$_3$)/EtOAc (5%-15%) to give the title compound.

Prepare Examples 14 to 29 by essentially following the general procedure as described above, using the appropriate amine reagent. For Examples 28 and 29 prepare the citrate salt by dissolving the free base in acetone and treating with a stoichiometric amount of citric acid.

Example 14

2-(4-Chloro-phenyl)-5-[3-methoxy-4-(2-pyrrolidin-1-yl-ethoxy)-phenyl]-6,7-dihydro-5H-thiazolo[5,4-c]pyridin-4-one

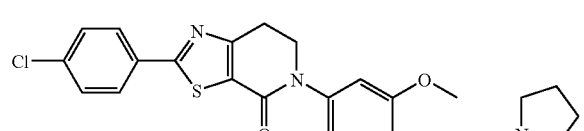

Exact mass=483.1, MS (ES+) 484.2 (M+1)+. $^1$H NMR (CDCl$_3$): δ 7.93 (dt, J=8.5, 2.1 Hz, 2H), 7.45 (dt, J=8.5, 2.1 Hz, 2H), 6.93 (m, 2H), 6.84 (dd, J=8.6, 2.4 Hz, 1H), 4.18 (t, J=6.6 Hz, 2H), 4.09 (t, J=7.0 Hz, 2H), 3.86 (s, 3H), 3.28 (t, J=7.0 Hz, 2H), 2.96 (t, J=6.6 Hz, 2H), 2.64 (br s, 4H), 1.81 (m, 4H).

Example 15

2-(4-Chloro-phenyl)-5-[3-methoxy-4-(2-piperidin-1-yl-ethoxy)-phenyl]-6,7-dihydro-5H-thiazolo[5,4-c]pyridin-4-one

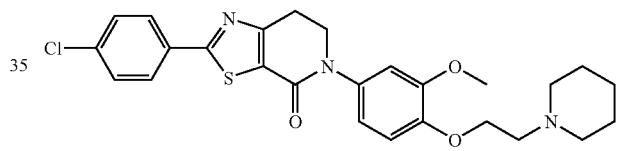

Exact mass=497.1, MS (ES+) 498.3 (M+1)+. $^1$H NMR (CDCl$_3$): δ 7.93 (d, J=8.7 Hz, 2H), 7.44 (d, J=8.7 Hz, 2H), 6.92 (m, 2H), 6.84 (m, 1H), 4.20 (t, J=5.5 Hz, 2H), 4.09 (t, J=6.9 Hz, 2H), 3.86 (s, 3H), 3.28 (t, J=7.0 Hz, 2H), 2.87 (br s, 2H), 2.58 (br s, 4H), 1.65 (br s, 4H), 1.47 (br s, 2H).

Example 16

2-(4-Chloro-phenyl)-5-[3-methoxy-4-(2-morpholin-4-yl-ethoxy)-phenyl]-6,7-dihydro-5H-thiazolo[5,4-c]pyridin-4-one

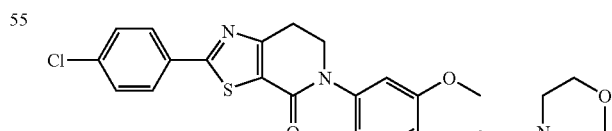

Exact mass=499.1, MS (ES+) 500.3 (M+1)+. $^1$H NMR (CDCl$_3$): δ 7.92 (d, J=8.4 Hz, 2H), 7.44 (d, J=8.4 Hz, 2H), 6.94-6.91 (m, 2H), 6.84 (dd, J=8.6, 2.6 Hz, 1H), 4.18 (t, J=5.8 Hz, 2H), 4.09 (t, J=7.0 Hz, 2H), 3.86 (s, 3H), 3.75 (m, 4H), 3.28 (t, J=7.0 Hz, 2H), 2.87 (ap t, 2H), 2.62 (br s, 4H).

Example 17

2-(4-Chloro-phenyl)-5-[4-(2-diethylamino-ethoxy)-3-methoxy-phenyl]-6,7-dihydro-5H-thiazolo[5,4-c]pyridin-4-one

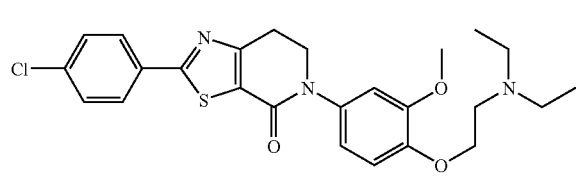

Exact mass=485.1, MS (ES+) 486.3 (M+1)+. $^1$H NMR (CDCl$_3$): δ 7.93 (d, J=8.6 Hz, 2H), 7.45 (d, J=8.6 Hz, 2H), 6.94-6.91 (m, 2H), 6.84 (dd, J=8.6, 2.4 Hz, 1H), 4.15-4.07 (m, 4H), 3.86 (s, 3H), 3.27 (t, J=6.9 Hz, 2H), 2.95 (ap d, 2H), 2.67 (ap t, 4H), 1.09 (t, J=7.1 Hz, 6H).

Example 18

2-(4-Chloro-phenyl)-5-{4-[2-(cyclohexyl-methyl-amino)-ethoxy]-3-methoxy-phenyl}-6,7-dihydro-5H-thiazolo[5,4-c]pyridin-4-one

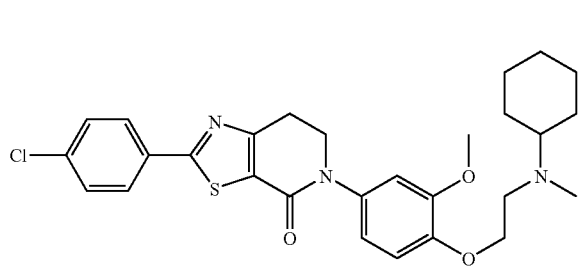

Exact mass=525.2, MS (ES+) 526.3 (M+1)+. $^1$H NMR (CDCl$_3$): δ 7.93 (d, J=8.6 Hz, 2H), 7.45 (d, J=8.6 Hz, 2H), 6.93-6.90 (m, 2H), 6.84 (dd, J=8.6, 2.4 Hz, 1H), 4.14-4.07 (m, 4H), 3.86 (s, 3H), 3.28 (t, J=7.0 Hz, 2H), 2.95 (ap t, 2H), 2.45 (br s, 1H), 2.40 (s, 3H), 1.90-1.77 (m, 4H), 1.64 (br s, 2H), 1.29-1.20 (m, 4H).

Example 19

2-(4-Chloro-phenyl)-5-{3-methoxy-4-[2-(4-methyl-piperazin-1-yl)-ethoxy]-phenyl}-6,7-dihydro-5H-thiazolo[5,4-c]pyridin-4-one

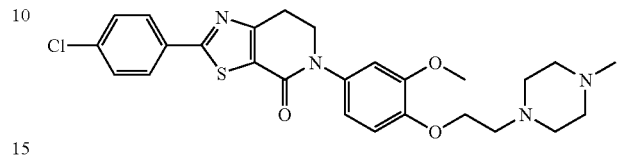

Exact mass=512.2, MS (ES+) 513.3 (M+1)+. $^1$H NMR (CDCl$_3$): δ 7.92 (d, J=8.7 Hz, 2H), 7.44 (d, J=8.7 Hz, 2H), 6.93-6.89 (m, 2H), 6.83 (dd, J=8.6, 2.3 Hz, 1H), 4.16 (t, J=6.2 Hz, 2H), 4.09 (t, J=7.0 Hz, 2H), 3.85 (s, 3H), 3.28 (t, J=7.0 Hz, 2H), 2.86 (t, J=6.2 Hz, 2H), 2.64 (br s, 4H), 2.50 (br s, 4H), 2.30 (s, 3H).

Example 20

2-(4-Chloro-phenyl)-5-{4-[2-(isopropyl-methyl-amino)-ethoxy]-3-methoxy-phenyl}-6,7-dihydro-5H-thiazolo[5,4-c]pyridin-4-one

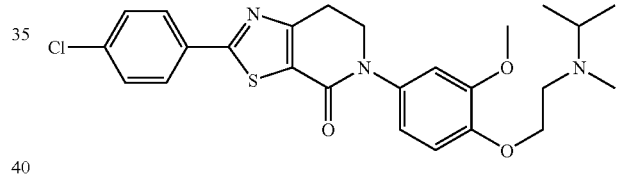

Exact mass=485.2, MS (ES+) 486.3 (M+1)+. $^1$H NMR (CDCl$_3$): δ 7.93 (d, J=8.5 Hz, 2H), 7.45 (d, J=8.5 Hz, 2H), 6.94-6.91 (m, 2H), 6.84 (dd, J=8.4, 2.5 Hz, 1H), 4.15-4.07 (m, 4H), 3.86 (s, 3H), 3.28 (t, J=7.0 2H), 2.94-2.85 (m, 3H), 2.35 (br s, 3H), 1.05 (d, J=6.5 Hz, 6H).

Example 21

5-[4-(2-[1,4']Bipiperidinyl-1'-yl-ethoxy)-3-methoxy-phenyl]-2-(4-chloro-phenyl)-6,7-dihydro-5H-thiazolo[5,4-c]pyridin-4-one

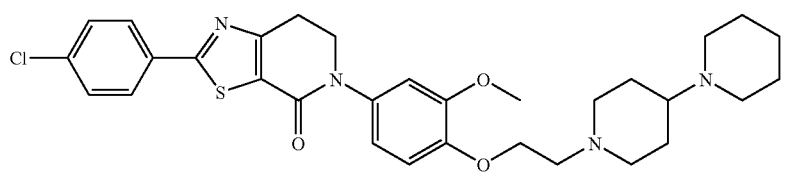

Exact mass=580.2, MS (ES+) 581.4 (M+1)+. 1H NMR (CDCl3): δ 7.93 (d, J=8.6 Hz, 2H), 7.45 (d, J=8.6 Hz, 2H), 6.94-6.91 (m, 2H), 6.84 (dd, J=8.5, 2.5 Hz, 1H), 4.15 (t, J=6.4 Hz, 2H), 4.09 (t, J=7.0 Hz, 2H), 3.86 (s, 3H), 3.28 (t, J=7.0 Hz, 2H), 3.06 (d, J=5.7 Hz, 2H), 2.83 (t, J=6.4 Hz, 2H), 2.52 (br s, 4H), 2.12 (t, J=11.7 Hz, 2H), 1.80 (ap d, 2H), 1.70-1.52 (m, 7H), 1.43 (br s, 2H).

| Ex | Product (Chemical Name) | Structure | Physical Data |
|---|---|---|---|
| 22 | 2-Phenyl-5-[4-(2-pyrrolidin-1-yl-ethoxy)-phenyl]-6,7-dihydro-5H-thiazolo[5,4-c]pyridin-4-one | 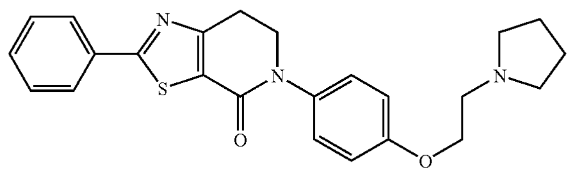 | MS (ES+) 420.2 (M + 1)+. |
| 23 | 2-(4-Methoxy-phenyl)-5-[3-methoxy-4-(2-pyrrolidin-1-yl-ethoxy)-phenyl]-6,7-dihydro-5H-thiazolo[5,4-c]pyridin-4-one | 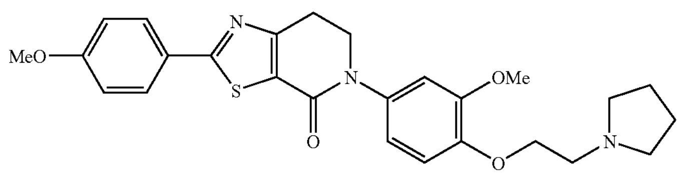 | MS (ES+) 480.2 (M + 1)+. |
| 24 | 2-(3-Chloro-phenyl)-5-[3-methoxy-4-(2-pyrrolidin-1-yl-ethoxy)-phenyl]-6,7-dihydro-5H-thiazolo[5,4-c]pyridin-4-one | 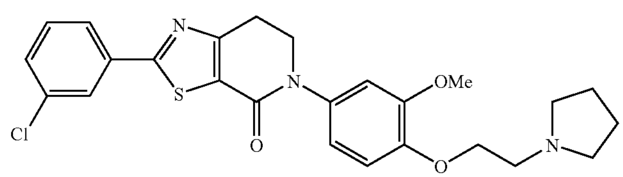 | MS (ES+) 484.2 (M + 1)+. |
| 25 | 5-[3-Methoxy-4-(2-pyrrolidin-1-yl-ethoxy)-phenyl]-2-(4-trifluoromethyl-phenyl)-6,7-dihydro-5H-thiazolo[5,4-c]pyridin-4-one | 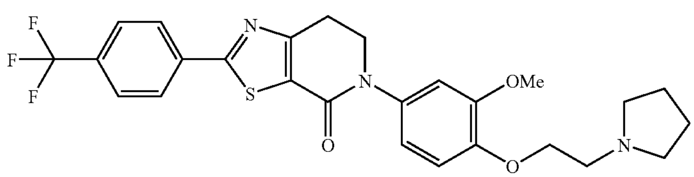 | MS (ES+) 518.2 (M + 1)+. |
| 26 | 2-(2,4-Dichloro-phenyl)-5-[3-methoxy-4-(2-pyrrolidin-1-yl-ethoxy)-phenyl]-6,7-dihydro-5H-thiazolo[5,4-c]pyridin-4-one | 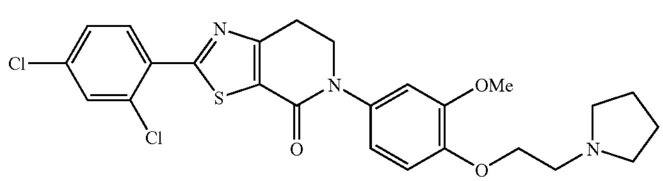 | MS (ES+) 518.2 (M + 1)+. |
| 27 | 2-(4-Fluoro-phenyl)-5-[3-methoxy-4-(2-pyrrolidin-1-yl-ethoxy)-phenyl]-6,7-dihydro-5H-thiazolo[5,4-c]pyridin-4-one | 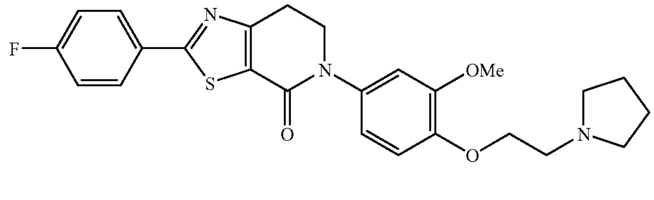 | MS (ES+) 468.2 (M + 1)+. |

-continued

| Ex | Product (Chemical Name) | Structure | Physical Data |
|---|---|---|---|
| 28 | 5-[3-Methoxy-4-(2-morpholin-4-yl-ethoxy)-phenyl]-2-(4-methoxy-phenyl)-6,7-dihydro-5H-thiazolo[5,4-c]pyridin-4-one | 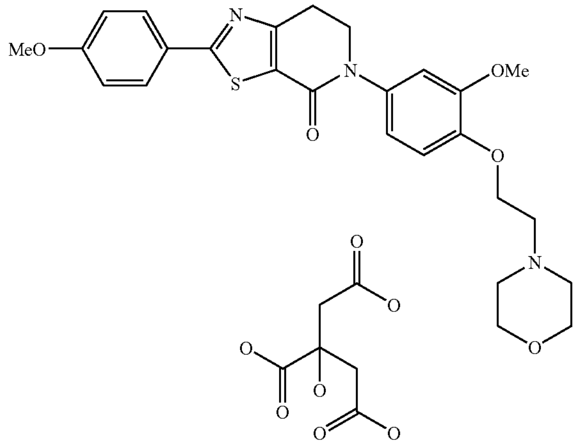 | MS (ES+) 496.0 (M + 1)+. |
| 29 | 5-[4-(2-Dimethylamino-ethoxy)-3-methoxy-phenyl]-2-(4-methoxy-phenyl)-6,7-dihydro-5H-thiazolo[5,4-c]pyridin-4-one | 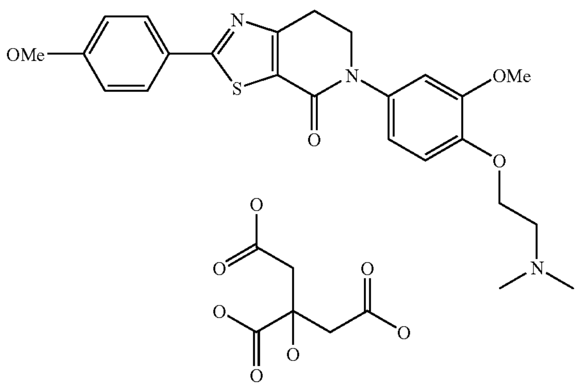 | MS (ES+) 454.0 (M + 1)+. |

Preparation 118

2,2-Dimethyl-propionic acid 2-methoxy-4-[2-(4-methoxy-phenyl)-4-oxo-6,7-dihydro-4H-thiazolo[5,4-c]pyridin-5-yl]-phenyl ester

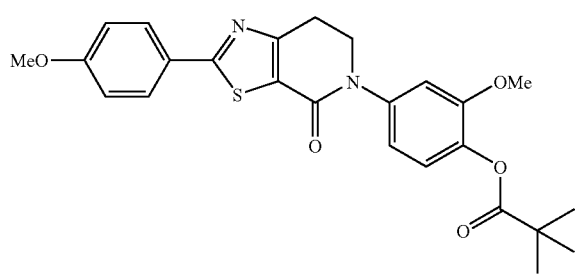

Dissolve 2,2-dimethyl-propionic acid 4-{[4-(2-hydroxy-ethyl)-2-(4-methoxy-phenyl)-thiazole-5-carbonyl]-amino}-2-methoxy-phenyl ester (480 mg, 0.98 mmol) and NEt$_3$ (177 mL, 1.27 mmol) in dry CH$_2$Cl$_2$ and cool to 0° C. Add dropwise methanesulfonyl chloride (98.1 mL, 1.27 mmol) and stir for 30 min. Quench the reaction mixture with saturated NH$_4$Cl solution and extract with CH$_2$Cl$_2$ (3×10 mL). Dry, filter, and concentrate. Redissolve the crude material in dry DMF (6.5 mL) and chill to 0° C. Add portionwise NaH (60% dispersion, 51 mg, 1.27 mmol) then warm to ambient temperature overnight. Add 1N HCl (20 mL) and extract with EtOAc (3×10 mL). Collect insoluble solid from portioned layers via filtration. Wash the filtrate with water (40 mL), dry, filter, and concentrate. Combine the resulting material with the collected solid to give the title compound as a yellow solid (749 mg, 99%). MS (ES+) 467.3 (M+1)+. $^1$H NMR (400 MHz, CD$_3$OD): δ 7.96 (d, 2H, J=8.4 Hz), 7.14 (d, 1H, J=2.2 Hz), 7.05 (d, 2H, J=8.4 Hz), 7.04 (dd, 1H, J=8.8, 2.2 Hz), 6.96 (dd, 1H, J=8.4, 2.2 Hz), 4.15 (t, 2H, J=7.0 Hz), 3.87 (s, 3H), 3.81 (s, 3H), 3.27 (t, 2H, J=7.5 Hz), 1.35 (s, 9H).

Preparation 119

5-(4-Hydroxy-3-methoxy-phenyl)-2-(4-methoxy-phenyl)-6,7-dihydro-5H-thiazolo[5,4-c]pyridin-4-one

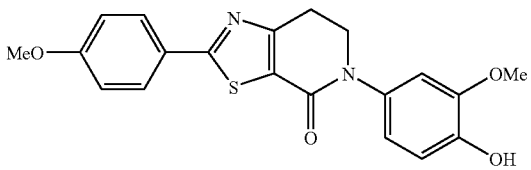

Dissolve 2,2-dimethyl-propionic acid 2-methoxy-4-[2-(4-methoxy-phenyl)-4-oxo-6,7-dihydro-4H-thiazolo[5,4-c]pyridin-5-yl]-phenyl ester (749 mg, 1.61 mmol) in absolute ethanol (18 mL) and add NaOMe (183.1 mg, 6.44 mmol). Allow the reaction mixture to stir for 4 h at ambient temperature. Quench the reaction mixture with 1N HCl solution. to pH=7. Add a small amount of EtOAc (15 mL) and filter the solid precipitate via vacuum filtration to give the title compound as a yellow solid (430 mg, 70%). MS (ES+) 383.3 (M+1)+. $^1$H NMR (CDCl$_3$): δ 7.95 (d, J=8.8 Hz, 2H), 6.98 (d, J=8.8 Hz, 2H), 6.94 (d, J=6.2 Hz, 1H), 6.93 (s, 1H), 6.80 (dd, J=8.8, 2.2 Hz, 1H), 4.07 (t, J=7.0. Hz, 2H), 3.90 (s, 3H), 3.87 (s, 3H), 3.28 (t, J=7.0 Hz, 2H).

Preparation 120

2-(4-Chloro-phenyl)-6,7-dihydro-5H-thiazolo[5,4-c]pyridin-4-one

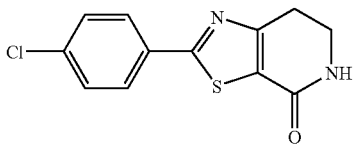

Dissolve 2-(4-chloro-phenyl)-5-(3,4-dimethoxy-benzyl)-6,7-dihydro-5H-thiazolo[5,4-c]pyridin-4-one (376 mg, 0.91 mmol) in toluene (5.0 mL) and treat with para-toluene sulfonic acid (176 mg, 0.92 mmol). Stir the solution at reflux for 2 d, then concentrate and purify the crude material by flash chromatography, using 5% MeOH (2N NH$_3$)/CH$_2$Cl$_2$ as eluent, to give the title compound as a white solid (170 mg, 70%). MS (ES+) 265.0 (M+1)+. $^1$H NMR (CDCl$_3$): δ 8.02 (d, 2H, J=8.8 Hz), 7.94 (s, 1H), 7.60 (d, 2H, J=8.4 Hz), 3.52 (dt, 2H, J=7.1, 2.5 Hz), 3.04 (t, 2H, J=7.3 Hz).

Preparation 121

Toluene-4-sulfonic acid 4-[2-(4-chloro-phenyl)-4-oxo-6,7-dihydro-4H-thiazolo[5,4-c]pyridin-5-yl]-2-methoxy-phenyl ester

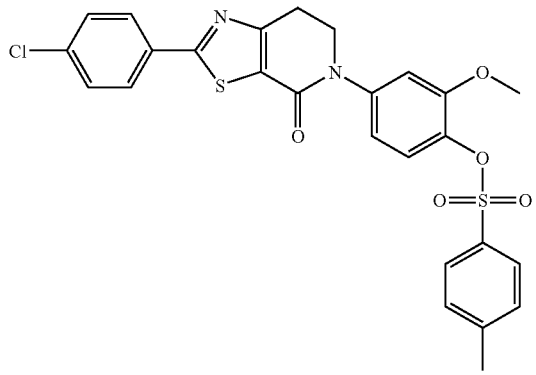

Mix 2-(4-chloro-phenyl)-6,7-dihydro-5H-thiazolo[5,4-c]pyridin-4-one (128 mg, 0.48 mmol), toluene-4-sulfonic acid 4-bromo-2-methoxy-phenyl ester (218 mg, 0.61 mmol), 4,5-bis(diphenylphosphino)-9,9-dimethylxanthene (17.2 mg, 0.030 mmol), Cs$_2$CO$_3$ (0.123 mg, 0.377 mmol) in dioxane (13 mL). Purge the solution with nitrogen for 30 min and then add tris(dibenzylideneacetone)dipalladium(0) (Pd$_2$(dba)$_3$) (6.7 mg, 0.0073 mmol). Stir the mixture at reflux overnight, then cool to room temperature. Dilute the mixture with EtOAc (50 mL) and wash with water (2×30 mL) and brine (30 mL). Dry, filter and concentrate the organic solution and purify the residue by flash chromatography, using a linear gradient of 100% hexanes to 80% EtoAc/hexanes as eluent, to give the title compound as a light brown solid (155 mg, 60%). MS (ES+) 541.0 (M+1)+. $^1$H NMR (CDCl$_3$): δ 7.92 (d, 2H, J=8.4 Hz), 7.78 (d, 2H, J=8.4 Hz), 7.44 (d, 2H, J=8.8 Hz), 7.31 (d, 2H, J=8.4 Hz), 7.17 (d, 1H, J=8.8 Hz), 6.96 (d, 1H, J=2.6 Hz), 6.82 (dd, 1H, J=8.6, 2.4 Hz), 4.11 (t, 2H, J=6.8 Hz), 3.57 (s, 3H), 3.28 (t, 2H, J=6.8 Hz), 2.44 (s, 3H).

Preparation 122

2-(4-Chloro-phenyl)-5-(4-hydroxy-3-methoxy-phenyl)-6,7-dihydro-5H-thiazolo[5,4-c]pyridin-4-one

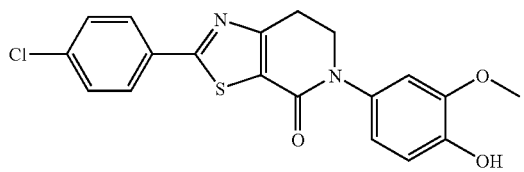

Method 1. Mix toluene-sulfonic acid 4-[2-(4-chloro-phenyl)-4-oxo-6,7-dihydro-4H-thiazolo[5,4-c]pyridin-5-yl]-2-methoxy-phenyl ester (110 mg, 0.20 mmol) in dioxane (mL) and water (mL) and treat with LiOH.H$_2$O (44 mg, 1.0 mmol). Stir the mixture at reflux for 3 h, cool to room temperature, neutralize with 1N HCl (1.0 mL), and dilute with additional water. Collect the solid by filtration and purify by flash chromatography, using a 5% MeOH (2N NH$_3$)/CH$_2$Cl$_2$ as eluent, to give the title compound as an off-white solid (29 mg, 37%).

MS (ES+) 387.0 (M+1)+, MS (ES−) 385.0 (M−1)−. ¹H NMR (CDCl₃): δ 7.92 (d, 2H, J=8.4 Hz), 7.44 (d, 2H, J=8.4 Hz), 6.95-6.92 (m, 2H), 6.80 (dd, 1H, J=8.6, 2.4 Hz), 5.61 (s, 1H), 4.08 (t, 2H, J=7.0 Hz), 3.90 (s, 3H), 3.28 (t, 2H, J=7.0 Hz).

Method 2. Combine 5-[4-(tert-butyl-dimethyl-silanyloxy)-3-methoxy-phenyl]-2-(4-chloro-phenyl)-6,7-dihydro-5H-thiazolo[5,4-c]pyridin-4-one (0.92 g, 1.84 mmol), THF (10 mL), and tetrabutylammonium fluoride (1M in THF, 2.0 mL, 2.0 mmol and stir at room temperature overnight. Neutralize with saturated aqueous NH₄Cl, extract with diethyl ether (1×), EtOAc (2×), dry over MgSO₄, filter, and concentrate under vacuum. Purify by flash chromatography on silica gel, eluting with a gradient of EtOAc/hexane 20%-45% to give the title compound as a yellow residue (0.28 g, 40%). Exact mass=386.0, MS (ES+) 387.1 (M+1)+.

Preparation 123

(R)-2-(4-Chloro-phenyl)-5-[3-methoxy-4-(3-triisopropylsilanyloxy-pyrrolidin-1-yl)-phenyl]-6,7-dihydro-5H-thiazolo[5,4-c]pyridin-4-one

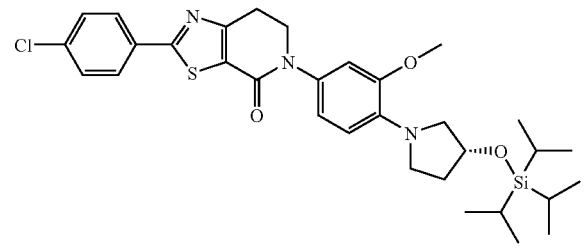

Prepare the title compound by essentially following the procedures as described for Preparation 118, with the following alternate workup. Quench the reaction mixture with saturated NH₄Cl solution (10 mL) and extract with EtOAc (3×20 mL). Wash the organic layer with water (2×20 mL). Dry the organic layer with Na₂SO₄, filter, and concentrate. Purify on silica gel chromatography using 0-25% EtOAc in hexanes to give the title compound. MS (ES+) 612.1 (M+1)+. ¹H NMR (CDCl₃): δ 7.90 (d, J=8.4 Hz, 2H), 7.42 (d, J=8.8 Hz, 2H), 6.85 (bs, 1H), 6.80 (dd, J=8.4, 2.2 Hz, 1H), 6.75-6.68 (m, 1H), 4.57 (bs, 1H), 4.06 (t, J=7.0 Hz, 2H), 3.81 (s, 3H), 3.72-3.63 (m, 1H), 3.43-3.29 (m, 2H), 3.25 (t, J=7.0 Hz, 2H), 3.17-3.09 (m, 1H), 2.20-2.06 (m, 1H), 1.96-1.86 (m, 1H), 1.12-0.98 (m, 21H).

Preparation 124

5-Chloromethyl-1-methyl-1H-imidazole

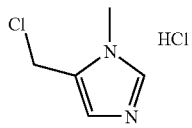

Add thionyl chloride (4.00 ml, 53.8 mmol) to a solution of (3-methyl-3H-imidazol-4-yl)-methanol (4.0 g, 35.7 mmol) in dichloroethane (30 mL) and stir at room temperature for 18 h. Concentrate the reaction mixture and add ether to the residue. Sonicate for 5 min, filter, and dry to give the title compound (5.8 g, 98%). MS (ES+) 131 (M+1)+. ¹H NMR (400 MHz, DMSO-d6): δ 14.99 (s, 1H), 9.18 (s, 1H), 7.75 (s, 1H), 5.00 (s, 2H), 3.85 (s, 3H).

Preparation 125

4-chloromethyl-1H-imidazole

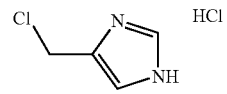

Prepare the title compound by essentially following the procedure as described for Preparation 124, using (3H-imidazol-4-yl)-methanol. MS (ES+) 117.1 (M+1)+. ¹H NMR (400 MHz, DMSO-d6): δ 15.03 (s, 1H), 9.12 (d, 1H, J=1.3 Hz), 7.71 (d, 1H, J=1.3 Hz), 4.85 (s, 2H)

General Procedure 2

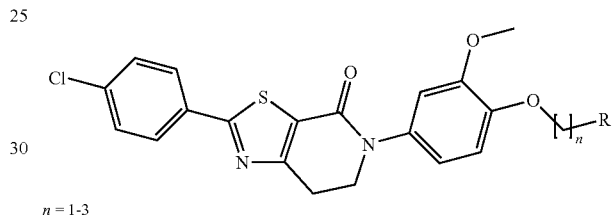

n = 1-3

To a vial containing 2-(4-chloro-phenyl)-5-(4-hydroxy-3-methoxy-phenyl)-6,7-dihydro-5H-thiazolo[5,4-c]pyridin-4-one (0.050 g, 0.13 mmol) add DMF (1 mL), K₂CO₃ (3 molar equivalents), potassium iodide (catalytic), and an alkyl halide (1.2 molar equivalents). Stir overnight at room temperature. If reaction is not complete, heat in a microwave reactor at 100° C. for 10 min, or heat in a 100° C. oil bath until the phenol starting material is consumed. Add water, extract with EtOAc (3×), dry by elution through a Na₂SO₄ drying tube and concentrate under vacuum. Purify by flash chromatography on silica gel to give the title compound.

Prepare Examples 30 to 36 as essentially described according to the general procedure, above, using the appropriate alkyl halide reagent.

Example 30

2-(4-Chloro-phenyl)-5-[4-(3-dimethylamino-propoxy)-3-methoxy-phenyl]-6,7-dihydro-5H-thiazolo[5,4-c]pyridine-4-one

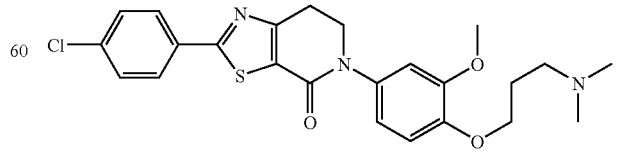

Exact mass=471.1, MS (ES+) 472.3 (M+1)+. ¹H NMR (CDCl₃): δ7.93 (d, J=8.6 Hz, 2H), 7.45 (d, J=8.6 Hz, 2H), 6.94-6.91 (m, 2H), 6.84 (dd, J=8.5, 2.4 Hz, 1H), 4.12-4.07 (m, 4H), 3.87 (s, 3H), 3.29 (t, J=6.9 Hz, 2H), 2.57 (br s, 2H), 2.34 (br s, 6H), 2.07 (m, 2H).

Example 31

2-(4-Chloro-phenyl)-5-[3-methoxy-4-(3-piperidin-1-yl-propoxy)-phenyl]-6,7-dihydro-5H-thiazolo[5,4-c]pyridin-4-one

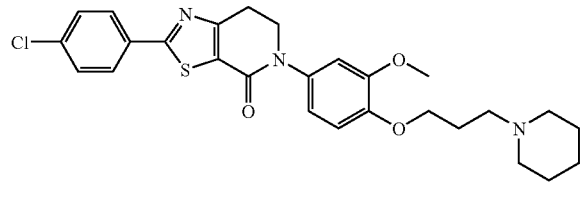

Exact mass=511.2, MS (ES+) 512.3 (M+1)+. 1H NMR (CDCl3): δ 7.93 (d, J=8.6 Hz, 2H), 7.44 (d, J=8.6 Hz, 2H), 6.94-6.91 (m, 2H), 6.84 (dd, J=8.7, 2.3 Hz, 1H), 4.11-4.06 (m, 4H), 3.86 (s, 3H), 3.28 (t, J=7.0 Hz, 2H), 2.53 (br s, 2H), 2.45 (br s, 4H), 2.06 (m, 2H), 1.62 (br s, 4H), 1.45 (br s, 2H).

Example 32

2-(4-Chloro-phenyl)-5-[4-(3-diethylamino-propoxy)-3-methoxy-phenyl]-6,7-dihydro-5H-thiazolo[5,4-c]pyridin-4-one

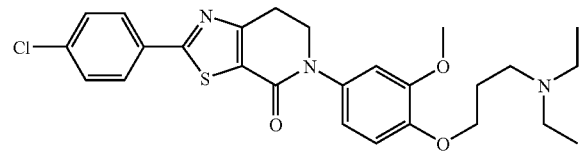

Exact mass=499.2, MS (ES+) 500.3 (M+1)+. 1H NMR (CDCl3): δ 7.93 (d, J=8.4 Hz, 2H), 7.44 (d, J=8.4 Hz, 2H), 6.94-6.91 (m, 2H), 6.84 (dd, J=8.5, 2.5 Hz, 1H), 4.11-4.06 (m, 4H), 3.86 (s, 3H), 3.28 (t, J=7.0 Hz, 2H), 2.61 (t, J=7.2 Hz, 2H), 2.54 (t, J=7.2 Hz, 4H), 2.02-1.94 (m, 2H), 1.02 (t, J=7.2 Hz, 6H).

Example 33

2-(4-Chloro-phenyl)-5-[4-(2-dimethylamino-ethoxy)-3-methoxy-phenyl]-6,7-dihydro-5H-thiazolo[5,4-c]pyridin-4-one

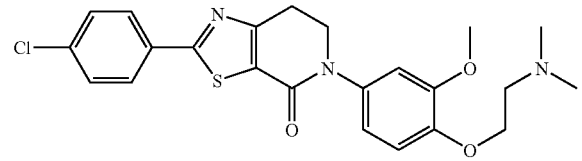

Exact mass=457.1, MS (ES+) 458.2 (M+1)+. 1H NMR (CDCl3): δ7.93 (d, J=8.5 Hz, 2H), 7.45 (d, J=8.5 Hz, 2H), 6.94-6.91 (m, 2H), 6.84 (dd, J=8.5, 2.5 Hz, 1H), 4.13 (t, J=6.1 Hz, 2H), 4.09 (t, J=7.0 Hz, 2H), 3.86 (s, 3H), 3.28 (t, J=7.0 Hz, 2H), 2.79 (t, J=6.1 Hz, 2H), 2.35 (s, 6H).

Example 34

2-(4-Chloro-phenyl)-5-[3-methoxy-4-(pyridin-4-ylmethoxy)-phenyl]-6,7-dihydro-5H-thiazolo[5,4-c]pyridin-4-one

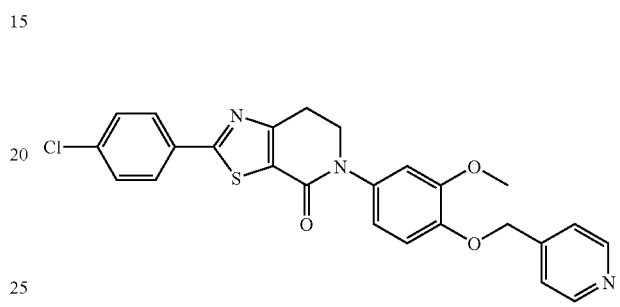

Exact mass=477.1, MS (ES+) 478.2 (M+1)+. 1H NMR (CDCl3): δ 8.64 (br s, 2H), 7.93 (d, J=8.5 Hz, 2H), 7.49 (ap d, 2H), 7.45 (d, J=8.5 Hz, 2H), 7.00 (d, J=2.5 Hz, 1H), 6.86 (d, J=8.5 Hz, 1H), 6.81 (dd, J=8.5, 2.2 Hz, 1H), 5.21 (s, 2H), 4.09 (t, J=7.0 Hz, 2H), 3.91 (s, 3H), 3.29 (t, J=7.0 Hz, 2H).

Example 35

2-(4-Chloro-phenyl)-5-[3-methoxy-4-(1-methyl-1H-imidazol-2-ylmethoxy)-phenyl]-6,7-dihydro-5H-thiazolo[5,4-c]pyridin-4-one

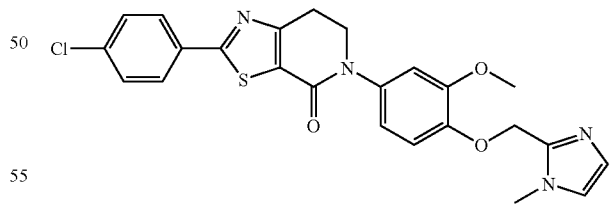

Exact mass=480.1, MS (ES+) 481.2 (M+1)+. 1H NMR (CDCl3): δ 7.92 (dt, J=8.4, 2.2 Hz, 2H), 7.44 (dt, J=8.7, 2.2 Hz, 2H), 7.18 (d, J=8.7 Hz, 1H), 7.00 (s, 1H), 6.95 (d, J=2.5 Hz, 1H), 6.89 (s, 1H), 6.81 (dd, J=8.4, 2.5 Hz, 1H), 5.26 (s, 2H), 4.08 (t, J=7.0 Hz, 2H), 3.86 (s, 3H), 3.79 (s, 3H), 3.28 (t, J=7.0 Hz, 2H).

Example 36

2-(4-Chloro-phenyl)-5-[3-methoxy-4-(2-methyl-thiazol-5-ylmethoxy)-phenyl]-6,7-dihydro-5H-thiazolo[5,4-c]pyridin-4-one

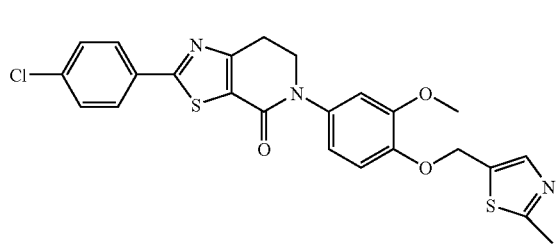

Exact mass=497.1, MS (ES+) 498.2 (M+1)+. 1H NMR (CDCl3): δ 7.93 (dt, J=8.7, 2.2 Hz, 2H), 7.45 (dt, J=8.7, 2.2 Hz, 2H), 7.19 (ap s, 1H), 6.99-6.95 (m, 2H), 6.81 (dd, J=8.7, 2.2 Hz, 1H), 5.25 (ap d, 2H), 4.09 (t, J=7.0 Hz, 2H), 3.89 (s, 3H), 3.28 (t, J=7.0 Hz, 2H), 2.73 (s, 3H).

Example 37

2-(4-Chloro-phenyl)-5-[3-methoxy-4-(morpholin-2-ylmethoxy)-phenyl]-6,7-dihydro-5H-thiazolo[5,4-c]pyridin-4-one

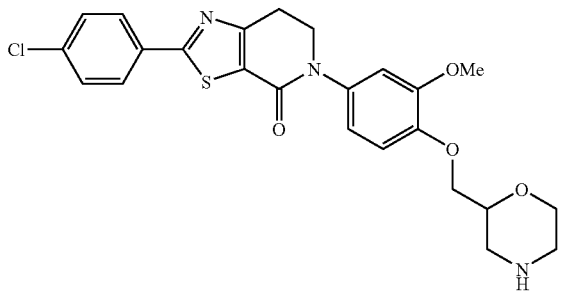

Dissolve 2-(4-chloro-phenyl)-5-(4-hydroxy-3-methoxy-phenyl)-6,7-dihydro-5H-thiazolo[5,4-c]pyridin-4-one (103 mg, 0.267 mmol), 2-hydroxymethyl-morpholine-4-carboxylic acid tert-butyl ester (Pharmacore, CAS: 135065-69-9) (70 mg, 0.324 mmol), and PBu3 (84 μl, 0.324 mmol) in dry toluene (1.2 mL). Cool to 0° C. then add 1,1'-(azodicarbonyl) piperidine (84 μl, 0.324 mmol). Let stir for 10 min at 0° C., then warm to ambient temperature overnight. Reaction mixture thickens and turns gel like. Add hexanes and collect solid via vacuum filtration. Wash the solid with hexanes several times. Dissolve the crude material in dry CH2Cl2 (500 μL) and TFA (200 μl) and stir overnight. Add 1N NaOH until the reaction is pH=10 and extract with EtOAc (3×10 mL). Dry the combined organic portions with Na2SO4, filter, and concentrate to give the title compound. MS (ES+) 486.0 (M+1)+.

Example 38

2-(4-Chloro-phenyl)-5-[3-methoxy-4-(4-methyl-morpholin-2-ylmethoxy)-phenyl]-6,7-dihydro-5H-thiazolo[5,4-c]pyridin-4-one, hydrochloride salt

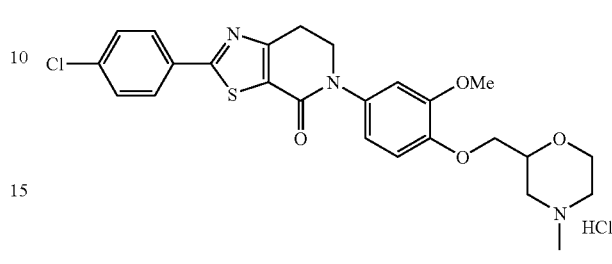

Dissolve 2-(4-chloro-phenyl)-5-[3-methoxy-4-(morpholin-2-ylmethoxy)-phenyl]-6,7-dihydro-5H-thiazolo[5,4-c]pyridin-4-one (460 mg, 0.928 mmol) in dry acetone (3 mL) under nitrogen. Add K2CO3 (321 mg, 1.11 mmol) and NaI (14 mg, 0.092 mmol). Evacuate under vacuum and charge the reaction mixture with nitrogen. Mix well and then add MeI (70 mL, 1.11 mmol). Stir the reaction mixture overnight. Add saturated NH4Cl solution (5 mL) and extract with EtOAc (3×10 mL). Wash the combined organic layers with water (10 mL), dry with Na2SO4, filter, and concentrate. Purify the resulting residue with silica gel chromatography, using 0-10% MeOH/CHCl3 to give the title compound. Dissolve the compound in minimal CH2Cl2 and add HCl/Et2O to make the HCl salt as a yellow-orange solid (74 mg, 15%). MS (ES+) 500.0 (M+1)+.

Example 39

(R)-2-(4-Chloro-phenyl)-5-[4-(3-hydroxy-pyrrolidin-1-yl)-3-methoxy-phenyl]-6,7-dihydro-5H-thiazolo[5,4-c]pyridin-4-one, hydrochloride salt

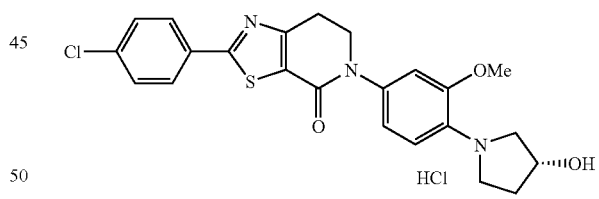

Dissolve (R)-2-(4-chloro-phenyl)-5-[3-methoxy-4-(3-triisopropylsilanyloxy-pyrrolidin-1-yl)-phenyl]-6,7-dihydro-5H-thiazolo[5,4-c]pyridin-4-one (370 mg, 0.610 mmol) in dry THF (2 mL). Add TBAF (1.0M in THF, 610 μl, 0.610 mmol) and stir 2 h. Absorb the reaction mixture on silica gel and remove organic solvent via reduce pressure. Purify by silica gel chromatography using 0-100% EtOAc in hexanes to give the title compound. Dissolve the compound in a minimal amount of CH2Cl2 and add HCl/Et2O solution to give precipitated product. Remove the organic solvent via reduced pressure and triturate with MeOH to give the desired product as white solid HCl salt (144 mg, 48%). MS (ES+) 456.0 (M+1)+. 1H NMR (CD3OD): δ 8.01 (d, J=8.8 Hz, 2H), 7.71 (br d, J=8.8 Hz, 1H), 7.51 (d, J=8.4 Hz, 2H), 7.35 (br s, 1H), 7.16 (br d, J=8.8 Hz, 1H), 4.73-4.67 (m, 1H), 4.19 (br t, J=6.6

Hz, 2H), 4.02 (br s, 3H), 3.97-3.85 (m, 3H), 3.66 (br d, J=11.0 Hz, 1H), 3.31 (t, J=7.0 Hz, 2H), 2.49-2.36 (m, 1H), 2.26-2.17 (m, 1H).

Preparation 126

2-(4-Chloro-phenyl)-5-(3-methoxy-4-triisopropylsilanyloxy-phenyl)-5H-thiazolo[5,4-c]pyridin-4-one

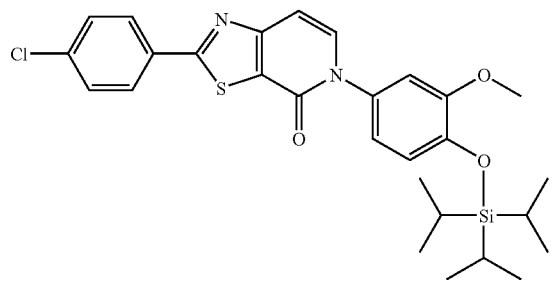

Treat a solution 2-(4-chloro-phenyl)-4-(2-hydroxy-ethyl)-thiazole-5-carboxylic acid (3-methoxy-4-triisopropylsilanyloxy-phenyl)-amide (1.0 g, 1.79 mmol) in $CH_2Cl_2$ (30 mL) with Dess-Martin periodinane (1.13 g, 2.67 mmol). Stir at room temperature for 18 h, dilute with 1N NaOH, and extract with $CH_2Cl_2$ (2×). Dry, filter, and concentrate the organic solution and purify the crude material by flash chromatography, using a gradient of 0-10% MeOH in $CH_2Cl_2$ to give the title compound (0.47 g, 48%). MS (ES+) 541.0 (M+1)+. $^1$H NMR (400 MHz, $CDCl_3$) δ: 8.01 (d, 2H, J=8.8 Hz), 7.46 (d, 2H, J=8.4 Hz), 7.41 (d, 1H, J=7.5 Hz), 6.93 (m, 3H), 6.81 (dd, 1H, J=8.4, 2.6 Hz), 3.80 (s, 3H), 1.25 (m, 3H), 1.09 (d, 18H, J=7.5 Hz).

Preparation 127

2-(4-Chloro-phenyl)-5-(4-hydroxy-3-methoxy-phenyl)-5H-thiazolo[5,4-c]pyridin-4-one

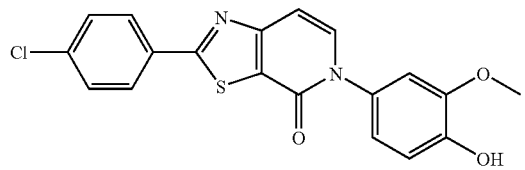

Treat a solution of 2-(4-chloro-phenyl)-5-(3-methoxy-4-triisopropylsilanyloxy-phenyl)-5H-thiazolo[5,4-c]pyridin-4-one (0.47 g, 0.87 mmol) in THF (5.0 mL) with TBAF (1.3 mL of 1N in THF) and stir for 4 h. Acidify reaction mixture to pH 4 with 1N HCl. Filter precipitate, wash several times with water, and dry to give title compound (0.23 g, 69%). MS (ES+) 385 (M+1)+. $^1$H NMR (400 MHz, DMSO-d6) δ 9.33 (s, 1H), 8.11 (d, 2H, J=8.4 Hz), 7.69 (d, 1H, J=7.0 Hz), 7.62 (d, 2H, J=8.8 Hz), 7.02-6.97 (m, 2H), 6.86-6.81 (m, 2H), 3.74 (s, 3H).

Example 40

2-(4-Chloro-phenyl)-5-[3-methoxy-4-(2-pyrrolidin-1-yl-ethoxy)-phenyl]-5H-thiazolo[5,4-c]pyridin-4-one

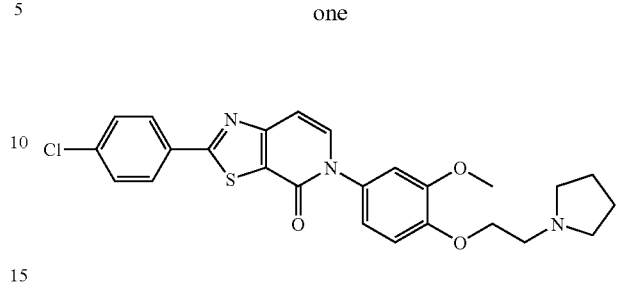

Mix 2-(4-chloro-phenyl)-4-(2-hydroxy-ethyl)-thiazole-5-carboxylic acid [3-methoxy-4-(2-pyrrolidin-1-yl-ethoxy)-phenyl]-amide (80 mg, 0.16 mmol) and Dess-Martin periodinane (70 mg, 0.16 mmol) in $CH_2Cl_2$ and stir at RT for 48 h. Dilute the mixture with aqueous 1 N NaOH and extract with $CH_2Cl_2$. Dry, filter, and concentrate the organic solution. Purify the crude material by flash chromatography, using a gradient of 100% EtOAc to 12% 2 N $NH_3$/MeOH in EtOAc, to give the title compound (12 mg, 16%). MS (ES+) 482.0 (M+1)+. $^1$H NMR (400 MHz, DMSO-d6): δ 8.01 (d, 2H, J=8.8 Hz), 7.46 (d, 2H, J=8.3 Hz), 7.40 (d, 1H, J=7.0 Hz), 7.34 (s, 1H), 6.89-6.99 (m, 3H), 4.20 (t, 2H, J=6.4 Hz), 3.86 (s, 3H), 2.96 (t, 2H, J=6.4 Hz), 2.64 (s, 4H), 1.80 (m, 4H).

Example 41

2-(4-Chloro-phenyl)-5-[3-methoxy-4-(2-pyrrolidin-1-yl-ethoxy)-phenyl]-5H-thiazolo[5,4-c]pyridin-4-one hydrochloride

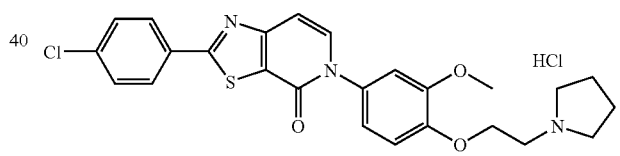

Add NaH (0.7 g, 17.5 mmol) to a solution of 2-(4-chloro-phenyl)-5-(4-hydroxy-3-methoxy-phenyl)-5H-thiazolo[5,4-c]pyridin-4-one (1.6 g, 4.2 mmol) in DMF (15 mL) at room temperature. Stir for 10-30 min, add 1-(2-chloro-ethyl)-pyrrolidine hydrochloride (2.1 g, 12.4 mmol), and warm to 90° C. for 1-2 days. Cool the reaction mixture, dilute with water, and extract with $CH_2Cl_2$ (2×). Combine the organic portions, dry, and concentrate. Purify by flash chromatography, using 0-10% 2N NH3/MeOH in $CH_2Cl_2$, to give the free amine. Dissolve the free amine in MeOH (10.0 mL) and add 1N HCl in ether (10.0 mL), sonicate for 5 min, and concentrate. Triturate the solid with ether, filter the solid, and dry to give the title compound (0.97 g, 45%). MS (ES+) 481.8 (M+1)+; free amine)+. $^1$H NMR (400 MHz, DMSO-δ6): δ 10.76 (s, 1H, HCl), 8.11 (d, 2H, J=8.8 Hz), 7.72 (d, 1H, J=7.0 Hz), 7.63 (d, 2H, J=8.4 Hz), 7.17-7.14 (m, 2H), 7.03-6.99 (m, 2H), 4.37 (t, 2H, J=5.1 Hz), 3.77 (s, 3H), 3.61 (m, 4H), 3.10 (m, 2H), 1.99 (m, 2H), 1.86 (m, 2H).

Prepare Example 42 to 44 by essentially following the procedures as described for Example 41, using the appropriate alkylating agent.

Example 42

2-(4-Chloro-phenyl)-5-[3-methoxy-4-(3-methyl-3H-imidazol-4-ylmethoxy)-phenyl]-6,7-dihydro-5H-thiazolo[5,4-c]pyridin-4-one

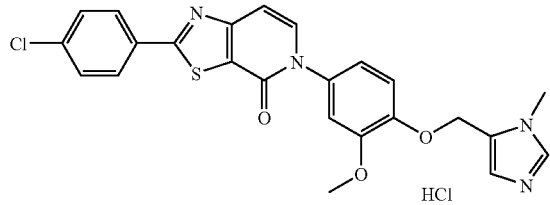

MS (ES+) 479.0 (M+1)⁺. ¹H NMR (400 MHz, DMSO-d6): δ 14.56 (s, 1H), 9.18 (s, 1H), 8.16 (d, 2H, J=8.4 Hz), 7.86 (d, 1H, J=1.3 Hz), 7.76 (d, 1H, J=7.5 Hz), 7.67 (d, 2H, J=8.4 Hz), 7.32 (d, 1H, J=8.8 Hz), 7.20 (d, 1H, J=2.6 Hz), 7.06 (m, 2H), 5.32 (s, 2H), 3.93 (s, 3H), 3.79 (s, 3H).

Example 43

2-(4-Chloro-phenyl)-5-[3-methoxy-4-(2-morpholin-4-yl-ethoxy)-phenyl]-5H-thiazolo[5,4-c]pyridin-4-one hydrochloride

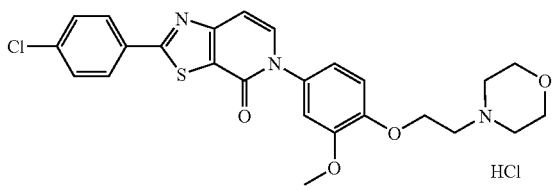

MS (ES+) 498.0 (M+1)⁺. ¹H NMR (400 MHz, DMSO-d6): δ 11.03 (s, 1H), 8.11 (d, 2H, J=8.8 Hz), 7.71 (d, 1H, J=7.3 Hz), 7.63 (d, 2H, J=8.8 Hz), 7.16 (m, 2H), 7.02 (m, 2H), 4.44 (t, 2H, J=4.9 Hz), 3.96 (d, 2H, J=10.5 Hz), 3.77 (m, 5H), 3.56-3.52 (m, 4H), 3.21 (m, 2H).

Example 44

2-(4-Chloro-phenyl)-5-[4-(1H-imidazol-4-yl-methoxy)-3-methoxy-phenyl]-6,7-dihydro-5H-thiazolo[5,4-c]pyridin-4-one hydrochloride

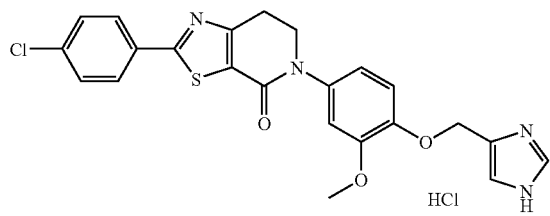

¹H NMR (400 MHz, CD₃OD): δ 8.92 (d, 1H, J=1.3 Hz), 8.00 (4, 2H, J=8.8 Hz), 7.62 (s, 1H), 7.51 (d, 2H, J=8.8 Hz), 7.08 (m, 2H), 6.91 (dd, 1H, J=8.4, 2.4 Hz), 5.19 (s, 2H), 4.11 (t, 2H, J=7.0 Hz), 3.83 (s, 3H), 3.28 (t, 2H, J=7.0 Hz).

Preparation 128

4-(2-Benzyloxy-ethyl)-morpholin-3-one

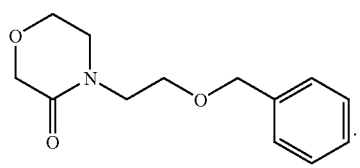

Add NaH (0.47 g, 11.8 mmol) to a solution of morpholin-3-one (Vieles, P.; Seguin, J., *Bulletin de la Societe Chimique de France*, 1953, 287-9) (1.0 g, 9.9 mmol) in DMF (10 ml) at room temperature. Stir for 30 min, add (2-bromo-ethoxymethyl)-benzene (2.2 g, 10.2 mmol), and stir at room temperature for 18 h. Dilute with water and extract with EtOAc (2×). Combine the organics, dry, and concentrate. Purify by flash chromatography using 0-5% MeOH in CH₂Cl₂, to give the product as an oil. (1.7 g, 74%). ¹H NMR (400 MHz, CDCl₃): δ 7.28 (m, 5H), 4.48 (s, 2H), 4.13 (s, 2H), 3.80 (t, 2H, J=5.1 Hz), 3.65 (m, 2H), 3.59 (dd, 2H, J=7.5, 2.6 Hz), 3.48 (t, 2H, J=5.1 Hz).

Preparation 129

4-(2-Hydroxy-ethyl)-morpholin-3-one

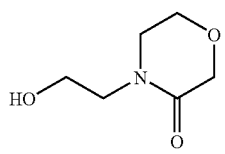

Dissolve 4-(2-benzyloxy-ethyl)-morpholin-3-one (1.7 g, 7.23 mmol) in ethanol (25 mL) and add 5% Pd/C (0.30 g). Hydrogenate at 60 psi overnight, filter the black mixture through Celite®, and wash the Celite® with additional ethanol (approximately 10 mL). Concentrate the filtrate to give the title compound as an oil (0.7 g, 70%). MS (ES+) 146.3 (M+1)⁺. ¹H NMR (400 MHz, CDCl₃): δ 4.11 (s, 2H), 3.83 (t, 2H, J=5.1 Hz), 3.73 (t, 2H, J=5.3 Hz), 3.49 (t, 2H, J=5.3 Hz), 3.43 (t, 2H, J=5.1 Hz), 3.12 (s, 1H).

103

Example 45

2-(4-Chloro-phenyl)-5-{3-methoxy-4-[2-(3-oxo-morpholin-4-yl)-ethoxy]-phenyl}-5H-thiazolo[5,4-c]pyridin-4-one

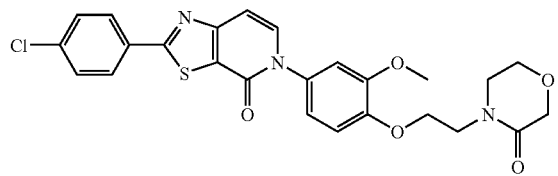

Combine 2-(4-chloro-phenyl)-5-(4-hydroxy-3-methoxy-phenyl)-5H-thiazolo[5,4-c]pyridin-4-one (0.70 g, 1.82 mmol), 4-(2-hydroxy-ethyl)-morpholin-3-one (0.50 g, 3.45 mmol) and triphenylphosphine (0.50 g, 1.90 mmol) in THF (10.0 mL), stir for 10 min and add DIAD (0.77 g, 3.81 mmol). Heat to 80° C. for 2 days, cool the reaction mixture, and dilute with water. Extract with $CH_2Cl_2$ (2×), combine the organics, dry, and concentrate under vacuum. Purify the product by flash chromatography using 0-10% MeOH in $CH_2Cl_2$ to give the title compound (0.40 g, 43%). MS (ES+) 512.0 (M+1)$^+$. $^1$H NMR (400 MHz, CDCl$_3$): δ 8.01 (d, 2H, J=8.6 Hz), 7.47 (d, 2H, J=8.6 Hz), 7.40 (d, 1H, J=7.5 Hz), 6.98-6.95 (m, 3H), 6.91 (dd, 1H, J=8.6, 2.4 Hz), 4.27 (t, 2H, J=5.2 Hz), 4.17 (s, 2H), 3.89-3.81 (m, 7H), 3.68 (t, 2H, J=5.1 Hz).

Example 46

2-(4-Chloro-phenyl)-5-[3-chloro-4-(2-pyrrolidin-1-yl-ethoxy)-phenyl]-6,7-dihydro-5H-thiazolo[5,4-c]pyridin-4-one,

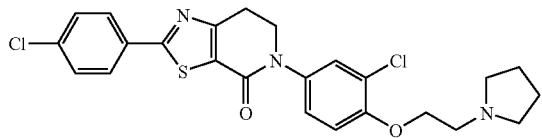

Dissolve 3-chloro-4-(2-pyrrolidin-1-yl-ethoxy)-phenylamine (0.20 g, 0.83 mmol) in $CH_2Cl_2$ (10.0 mL) and treat with trimethylaluminum (2.0M in hexanes, 0.6 mL, 1.20 mmol). Stir at room temperature for 15 min and add 2-(4-chloro-phenyl)-6,7-dihydro-pyrano[4,3-d]thiazol-4-one (0.22 g, 0.83 mmol) neat and stir the reaction at room temperature for 2 h. Carefully quench the mixture with saturated Rochelles salt solution and stir at room temperature for 1 h. Dilute with water and extract with $CH_2Cl_2$ (2×). Combine the organic portions and dry, filter and concentrate. Dissolve the residue in $CH_2Cl_2$, and treat with triethylamine (0.50 mL, 3.56 mmol) followed by methanesulfonyl chloride (0.05 mL, 0.65 mmol). Stir for 1 h at room temperature, dilute with water and extract with $CH_2Cl_2$ (2×). Combine the organic portions and dry, filter, and concentrate. Dissolve the residue in THF and treat with NaH (0.03 g, 0.75 mmol) and stir at room temperature for 18 h. Dilute the reaction with water and extract with $CH_2Cl_2$ (2×). Combine the organic portions, dry, filter, and concentrate. Purify the crude material by flash chromatography, using a gradient of 0% to 10% 2N NH$_3$/MeOH in $CH_2Cl_2$, to give the title compound (80 mg, 37%).

104

MS (ES+) 488.0 (M+1)+. $^1$H NMR (400 MHz, CDCl$_3$): δ 7.93 (d, 2H, J=8.3 Hz), 7.45 (d, 2H, J=8.8 Hz), 7.39 (d, 1H, J=2.2 Hz), 7.22 (dd, 1H, J=8.8, 2.6 Hz), 6.97 (d, 1H, J=9.2 Hz), 4.22 (t, 2H, J=5.9 Hz), 4.07 (t, 2H, J=7.0 Hz), 3.28 (t, 2H, J=7.0 Hz), 3.01 (t, 2H, J=5.9 Hz), 2.73 (m 4H), 1.84 (m 4H).

Example 47

2-(4-Chloro-phenyl)-5-[1-methyl-3-(2-pyrrolidin-1-yl-ethyl)-1H-indol-6-yl]-6,7-dihydro-5H-thiazolo[5,4-c]pyridin-4-one hydrochloride

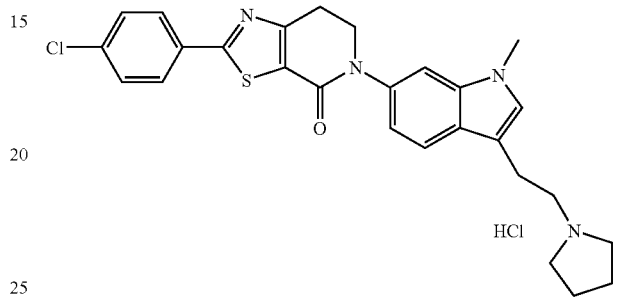

Dissolve 2-(4-chloro-phenyl)-4-(2-hydroxy-ethyl)-thiazole-5-carboxylic acid [1-methyl-3-(2-pyrrolidin-1-yl-ethyl)-1H-indol-6-yl]-amide (0.92 g, 1.81 mmol) in THF (20 mL) and treat the solution with tributylphosphine (1.0 mL, 3.47 mmol) and diisopropylazodicarboxylate (0.73 mL, 3.61 mmol). Stir the reaction at room temperature for 18 h. Concentrate and purify the crude material by flash chromatography, using 0-10% 2N NH$_3$/MeOH in $CH_2Cl_2$, to give the free amine. Dissolve the free amine in MeOH (10.0 mL) and add 1N HCl in ether (5.0 mL), sonicate for 5 min, and concentrate. Triturate the solid with ether, filter the solid, and dry to give the title compound (0.64 g, 69%). MS (ES+) 491.1 (M+1)$^+$. $^1$H NMR (400 MHz, DMSO-d6): δ 10.39 (s, 1H), 8.03 (d, 2H, J=8.6 Hz), 7.63 (d, 1H, J=8.6 Hz), 7.59 (d, 2H, J=8.6 Hz), 7.44 (d, 1H, J=1.8 Hz), 7.26 (s, 1H), 7.06 (dd, 1H, J=8.5, 1.6 Hz), 4.11 (t, 2H, J=7.0 Hz), 3.72 (s, 3H), 3.54 (m, 2H), 3.33 (m, 2H), 3.27 (t, 2H, J=6.9 Hz), 2.97 (m, 4H), 1.98 (m, 2H), 1.85 (m, 2H).

Example 48

2-(4-Chloro-phenyl)-5-[6-(4-methyl-piperazin-1-yl)-pyridin-3-yl]-6,7-dihydro-5H-thiazolo[5,4-c]pyridin-4-one, dihydrochloride salt

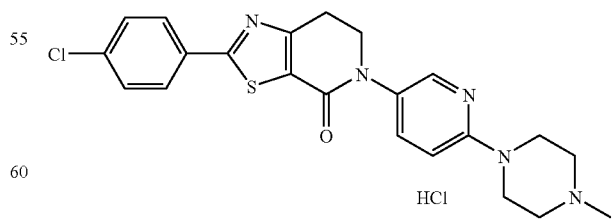

Prepare the title compound by essentially following procedures as described for Example 46 and isolating as the dihydrochloride salt. MS (ES+) 439.8 (M+1)$^+$. $^1$H NMR (400 MHz, DMSO-d6): δ 11.38 (s, 1H), 8.19 (d, 1H, J=2.6 Hz), 8.01 (d, 2H, J=8.6 Hz), 7.80 (dd, 1H, J=9.1, 2.5 Hz), 7.58 (d, 2H, J=8.8 Hz), 7.14 (d, 1H, J=9.4 Hz), 4.42 (d, 2H, J=13.8 Hz), 4.04 (t, 2H, J=6.9 Hz), 3.42 (m, 4H), 3.24 (t, 2H, J=6.9 Hz), 3.08 (m, 2H), 2.75 (d, 3H, J=4.2 Hz).

Example 49

2-(4-Chloro-phenyl)-5-[3-methoxy-4-(3-methyl-3H-imidazol-4-ylmethoxy)-phenyl]-6,7-dihydro-5H-thiazolo[5,4-c]pyridin-4-one

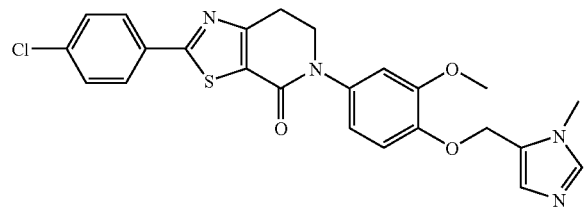

Treat a solution of (3-methyl-3H-imidazol-4-yl)-methanol (60.0 mg, 0.54 mmol) in CH$_2$Cl$_2$ with oxalyl chloride (0.15 g, 1.2 mmol) and 2 drops of DMF. Stir at room temperature for 4 h, concentrate, and dissolve in DMF (5.0 mL). Add this solution to a suspension of NaH (62.5 mg, 1.6 mmol) and 2-(4-chloro-phenyl)-5-(4-hydroxy-3-methoxy-phenyl)-5H-thiazolo[5,4-c]pyridin-4-one (200.0 mg, 0.5 mmol) in DMF (5 mL). Stir at room temperature for 2 h, dilute with water, and extract with CH$_2$Cl$_2$ (2×). Combine the organics, dry, and concentrate. Purify by flash chromatography, using 0-10% 2N NH$_3$/MeOH in CH$_2$Cl$_2$, to give the title compound (100.0 mg, 40%). MS (ES+) 481.0 (M+1)$^+$. $^1$H NMR (400 MHz, CDCl3): δ7.90 (d, 2H, J=8.4 Hz), 7.44 (d, 2H, J=4.0 Hz), 7.41 (s, 1H), 7.07 (s, 1H), 6.97 (d, 1H, J=8.8 Hz), 6.94 (d, 1H, J=2.2 Hz), 6.81 (dd, 1H, J=8.6, 2.4 Hz), 5.04 (s, 2H), 4.07 (t, 2H, J=7.0 Hz), 3.83 (s, 3H), 3.72 (s, 3H), 3.27 (t, 2H, J=6.8 Hz).

Preparation 130

2-(4-Chloro-phenyl)-5-[4-(3,3-diethoxy-propyl)-3-methoxy-phenyl]-5H-thiazolo[5,4-c]pyridin-4-one

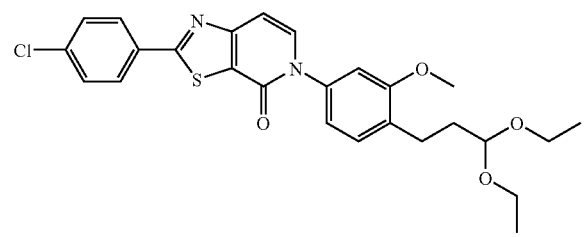

Prepare the title compound by essentially following the procedures as described for Preparation 132. $^1$H NMR (400 MHz, CDCl$_3$): δ 8.02 (d, 2H, J=8.3 Hz), 7.48 (d, 2H, J=8.3 Hz), 7.42 (d, 1H, J=7.0 Hz), 7.25 (d, 1H, J=7.9 Hz), 6.96 (d, 1H, J=7.5 Hz), 6.93-6.87 (m, 2H), 4.54 (t, 1H, J=5.7 Hz), 3.83 (s, 3H), 3.72-3.63 (m, 2H), 3.56-3.47 (m, 2H), 2.74-2.68 (m, 2H), 1.97-1.90 (m, 2H), 1.22 (t, 6H, J=7.0 Hz).

Preparation 131

3-{4-[2-(4-Chloro-phenyl)-4-oxo-4H-thiazolo[5,4-c]pyridin-5-yl]-2-methoxy-phenyl}-propionaldehyde

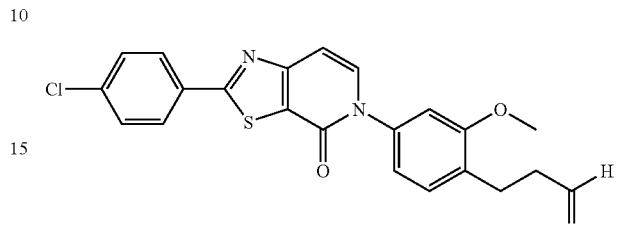

Dissolve 2-(4-chloro-phenyl)-5-[4-(3,3-diethoxy-propyl)-3-methoxy-phenyl]-5H-thiazolo[5,4-c]pyridin-4-one (180 mg, 0.36 mmol) in THF (2.0 mL) and water (1.0 mL) then add glacial acetic acid (0.6 mL). Stir the solution at 45° C. overnight. Dilute the solution with EtOAc (50 mL), wash with saturated NaHCO$_3$ (20 mL), then dry, filter and concentrate the solution. Purify the crude material by flash chromatography, using a linear gradient of 100% hexanes to 80% EtOAc/hexanes, to give the title compound (94 mg, 61%). MS (ES+) 425.0 (M+1)$^+$. $^1$H NMR (400 MHz, CDCl$_3$): δ 9.83 (s, 1H), 8.03 (d, 2H, J=8.3 Hz), 7.49 (d, 2H, J=8.8 Hz), 7.41 (d, 1H, J=7.5 Hz), 7.26 (m, 1H), 6.99-6.89 (m, 3H), 3.84 (s, 3H), 2.99 (t, 2H, J=7.3 Hz), 2.77 (t, 2H, J=7.3 Hz).

Example 50

2-(4-Chloro-phenyl)-5-[3-methoxy-4-(3-pyrrolidin-1-yl-propyl)-phenyl]-5H-thiazolo[5,4-c]pyridin-4-one

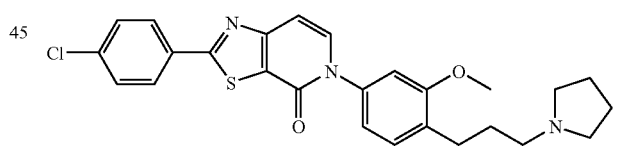

Dissolve 3-{4-[2-(4-chloro-phenyl)-4-oxo-4H-thiazolo[5,4-c]pyridin-5-yl]-2-methoxy-phenyl}-propionaldehyde (94 mg, 0.22 mmol) in 1,2-dichloroethane (2.2 mL) and add pyrrolidine (20 µL, 0.24 mmol), AcOH (19 µL, 0.33 mmol), and NaHB(OAc)$_3$ (70 mg, 0.33 mmol). Stir the yellow solution at room temperature for 1 h, then add 1N NaOH (5 mL), and extract the mixture with CH$_2$Cl$_2$ (2×10 mL). Combine the organic portions, then dry, filter, and concentrate. Purify the crude material by flash chromatography, using 8% 2N NH$_3$ in MeOH/CHCl$_3$ as eluent, to give the title compound (75 mg, 71%). MS (ES+) 480.1 (M+1)$^+$. $^1$H NMR (400 MHz, CDCl$_3$): δ 8.03 (d, 2H, J=8.3 Hz), 7.48 (d, 2H, J=8.8 Hz), 7.43 (d, 1H, J=7.5 Hz), 7.25 (t, 1H, J=3.7 Hz), 6.97 (d, 1H, J=7.5 Hz), 6.93-6.88 (m, 2H), 3.83 (s, 3H), 2.70 (t, 2H, J=7.7 Hz), 2.60 (br s, 6H), 1.96-1.79 (m, 6H).

Example 51

2-(4-Chloro-phenyl)-5-[4-(4-hydroxy-piperidin-1-yl)-3-methoxy-phenyl]-6,7-dihydro-5H-thiazolo[5,4-c]pyridin-4-one, hydrochloride salt

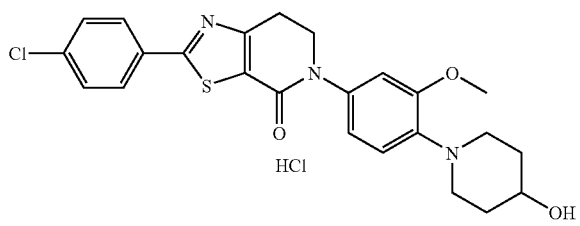

Dissolve 2-(4-chloro-phenyl)-5-[3-methoxy-4-(4-triisopropylsilanyloxy-piperidin-1-yl)-phenyl]-6,7-dihydro-5H-thiazolo[5,4-c]pyridin-4-one (681 mg, 1.09 mmol) in THF (10 mL) then add tert-butylammonium fluoride (1.0 M solution in THF, 1.30 mL, 1.30 mmol). Stir the solution at room temperature for 2 h, then dilute with EtOAc (50 mL) and wash with 2N NH$_4$Cl (20 mL). Concentrate the organic solution and purify the crude material by flash chromatography, using 8% MeOH (2N NH$_3$)/CHCl$_3$ as eluent, to give semi-pure material. Triturate the solids with ether to give the title compound as the free base (265 mg, 52%). Mix 2-(4-chloro-phenyl)-5-[4-(4-hydroxy-piperidin-1-yl)-3-methoxy-phenyl]-6,7-dihydro-5H-thiazolo[5,4-c]pyridin-4-one (53 mg, 0.11 mmol) in MeOH (1 mL) and add 1N HCl (2.0 mL, 2.0 mmol). Stir the mixture at room temperature until all the solids dissolve and then cool to −20° C. overnight. Collect the precipitate by filtration, wash with ether, and dry under vacuum to give the title compound (40 mg, 70%). MS (ES+) 470.0 (M+1)$^+$. $^1$H NMR (400 MHz, DMSO-d6): δ 11.69 (s, 1H), 8.06 (d, 2H, J=8.4 Hz), 7.70 (s, 1H), 7.63 (d, 2H, J=8.4 Hz), 7.34 (s, 1H), 7.14 (s, 1H), 4.65 (s, 4H), 4.16 (t, 2H, J=6.8 Hz), 3.95 (s, 3H), 3.64-3.32 (m, 2H), 3.29 (t, 2H, J=7.0 Hz), 2.11-1.76 (m, 4H),

Example 52

2-(4-Chloro-phenyl)-5-[3-methoxy-4-(3-pyrrolidin-1-yl-propyl)-phenyl]-5H-thiazolo[5,4-c]pyridin-4-one hydrochloride

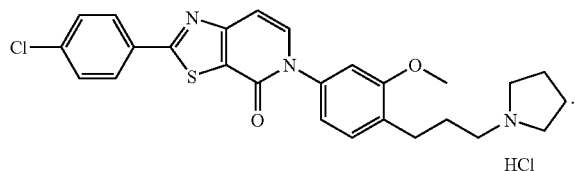

Mix 2-(4-chloro-phenyl)-5-[3-methoxy-4-(3-pyrrolidin-1-yl-propyl)-phenyl]-5H-thiazolo[5,4-c]pyridin-4-one (833 mg, 1.74 mmol) in MeOH (10 mL) and add 1N HCl (2.0 mL, 2.0 mmol). Stir the mixture at room temperature until all the solids dissolve then cool to −20° C. overnight. Collect the precipitate by filtration, wash with ether, and dry under vacuum to give the title compound (725 mg, 81%). MS (ES+) 480.0 (M+1)$^+$. $^1$H NMR (400 MHz, CDCl$_3$): δ 10.14 (s, 1H), 8.16 (d, 2H, J=8.8 Hz), 7.77 (d, 1H, J=7.5 Hz), 7.67 (d, 2H, J=8.8 Hz), 7.34 (d, 1H, J=8.4 Hz), 7.15 (d, 1H, J=1.8 Hz), 7.09-7.02 (m, 2H), 3.83 (s, 3H), 3.58-3.50 (m, 2H), 3.20-3.13 (m, 2H), 3.02-2.94 (m, 2H), 2.68 (t, 2H, J=7.7 Hz), 2.03-1.93 (m, 4H), 1.90-1.83 (m, 2H).

Example 53

2-(4-Chloro-phenyl)-5-[3-methoxy-4-(3-pyrrolidin-1-yl-propyl)-phenyl]-6,7-dihydro-5H-thiazolo[5,4-c]pyridin-4-one

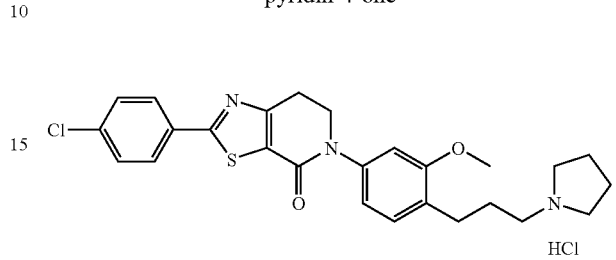

Prepare the titled compound by essentially following procedures as described for Example 52. MS (ES+) 482.0 (M+1)$^+$. $^1$H NMR (400 MHz, CDCl$_3$) δ: 10.45 (s, 1H), 8.05 (d, 2H, J=8.4 Hz), 7.62 (d, 2H, J=8.8 Hz), 7.22 (d, 1H, J=7.9 Hz), 7.05 (d, 1H, J=1.8 Hz), 6.93 (dd, 1H, J=7.9, 1.8 Hz), 4.11 (t, 2H, J=7.0 Hz), 3.80 (s, 3H), 3.55-3.47 (m, 2H), 3.27 (t, 2H, J=6.8 Hz), 3.15-3.08 (m, 2H), 3.00-2.91 (m, 2H), 2.62 (t, 2H, J=7.5 Hz), 2.02-1.81 (m, 6H).

Preparation 132

Methanesulfonic acid 2-[2-(4-chloro-phenyl)-5-(1-triisopropylsilanyl-1H-indol-5-ylcarbamoyl)-thiazol-4-yl]-ethyl ester

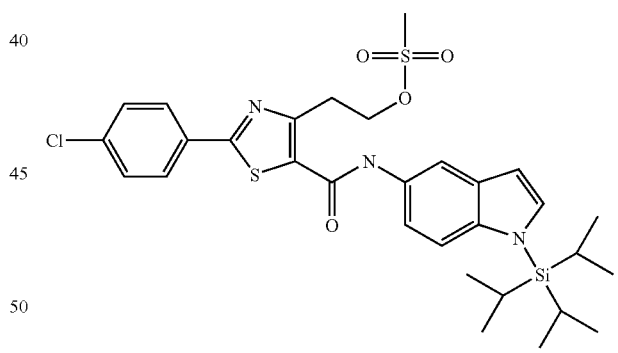

Dissolve 2-(4-chloro-phenyl)-4-(2-hydroxy-ethyl)-thiazole-5-carboxylic acid (1-triisopropylsilanyl-1H-indol-5-yl)-amide (1.54 g, 2.77 mmol) in CH$_2$Cl$_2$ (25 mL) and add Et$_3$N (0.33 mL, 2.36 mmol) and methanesulfonyl chloride (0.16 mmol, 2.13 mmol). Stir the mixture at room temperature for 2 h, then add additional Et$_3$N (0.33 mL, 2.36 mmol) and methanesulfonyl chloride (0.16 mmol, 2.13 mmol). Stir the mixture for an additional 2 h, dilute with EtOAc (50 mL), then wash with water (20 mL) and brine (20 mL). Dry, filter and concentrate the organic solution. Purify the crude material by flash chromatography, using a linear gradient of 100% hexanes to 50% EtOAc/hexanes as eluent, to give the title compound (1.15 g, 100%). MS (ES+) 632.1 (M+1)$^+$. $^1$H NMR (400 MHz, CDCl$_3$): δ 7.96-7.84 (m, 4H), 7.50-7.43 (m, 3H), 7.30-7.26 (m, 2H), 6.62 (d, 1H, J=3.1 Hz), 4.77 (t, 2H, J=6.2 Hz), 3.60 (t, 2H, J=6.4 Hz), 2.99 (s, 3H), 1.73-1.65 (m, 3H), 1.14 (d, 18H, J=7.5 Hz).

Preparation 133

2-(4-Chloro-phenyl)-5-(1-triisopropylsilanyl-1H-indol-5-yl)-6,7-dihydro-5H-thiazolo[5,4-c]pyridin-4-one

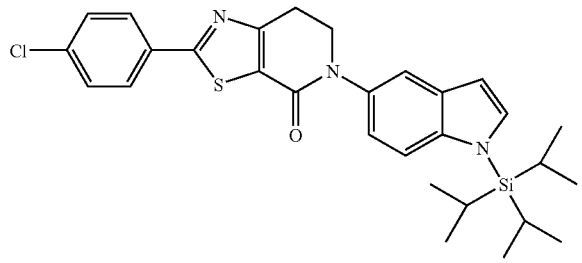

Dissolve 2-(4-chloro-phenyl)-4-(2-hydroxy-ethyl)-thiazole-5-carboxylic acid (1-triisopropylsilanyl-1H-indol-5-yl)-amide in CH$_2$Cl$_2$ (25 mL) and add Et$_3$N (0.33 mL, 2.36 mmol) and methanesulfonyl chloride (0.16 mmol, 2.13 mmol). Stir the mixture at room temperature for 2 h, then add additional Et$_3$N (0.33 mL, 2.36 mmol) and methanesulfonyl chloride (0.16 mmol, 2.13 mmol). Stir the mixture for an additional 2 h, dilute with EtOAc (50 mL), then wash with water (20 mL) and brine (20 mL). Dry, filter and concentrate the organic solution then and purify the crude material by flash chromatography, using a linear gradient of 100% hexanes to 50% EtOAc/hexanes as eluent, to give the title compound (1.15 g, 100%). MS (ES+) 536.1 (M+1)$^+$. $^1$H NMR (400 MHz, CDCl$_3$) δ: 7.93 (d, 2H, J=8.3 Hz), 7.56 (d, 1H, J=1.8 Hz), 7.50 (d, 1H, J=8.8 Hz), 7.44 (d, 2H, J=8.3 Hz), 7.27 (d, 1H, J=3.1 Hz), 7.14-7.10 (m, 1H), 6.61 (d, 1H, J=2.6 Hz), 4.16 (t, 2H, J=6.8 Hz), 3.29 (t, 2H, J=7.0 Hz), 1.73-1.65 (m, 3H), 1.14 (d, 18H, J=7.5 Hz).

Preparation 134

2-(4-Chloro-phenyl)-5-(1H-indol-5-yl)-6,7-dihydro-5H-thiazolo[5,4-c]pyridin-4-one

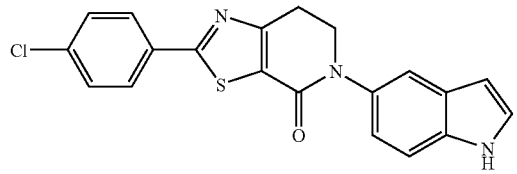

Mix 2-(4-chloro-phenyl)-5-(1-triisopropylsilanyl-1H-indol-5-yl)-6,7-dihydro-5H-thiazolo[5,4-c]pyridin-4-one (4.23 g, 7.89 mmol) in THF (50 mL) and add tetrabutyl-ammonium fluoride (1.0M in THF, 10 vmL, 10 mmol). Stir the red solution at room temperature for 2 h, then quench with aqueous 2M NH$_4$Cl (50 mL) and extract with CH$_2$Cl$_2$ (3×50 mL). Dry, filter, and concentrate the organic solution. Purify the crude material by flash chromatography, using 8% MeOH (2N NH$_3$)/CHCl$_3$ as eluent, then triturate the resulting yellow solid with ether to give the title compound (2.68 g, 89%). MS (ES+) 380.0 (M+1)$^+$. $^1$H NMR (400 MHz, CDCl$_3$): δ 11.20 (s, 1H), 8.05 (d, 2H, J=8.4 Hz), 7.62 (d, 2H, J=8.4 Hz), 7.53 (d, 1H, J=1.8 Hz), 7.43-7.38 (m, 2H), 7.09 (dd, 1H, J=8.6, 2.0 Hz), 6.45-6.43 (m, 1H), 4.11 (t, 2H, J=7.0 Hz), 3.28 (t, 2H, J=7.0 Hz).

Preparation 135

2-(4-Chloro-phenyl)-5-(2,3-dihydro-1H-indol-5-yl)-6,7-dihydro-5H-thiazolo[5,4-c]pyridin-4-one

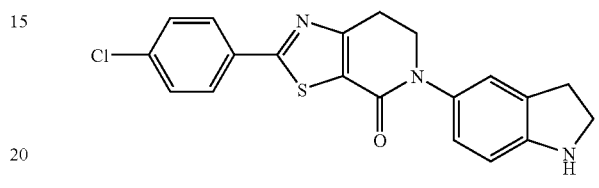

Prepare the title compound by essentially following procedure as described in Preparation 134. MS (ES+) 381.9 (M+1)$^+$. $^1$H NMR (400 MHz, CDCl$_3$): δ 7.91 (d, 2H, J=8.3 Hz), 7.43 (d, 2H, J=8.8 Hz), 7.13 (s, 1H), 6.99 (dd, 1H, J=8.1, 2.0 Hz), 6.76 (d, 1H, J=8.3 Hz), 4.04 (t, 2H, J=6.8 Hz), 3.64 (t, 2H, J=8.3 Hz), 3.26 (t, 2H, J=6.8 Hz), 3.08 (t, 2H, J=8.3 Hz).

Preparation 136

(±)-3-{5-[2-(4-Chloro-phenyl)-4-oxo-6,7-dihydro-4H-thiazolo[5,4-c]pyridin-5-yl]-2,3-dihydro-indole-1-carbonyl}-pyrrolidine-1-carboxylic acid tert-butyl ester

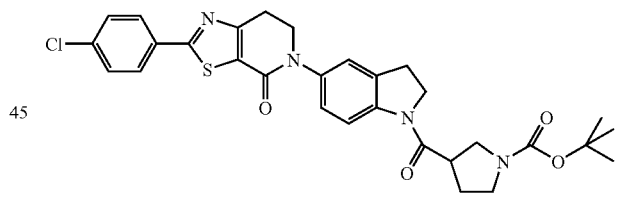

Dissolve 2-(4-chloro-phenyl)-5-(2,3-dihydro-1H-indol-5-yl)-6,7-dihydro-5H-thiazolo[5,4-c]pyridin-4-one (163 mg, 0.43 mmol) in CH$_2$Cl$_2$ (4.0 mL) and add (±)-pyrrolidine-1,3-dicarboxylic acid 1-tert-butyl ester (140 mg, 0.65 mmol), Et$_3$N (0.09 mL, 0.64 mmol), and [dimethylamino-([1,2,3]triazolo[4,5-b]pyridin-3-yloxy)-methylene]-dimethyl-ammonium hexafluoro phosphate (246 mg, 0.65 mmol). Stir the solution at room temperature for 2 h. Concentrate and purify by flash chromatography, using a 8% MeOH (2N NH$_3$)/CHCl$_3$ as eluent, to give the title compound (231 mg, 93%). $^1$H NMR (400 MHz, DMSO-d6): δ 8.10 (d, 1H, J=8.8 Hz), 8.05 (d, 2H, J=8.8 Hz), 7.62 (d, 2H, J=8.3 Hz), 7.29 (s, 1H), 7.19-7.15 (m, 1H), 4.22 (t, 2H, J=8.8 Hz), 4.07 (t, 2H, J=7.0 Hz), 3.54 (t, 1H, J=8.8 Hz), 3.47-3.36 (m, 3H), 3.29 (m, 1H), 3.26 (t, 2H, J=6.2 Hz), 3.18 (t, 2H, J=8.3 Hz), 2.16 (m, 1H), 2.01 (m, 1H), 1.41 (s, 9H).

Example 54

(±)-2-(4-Chloro-phenyl)-5-[1-pyrrolidine-3-carbonyl]-2,3-dihydro-1H-indol-5-yl]-6,7-dihydro-5H-thiazolo[5,4-c]pyridin-4-onium trifluoroacetate

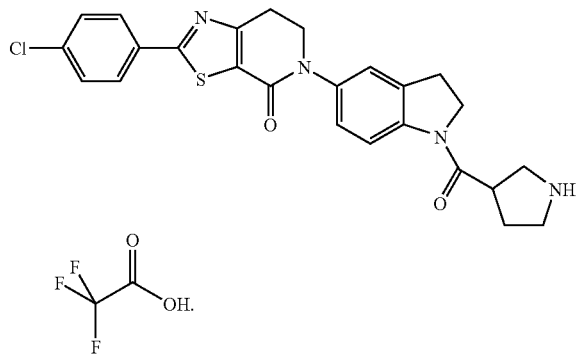

Dissolve (±)-3-{5-[2-(4-chloro-phenyl-4-oxo-6,7-dihydro-4H-thiazolo[5,4-c]pyridin-5-yl]-2,3-dihydro-indole-1-carbonyl}-pyrrolidine-1-carboxylic acid tert-butyl ester (225 mg, 0.39 mmol) in TFA (2 mL) and stir at room temperature for 1 h. Concentrate the solution and re-dissolve the crude material in MeOH. Remove the light yellow solid by filtration and wash with ether. Dry under vacuum to give the title compound (188 mg, 82%). MS (ES+) 479.0 (M+1)+. 1H NMR (400 MHz, DMSO-d6): δ 8.89 (s, 2H), 8.10 (d, 1H, J=8.8 Hz), 8.05 (d, 2H, J=8.8 Hz), 7.62 (d, 2H, J=8.8 Hz), 7.31 (s, 1H), 7.22-7.18 (m, 1H), 4.22 (t, 2H, J=9.4 Hz), 4.07 (t, 2H, J=7.0 Hz), 3.56-3.47 (m, 2H), 3.42-3.35 (m, 1H), 3.29-3.20 (m, 6H), 2.35-2.27 (m, 1H), 2.13-2.03 (m, 1H).

Example 55

(±)-2-(4-Chloro-phenyl)-5-[1-(1-methyl-pyrrolidine-3-carbonyl)-2,3-dihydro-1H-indol-5-yl]-6,7-dihydro-5H-thiazolo[5,4-c]pyridin-4-one

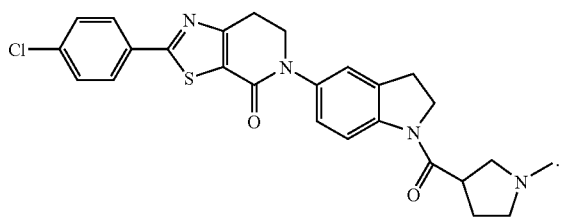

Dissolve (±)-2-(4-chloro-phenyl)-5-[1-(pyrrolidine-3-carbonyl)-2,3-dihydro-1H-indol-5-yl]-6,7-dihydro-5H-thiazolo[5,4-c]pyridin-4-onium trifluoroacetate (167 mg, 0.28 mmol) in 1,2-dichloroethane (3.0 mL) and add paraformaldehyde (203 mg), acetic acid (0.02 mL, 0.35 mmol), and sodium triacetoxyborohydride (78 mg, 0.37 mmol). Stir the mixture at room temperature for 4 h, then dilute with CH2Cl2 (20 mL) and wash with 1N NaOH (10 mL). Dry, filter and concentrate the organic solution then and purify the crude material by flash chromatography, using a 8% MeOH (2N NH3)/CHCl3 as eluent, to give the title compound as a yellow solid (86 mg, 62%). MS (ES+) 493.0 (M+1)+. 1H NMR (400 MHz, DMSO-d6): δ 8.30 (d, 1H, J=8.8 Hz), 7.95 (d, 2H, J=8.3 Hz), 7.47 (d, 2H, J=8.3 Hz), 7.28 (s, 1H), 7.15 (d, 1H, J=10.1 Hz), 4.17 (t, 2H, J=8.8 Hz), 4.12 (t, 2H, J=6.8 Hz), 3.33-3.22 (m, 5H), 3.17-3.10 (m, 1H), 3.01-2.90 (m, 1H), 2.85-2.76 (m, 1H), 2.64-2.56 (m, 1H), 2.50 (s, 3H), 2.29-2.21 (m, 2H).

Example 56

2-(4-Chloro-phenyl)-5-(1-pyridin-2-ylmethyl-1H-indol-5-yl)-6,7-dihydro-5H-thiazolo[5,4-c]pyridin-4-one

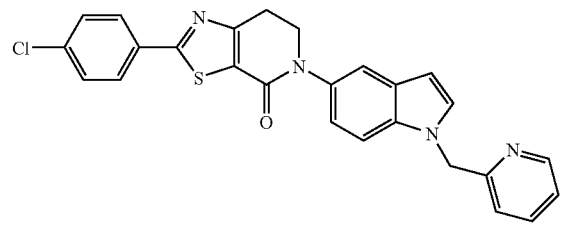

Dissolve 2-(4-chloro-phenyl)-5-(1H-indol-5-yl)-6,7-dihydro-5H-thiazolo[5,4-c]pyridin-4-one (49 mg, 0.13 mmol) in DMF (1 mL) and add sodium hydride (17 mg, 0.42 mmol). Stir the mixture at room temperature for 30 min then add 2-bromomethyl-pyridine hydrobromide (35 mg, 0.14 mmol). Stir the mixture at room temperature for 5 h, then dilute with EtOAc (30 mL) and wash with saturated NaHCO3 (10 mL). Dry, filter and concentrate the organic solution. Purify the crude material by flash chromatography, using a linear gradient of 20% to 80% EtOAc/hexanes as eluent, to give the title compound (32 mg, 52%). MS (ES+) 471.0 (M+1)+. 1H NMR (400 MHz, CDCl3) δ: 8.55-8.53 (m, 1H), 8.05 (d, 2H, J=8.4 Hz), 7.73 (dt, 1H, J=7.7, 1.8 Hz), 7.62 (d, 2H, J=8.8 Hz), 7.57-7.55 (m, 2H), 7.45 (d, 1H, J=8.8 Hz), 7.30-7.26 (m, 1H), 7.10 (dd, 1H, J=8.6, 2.0 Hz), 7.03 (d, 1H, J=7.9 Hz), 6.52 (d, 1H, J=3.5 Hz), 5.53 (s, 2H), 4.10 (t, 2H, J=7.0 Hz), 3.27 (t, 2H, J=7.0 Hz).

Prepare Examples 57 and 58 by essentially following the procedure as described for Example 56, using the appropriate alkyl halide.

Example 57

2-(4-Chloro-phenyl)-5-(1-pyridin-4-ylmethyl-1H-indol-5-yl)-6,7-dihydro-5H-thiazolo[5,4-c]pyridin-4-one

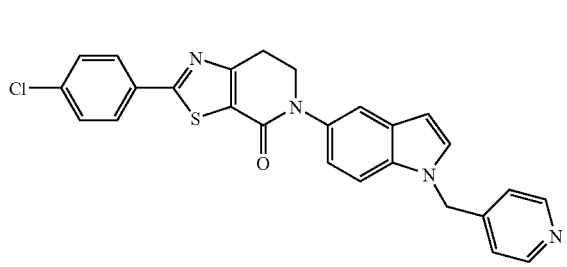

MS (ES+) 471.0 (M+1)+. 1H NMR (400 MHz, CDCl3): δ 8.50 (d, 2H, J=5.7 Hz), 8.05 (d, 2H, J=8.8 Hz), 7.62 (d, 2H, J=8.8 Hz), 7.58 (d, 2H, J=2.6 Hz), 7.42 (d, 1H, J=8.8 Hz), 7.14-7.09 (m, 3H), 6.56 (d, 1H, J=3.1 Hz), 5.53 (s, 2H), 4.11 (t, 2H, J=6.8 Hz), 3.28 (t, 2H, J=7.0 Hz).

Example 58

2-(4-Chloro-phenyl)-5-[1-(2-morpholin-4-yl-ethyl)-1H-indol-5-yl]-6,7-dihydro-5H-thiazolo[5,4-c]pyridin-4-one

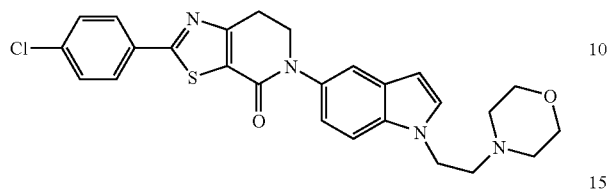

MS (ES+) 493.0 (M+1)+. ¹H NMR (400 MHz, DMSO-d6): δ 8.06 (d, 2H, J=8.8 Hz), 7.68 (d, 1H, J=8.8 Hz), 7.62 (d, 2H, J=8.8 Hz), 7.58 (d, 1H, J=2.2 Hz), 7.50 (d, 1H, J=3.1 Hz), 7.22 (dd, 1H, J=8.6, 2.0 Hz), 6.53 (d, 1H, J=2.6 Hz), 4.71 (s, 2H), 4.12 (t, 2H, J=7.0 Hz), 4.02-3.94 (m, 2H), 3.84-3.75 (m, 2H), 3.56-3.42 (m, 4H), 3.29 (t, 2H, J=7.0 Hz), 3.20-3.08 (m, 2H).

Preparation 137

5-nitro-3H-benzooxazole-2-thione

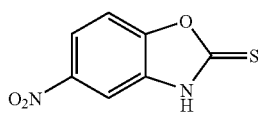

Combine 2-amino-4-nitrophenol (15.8 g, 102 mmol) and potassium ethyl xanthate (18.3 g, 114 mmol) in pyridine (200 mL). Heat the reaction at reflux for 1 h. Allow the reaction to cool to room temperature and pour into concentrated HCl (100 mL) and ice. Filter and wash the solids with 1N HCl to remove excess pyridine. Dry the solids under house vacuum at 50° C. for 2 days to obtain the title compound (15.85 g, 79%). ¹H NMR (400 MHz, DMSO-d6): δ 8.18 (dd, 1H, J=8.8, 2.2 Hz), 7.93 (d, 1H, J=2.2 Hz), 7.73 (d, 1H, J=8.8 Hz).

Preparation 138

2-Ethylsulfanyl-5-nitrobenzooxazole

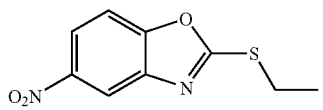

Dissolve 5-Nitro-3H-benzooxazole-2-thione (10.58 g, 53.9 mmol) in anhydrous THF (300 mL). Cool the mixture to 0° C. in an ice bath. Add NaH (4.90 g, 60% dispersion in mineral oil) slowly. Stir the resulting mixture at 0° C. for 10 min. Add iodoethane (20.0 mL, 0.250 mmol) to the stirring mixture. Allow the mixture to warm to room temperature and stir overnight. Adsorb the reaction mixture onto silica gel and subject to flash column chromatography in 2 batches (330 g, 120 g columns, eluting with 10-50% ethyl acetate/n-hexane both times) to yield the desired product (4.93 g, 41%). ¹H NMR (400 MHz, DMSO-d6): δ 8.47 (d, J=2.4 Hz, 1H), 8.23 (dd, J=9.2, 2.6 Hz, 1H), 7.88 (d, J=8.8 Hz, 1H), 3.37 (q, J=6.8 Hz, 2H), 1.45 (t, J=7.6 Hz, 3H).

Preparation 139

Methyl-(1-methyl-piperidin-4-yl)-(5-nitro-benzooxazol-2-yl)-amine

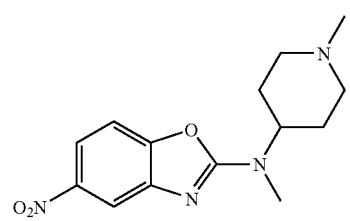

Dissolve 2-ethylsulfanyl-5-nitro-benzooxazole (1.17 g, 5.23 mmol) in anhydrous THF (10 mL) in a reaction tube and blow nitrogen into the vessel for 10 s. Add methyl-(1-methyl-piperidin-4-yl)-amine (1.37 mL, 9.42 mmol) to the solution. Quickly seal the vessel and immerse into a pre-heated oil bath (100° C.) and stir for 24 h. Concentrate the reaction mixture in vacuo, wash with 1.0M NaOH (aq) (2×50 mL), dry over Na₂SO₄, filter, and concentrate in vacuo. Subject the residue by silica gel flash column chromatography, eluting with 2N NH₃ in MeOH/CH₂Cl₂, to yield the desired product (0.608 g, 40%). MS (ES+) 291.0 (M+1)+.

Preparation 140

N²-Methyl-N²-(1-methyl-piperidin-4-yl)-benzooxazole-2,5-diamine

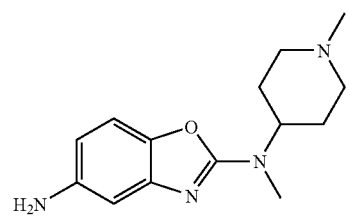

Dissolve methyl-(1-methyl-piperidin-4-yl)-(5-nitro-benzooxazol-2-yl)-amine (0.583 g, 2.01 mmol), in acetic acid (8 mL), and add iron (1.12 g, 20.1 mmol) to the solution. Stir the mixture at 40° C. for 3 h. Filter the reaction mixture through Celite® and wash with water/MeOH. Concentrate the reaction mixture in vacuo. Subject the residue to silica gel flash column chromatography, eluting with 10% 2N NH₃ in MeOH/CH₂Cl₂, to yield the desired product (0.474 g, 91%). MS (ES+) 261.2 (M+1)+.

Preparation 141

N,N,N'-Trimethyl-N'-(5-nitro-benzooxazol-2-yl)-ethane-1,2-diamine

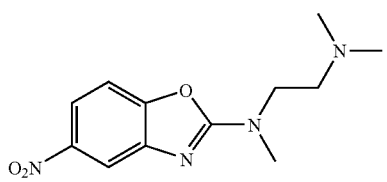

Prepare the title compound by essentially following the procedure as described in Preparation 139, using 2-methylsulfanyl-5-nitro-benzooxazole (5.0 g, 23.8 mmol) and N,N,N'-Trimethyl-ethane-1,2-diamine (15.4 mL, 118.9 mmol) at 140° C. The product is purified by silica gel flash column chromatography (330 g column, eluting with 5% 2N $NH_3$ in MeOH/$CH_2Cl_2$) to yield the desired product (2.8 g, 44%). MS (ES+) 265.3 $(M+1)^+$.

Preparation 142

$N^2$-(2-Dimethylamino-ethyl)-$N^2$-methyl-benzooxazole-2,5-diamine

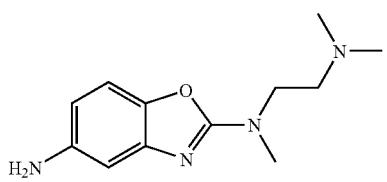

The title compound was prepared according to the procedure described in General Method B using N,N,N'-Trimethyl-N'-(5-nitro-benzooxazol-2-yl)-ethane-1,2-diamine (4.131 g, 15.63 mmol), acetic acid (50 mL), and Fe (8.72 g, 78.15 mmol), stirring for 3 h: (3.57 g, 98%): mass spectrum (m/e): 265.3 (M+1).

Example 59

2-(4-Chloro-phenyl)-5-{2-[(2-dimethylamino-ethyl)-methyl-amino]-benzooxazol-5-yl}-6,7-dihydro-5H-thiazolo[5,4-c]pyridin-4-one hydrochloride

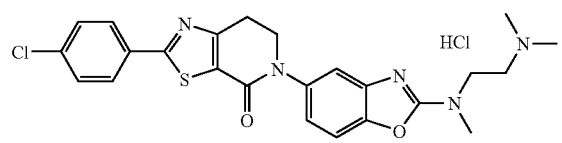

Dissolve $N^2$-(2-dimethylamino-ethyl)-$N^2$-methyl-benzooxazole-2,5-diamine (0.50 g, 2.14 mmol) in $CH_2Cl_2$ (10.0 mL) and treat with 2N aluminum trimethyl in hexanes (2.0 mL, 4.0 mmol). Stir at room temperature for 15 min and add 2-(4-chloro-phenyl)-6,7-dihydro-pyrano[4,3-d]thiazol-4-one (0.60 g, 2.26 mmol) neat and stir the reaction at room temperature for 2 h. Carefully quench the mixture with saturated Rochelles salt solution and stir at room temperature for 1 h. Dilute with water, filter the precipitate and dry. Dissolve the solid (0.30 g, 0.60 mmol) and treat with tributylphosphine (0.26 mL, 0.90 mmol) and diisopropylazodicarboxylate (0.18 mL, 0.09 mmol). Stir the reaction at room temperature for 18 h and concentrate. Purify the crude material by flash chromatography, using 0-10% 2N $NH_3$/MeOH in $CH_2Cl_2$ to give the free amine. Dissolve the free amine in MeOH (2.0 mL) and add 1N HCl in ether (1.0 mL), sonicate for 5 min, and concentrate. Triturate the solid with ether, filter, and dry to give the title compound (0.13 g). MS (ES+) 482 (M+1)+. $^1$H NMR (400 MHz, DMSO-d6): δ 10.59 (s, 1H), 8.01 (d, 2H, J=8.4 Hz), 7.58 (d, 2H, J=8.4 Hz), 7.44 (d, 1H, J=8.4 Hz), 7.30 (d, 1H, J=2.2 Hz), 7.03 (dd, 1H, J=8.4, 2.2 Hz), 4.07 (t, 2H, J=6.8 Hz), 3.92 (t, 2H, J=5.3 Hz), 3.39 (t, 2H, J=5.3 Hz), 3.24 (t, 2H, J=6.8 Hz), 3.17 (s, 3H), 2.81 (d, 6H, J=4.8 Hz).

Example 60

2-(4-Chloro-phenyl)-5-{2-[methyl-(1-methyl-piperidin-4-yl)-amino]-benzooxazol-5-yl}-6,7-dihydro-5H-thiazolo[5,4-c]pyridin-4-one

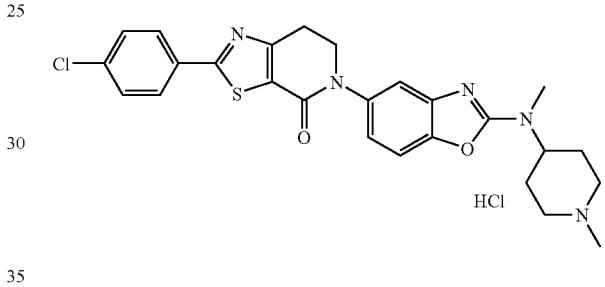

Prepare the title compound by essentially following the procedure as described in Example 59, using $N^2$-methyl-$N^2$-(1-methyl-piperidin-4-yl)-benzooxazole-2,5-diamine. MS (ES+) 508 (M+1, free amine)+. $^1$H NMR (400 MHz, DMSO-d6): δ 10.79 (brs, 1H), 8.04 (d, 2H, J=8.4 Hz), 7.62 (d, 2H, J=8.8 Hz), 7.45 (d, 1H, J=8.8 Hz), 7.31 (d, 1H, J=2.2 Hz), 7.04 (dd, 1H, J=8.6, 2.2 Hz), 4.39 (m, 1H), 4.10 (t, 2H, J=7.0 Hz), 3.48 (d, 2H, J=11.4 Hz), 3.28 (t, 2H, J=2.0 Hz), 3.17 (m, 2H), 3.04 (s, 3H), 2.73 (d, 3H, J=4.8 Hz), 2.27 (m, 2H), 1.94 (d, 2H, J=13.2 Hz).

Example 61

2-(4-Chloro-phenyl)-5-[3-methoxy-4-(3-pyrrolidin-1-yl-prop-1-ynyl)-phenyl]-6,7-dihydro-5H-thiazolo[5,4-c]pyridin-4-one

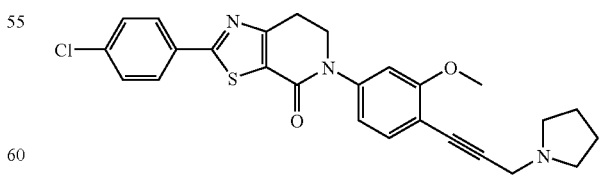

Treat a suspension of 5-(4-bromo-3-methoxy-phenyl)-2-(4-chloro-phenyl)-6,7-dihydro-5H-thiazolo[5,4-c]pyridin-4-one (0.25 mg, 0.56 mmol), 1-prop-2-ynyl-pyrrolidine (0.12 g, 1.10 mmol), dichlorobis(triphenylphosphine)palladium (II) (12.0 mg, 0.02 mmol), triethylamine (0.5 mL) in DMF with CuI (4.0 mg, 0.02 mmol). Stir at 80° C. under nitrogen for 2 days. Dilute the reaction with water and extract with CH$_2$Cl$_2$ (2×). Dry, filter, and concentrate the organic solution and purify the crude material by flash chromatography, using a gradient of 0-10% MeOH in CH$_2$Cl$_2$ to give the title compound (30.0 mg, 12%). MS (ES+) 478.0 (M+1)+. $^1$H NMR (400 MHz, CDCl$_3$): δ 7.89 (d, 2H, J=8.8 Hz), 7.40 (m, 3H), 6.95 (d, 1H, J=2.2 Hz), 6.82 (dd, 1H, J=8.1, 2.0 Hz), 4.10 (t, 2H, J=6.8 Hz), 3.84 (m, 5H), 3.26 (t, 2H, J=6.8 Hz), 2.88 (m, 4H), 1.89 (m, 4H).

Example 62

2-(4-Chloro-phenyl)-5-[4-(2-imidazol-1-yl-ethoxy)-3-methoxy-phenyl]-6,7-dihydro-5H-thiazolo[5,4-c]pyridin-4-one hydrochloride

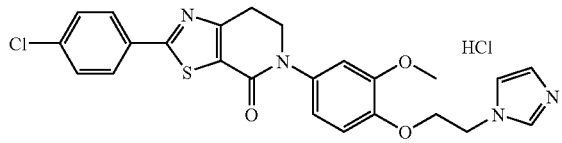

Treat a solution of 2-(4-chloro-phenyl)-5-(4-hydroxy-3-methoxy-phenyl)-6,7-dihydro-5H-thiazolo[5,4-c]pyridin-4-one (0.20 g, 0.52 mmol), 2-imidazol-1-yl-ethanol (0.09 g, 0.80 mmol), and triphenylphosphine (0.27 g, 1.03 mmol) with diisopropylazodicarboxylate (0.27 g, 1.34 mmol). Warm the solution to 80° C. and stir for 18 h. Concentrate the reaction and purify the residue by flash chromatography, using 0-10% 2N NH$_3$/MeOH in CH$_2$Cl$_2$, to give the free amine. Dissolve the free amine in MeOH (2.0 mL) and add 1N HCl in ether (2.0 mL), sonicate for 5 min. and concentrate. Triturate the solid with ether, filter, and dry to give the title compound (0.15 g, 58%). MS (ES+) 481 (M+1, free anine)+. $^1$H NMR (400 MHz, DMSO-d6): δ 14.84 (s, 1H), 9.17 (s, 1H), 8.00 (d, 2H, J=8.4 Hz), 7.79 (t, 1H, J=1.8 Hz), 7.67 (t, 1H, J=1.8 Hz), 7.57 (d, 2H, J=8.8 Hz), 7.00 (m, 2H), 6.86 (dd, 1H, J=8.6, 2.4 Hz), 4.58 (t, 2H, J=4.8 Hz), 4.35 (t, 2H, J=4.8 Hz), 4.01 (t, 2H, J=7.0 Hz), 3.70 (s, 3H), 3.21 (t, 2H, J=7.0 Hz).

Example 63

2-(4-Chloro-phenyl)-5-[3-chloro-4-(2-pyrrolidin-1-yl-ethoxy)-phenyl]-6,7-dihydro-5H-thiazolo[5,4-c]pyridin-4-one hydrochloride

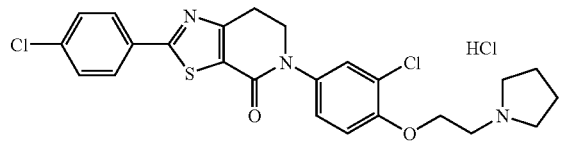

Treat a solution of 2-(4-chloro-phenyl)-5-[3-chloro-4-(2-pyrrolidin-1-yl-ethoxy)-phenyl]-6,7-dihydro-5H-thiazolo[5,4-c]pyridin-4-one (60.0 mg, 0.12 mmol) in MeOH (2.0 mL) with 1N HCl in ether (1.0 mL). Sonicate at room temperature for 15 min, concentrate, and dry to give the title compound (50 mg, 78%). MS (ES+) 488 (M+1; free amine)+. $^1$H NMR (400 MHz, DMSO-d6): δ 10.44 (s, 1H), 8.02 (d, 2H, J=8.6 Hz), 7.59 (m, 2H), 7.55 (d, 1H, J=2.4 Hz), 7.36 (dd, 1H, J=8.8, 2.4 Hz), 7.25 (d, 1H, J=8.8 Hz), 4.43 (t, 2H, J=4.8 Hz), 4.05 (t, 2H, J=7.0 Hz), 3.62 (m, 4H), 3.24 (t, 2H, J=7.0 Hz), 3.14 (m, 2H), 2.01 (m, 2H), 1.86 (m, 2H).

Example 64

2-(4-Chloro-phenyl)-5-[3-chloro-4-(2-pyrrolidin-1-yl-ethoxy)-phenyl]-5H-thiazolo[5,4-c]pyridin-4-one

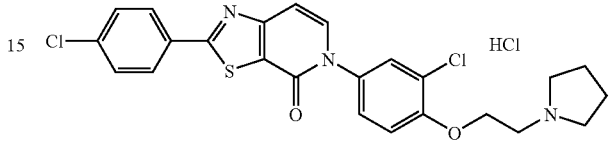

Treat a solution of 2-(4-chloro-phenyl)-4-(2-hydroxyethyl)-thiazole-5-carboxylic acid [3-chloro-4-(2-pyrrolidin-1-yl-ethoxy)-phenyl]-amide (0.15 g, 0.30 mmol) in CH$_2$Cl$_2$ (20 ml) with pyridinium dichromate (0.33 g, 0.88 mmol) and stir suspension at room temperature for 3 days. Apply reaction mixture onto silica gel chromatography column and purify using 0-10% 2N NH$_3$/MeOH in CH$_2$Cl$_2$, to give the free amine. Dissolve the free amine in MeOH (1.0 mL) and add 1N HCl in ether (0.5 mL), sonicate for 5 min, and concentrate. Triturate the solid with ether, filter, and dry to give the title compound (16 mg, 10%). MS (ES+) 486 (M+1, free amine)+. $^1$H NMR (400 MHz, DMSO-d6): δ 10.59 (s, 1H), 8.13 (d, 2H, J=8.8 Hz), 7.75 (d, 1H, J=7.3 Hz), 7.70 (d, 1H, J=2.6 Hz), 7.64 (d, 2H, J=8.8 Hz), 7.48 (dd, 1H, J=8.8, 2.4 Hz), 7.34 (d, 1H, J=8.8 Hz), 7.04 (d, 1H, J=7.5 Hz), 4.49 (t, 2H, J=4.9 Hz), 3.62 (m, 4H), 3.15 (m, 2H), 2.02-1.87 (m, 4H).

Preparation 143

Benzyl-(2-methyl-allyl)-amine

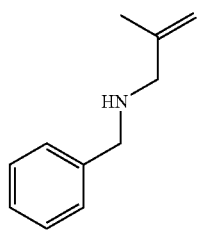

Add benzaldehyde (14.5 mL, 143 mmol) to a mixture of methallylamine (9.73 g, 137 mmol) and MgSO$_4$ (15.0 g, 125 mmol) in THF (180 mL). Stir for 22 h, filter the mixture, and concentrate the filtrate. Dissolve the residue in EtOH (200 mL) and treat with NaBH$_4$ (5.00 g, 132 mmol) in 3 portions. After 19 h, remove the solvent by rotary evaporation. Treat the residue with 1 M HCl (200 mL) then 5 M HCl (20 mL). Wash the solution with tert-butyl methyl ether (250 mL) and then treat with 5 M NaOH (50 mL) to make basic. Extract the mixture with CH$_2$Cl$_2$ (200 mL followed by 100 mL). Dry, filter and concentrate the organic solution to give the title compound (20.3 g, 92%) as a colorless liquid. $^1$H NMR (400

MHz, DMSO-d6): δ 7.2-7.4 (5H, m), 4.84 (1H, s), 4.79 (1H, s), 3.63 (2H, s), 3.03 (2H, s), 1.69 (3H, s).

Preparation 144

1-[Benzyl-(2-methyl-allyl)-amino]-2-methyl-propan-2-ol

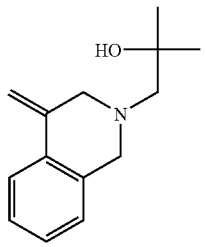

Add lithium bromide (955 mg, 11.0 mmol) to a mixture of isobutylene oxide (6.20 mL, 68.8 mmol) and benzyl-(2-methyl-allyl)-amine (9.51 g, 59.0 mmol). Stir the mixture for 3.5 h at room temperature then treat with additional epoxide (1.5 mL, 16.6 mmol) and heat at 60° C. for 1.7 h. Dilute the mixture with $CH_2Cl_2$ (200 mL) and wash with water (200 mL). Dry, filter and concentrate the organic solution. Dry the residue at 80° C. under vacuum to give the title compound (13.5 g, 98%) as a colorless oil. $^1$H NMR (400 MHz, DMSO-d6): δ 7.2-7.4 (5H, m), 4.90 (1H, s), 4.83 (1H, s), 4.18 (1H, s), 3.59 (2H, s), 2.98 (2H, s), 2.27 (2H, s), 1.71 (3H, s), 1.05 (6H, s).

Preparation 145

4-Benzyl-2-iodomethyl-2,6,6-trimethyl-morpholine

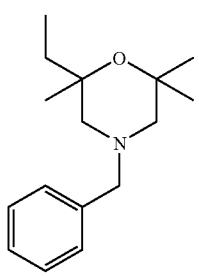

Add solid $I_2$ (21.1 g, 83.1 mmol) to a biphasic mixture of 1-[benzyl-(2-methyl-allyl)-amino]-2-methyl-propan-2-ol (17.6 g, 75.4 mmol) in tert-butyl methyl ether (250 mL) and 1 M $NaHCO_3$ (100 mL). Stir for 18 h and then add 1 M $Na_2S_2O_3$ (100 mL). Dilute the mixture with additional tert-butyl methyl ether (200 mL) and separate the organic solution. Wash the organic solution with a mixture of 1 M $Na_2S_2O_3$ (100 mL) and 1M $NaHCO_3$ (100 mL). Dry, filter, and concentrate the organic solution. Dry the residue at 60° C. under vacuum to give the title compound (25.2 g, 93%) as a golden oil. $^1$H NMR (400 MHz, DMSO-d6): δ 7.2-7.4 (5H, m), 3.49 (1H, d), 3.47 (2H, s), 3.41 (1H, s), 2.49 (1H, d), 2.23 (1H, s), 2.20 (1H, s), 2.10 (1H, d), 1.24 (3H, s), 1.22 (3H, s), 1.15 (3H, s).

Preparation 146

4-Benzyl-2,2,6,6-tetramethyl-morpholine

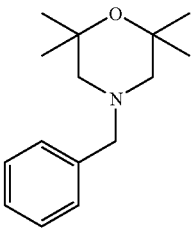

Add solid $NaBH_4$ (776 mg, 20.5 mmol) to a solution of 4-benzyl-2-iodomethyl-2,6,6-trimethyl-morpholine (6.22 g, 17.3 mmol) in DMSO (20 mL) and then heat the mixture at 100° C. After 2 h, add additional DMSO (10 mL). After an additional 1.25 h, add extra $NaBH_4$ (120 mg, 3.17 mmol). Remove the heat after an additional 1.25 h (total reaction time=4.5 h). Quench the excess $NaBH_4$ with 5 M HCl (20 ml). After 15 min, add 5 M NaOH (20 mL) and 1 M $Na_2S_2O_3$ (20 mL) and then stir the mixture overnight. Dilute the mixture with tert-butyl methyl ether (250 mL) and water (100 mL). Separate the organic solution and wash with additional water (4×100 mL). Dry, filter and concentrate the organic solution. Purify the residue by flash chromatography, using a gradient from 50% to 100% $CH_2Cl_2$ in pentane as eluent. Dry the product so obtained briefly at 60° C. under vacuum to give the title compound (2.43 g, 60%) as a colorless liquid. $^1$H NMR (400 MHz, DMSO-d6): δ 7.2-7.4 (5H, m), 3.45 (2H, s), 2.12 (4H, s), 1.15 (12H, s).

Preparation 147

2,2,6,6-Tetramethymorpholine

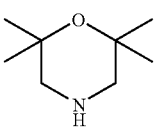

Dissolve 4-benzyl-2,2,6,6-tetramethylmorpholine (Bennett, G. B.; Houlihan, W. J.; Mason, R. B.; Engstrom, R. G. *J. Med. Chem.* 1976, 19, 709-714) (11.0 g, 47.1 mmol) in EtOH (650 mL) and add 3% Pd/C (8.61 g). Shake the mixture under hydrogen (60 psi) at 40° C. for 24 h. Filter the mixture to remove Pd catalyst, and treat the filtrate with 2M HCl in ether, then concentrate. Dry the residue at 80° C. under vacuum to give the title compound (6.79 g) as a white solid. $^1$H NMR (DMSO-d6, 400 MHz) δ 9.8 (2H, br s), 2.88 (4H, s), 1.25 (12H, s).

Preparation 148

4-(2-Benzyloxy-ethyl)-2,2,6,6-tetramethyl-morpholine

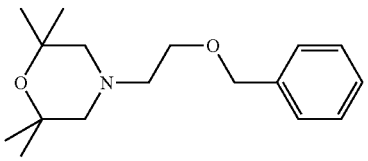

Dissolve 500 mg (2.79 mmol) of 2,2,6,6-tetramethyl-morpholine (500 mg, 2.79 mmol) in dichloroethane (10 mL). Add benzyloxy-acetaldehyde (470 µl, 3.35 mmol) and stir at room temperature for 20 min. Add sodium triacetoxyborohydride (770 mg, 3.63 mmol) and continue stirring at room temperature for 20 h. Pour the reaction mixture into 100 mL of 1N NaOH (100 mL) and extract with $CH_2Cl_2$ (2×100 mL). Wash the combined organic layers with brine (100 mL). Purify using silica gel chromatography, using a gradient of 0% to 10% (2N NH3 in MeOH)/CHCl3 as eluent, to give 490 mg (63%) of the desired product. MS (ES+) 278.3 (M+1)+.

Preparation 149

2-(2,2,6,6-Tetramethyl-morpholin-4-yl)-ethanol

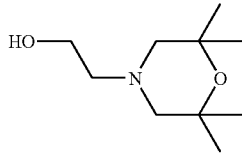

Dissolve 4-(2-benzyloxy-ethyl)-2,2,6,6-tetramethyl-morpholine (490 mg, 1.77 mmol) MeOH (40 mL). Add to a pressure vessel containing a slurry of 10% Pd/C (100 mg) in MeOH (20 mL). Pressurize with 45 psi hydrogen gas. Monitor the reaction by MS. After 48 h, add another portion of 10% Pd/C (100 mg) and re-pressurize to 45 psi hydrogen. Stir an additional 3 days. Filter the reaction mixture through Celite® eluting with MeOH. Concentrate to give the desired product in quantitative yield. MS (ES+) 188.3 (M+1)+.

Example 65

2-(4-Chloro-phenyl)-5-{3-methoxy-4-[2-(2,2,6,6-tetramethyl-morpholin-4-yl)-ethoxy]-phenyl}-5H-thiazolo[5,4-c]pyridine-4-one Hydrochloride

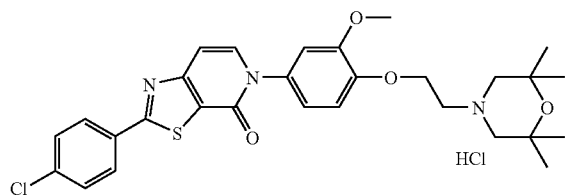

Dissolve 2-(2,2,6,6-tetramethyl-morpholin-4-yl)-ethanol (100 mg, 0.53 mmol) $CH_2Cl_2$ (5 mL). Add triethylamine (96 µL, 0.69 mmol) and then cool the reaction to 0° C. Add methanesulfonyl chloride (53 µL, 0.69 mmol) and stir for 2 h. Add more methanesulfonyl chloride (53 µL, 0.69 mmol) and stir 1 h. Add more methanesulfonyl chloride (53 µL, 0.69 mmol) and triethyl amine (96 µL, 0.69 mmol). Store in freezer (−4° C.) overnight. Pour the reaction mixture into 1N NaOH (100 mL) and extract with $CH_2Cl_2$ (2×100 mL). Wash the combined organics with brine (100 mL). Concentrate the organic portion to give crude mesylate which is dissolved in 1-methyl-2-pyrrolidinone (2 mL). Add this solution to a room temperature slurry of 2-(4-chloro-phenyl)-5-(4-hydroxy-3-methoxy-phenyl)-5H-thiazolo[5,4-c]pyridin-4-one (204 mg, 0.53 mmol) and NaH (21 mg, 0.53 mmol) in 1-methyl-2-pyrrolidinone (6 mL). Stir at room temperature for 2 h and then warm to 80° C. for 48 h. Cool to room temperature and pour into 1N NaOH (200 mL) and extract with EtOAc (2×200 mL). Purify via silica gel chromatography, using a gradient of 0% to 10% (2N NH3 in MeOH)/CHCl3 as eluent to give a mixture of product and recovered phenol. Dissolve the mixture in $CH_2Cl_2$ (100 mL) and extract with 1N NaOH (5×100 mL). Concentrate to give the pure product as the free amine. Dissolve in $CH_2Cl_2$ (20 mL) and add 4M HCl in dioxane (200 µL). Concentrate to give the product as the hydrochloride salt. MS (ES+) 554.3 (M+1)+, $^1$H NMR (400 MHz, DMSO-d6) δ 10.11 (bs, 1H), 8.12 (d, J=9.0 Hz, 2H), 7.70 (d, J=7.2 Hz, 1H), 7.63 (d, J=9.0 Hz, 2H), 7.19-7.16 (m, 2H), 7.02 (d, J=7.2 Hz, 2H), 4.52 (bs, 2H), 3.77 (s, 3H), 3.59-3.54 (m, 4H), 2.95 (t, J=10.0 Hz, 2H), 1.41 (s, 6H), 1.16 (s, 6H).

Preparation 150

2-[Benzyl-(2-methyl-allyl)-amino]-ethanol

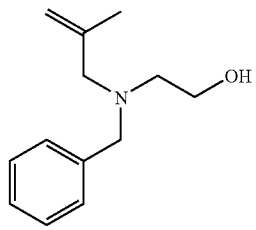

Add methallyl chloride (68.8 g, 0.760 mol, Aldrich) to a mixture of N-benzylethanolamine (100 g, 0.663 mol) and potassium carbonate (139 g, 1.00 mol) in water (600 mL). Heat the mixture to 62° C. for 23 h and then transfer to a separatory funnel. Extract the product with tert-butyl methyl ether (500 mL). Dry, filter, and concentrate the organic solution to give the title compound (131 g, 96%) as a colorless liquid. $^1$H NMR (DMSO-d6, 400 MHz) δ 7.20-7.33 (5H, m), 4.92 (1H, br s), 4.83 (1H, br s), 4.35 (1H, t), 3.53 (2H, s), 3.44-3.50 (2H, m), 2.94 (1H, s), 2.42 (2H, t), 1.69 (1H, s).

Preparation 151

4-Benzyl-2,2-dimethyl-morpholine

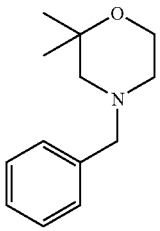

Add 2-[benzyl-(2-methyl-allyl)-amino]-ethanol (13.0 g, 63.2 mmol) to a slurry of mercury (It) acetate (20.7 g, 65.0 mmol) in water (45 mL) and THF (45 mL). After 3 h, treat the mixture with NaOH (25 mL, 2.5 M aqueous, 125 mmol) followed by NaBH$_4$ (2.72 g, 71.9 mmol). After 19 h, decant the mixture away from the metallic mercury and add to a separatory funnel with tert-butyl methyl ether (250 mL). Separate the organic solution, wash with water (250 mL), filter through a silica plug, and concentrate. Purify the residue by flash chromatography using a gradient from 5% to 10% tert-butyl methyl ether in CH$_2$Cl$_2$. Collect and concentrate the fractions containing product then dissolve the residue in hexanes (100 mL). Filter the solution through Celite® to remove metallic mercury and then concentrate the filtrate to give the title compound (7.01 g, 54%) as a colorless liquid. $^1$H NMR (DMSO-d6, 400 MHz) δ 7.20-7.40 (5H, m), 3.60 (2H, m), 3.42 (2H, s), 2.29 (2H, m), 2.10 (2H, s), 1.14 (6H, s).

Preparation 152

2,2-Dimethylmorpholine hydrochloride

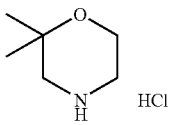

Dissolve 4-benzyl-2,2-dimethyl-morpholine (5.67 g, 27.6 mmol) in CH$_2$Cl$_2$ (50 mL) and add 1-chloroethyl chloroformate (4.60 mL, 42.2 mmol) while stirring at room temperature. After 4 h, concentrate the solution and treat the residue with MeOH (60 mL). Heat the mixture at 60° C. for 2 h, then concentrate again. Dissolve the residue in water (125 mL) and wash with tert-butyl methyl ether (125 mL). Concentrate the aqueous layer and dry the resulting residue at 80° C. under vacuum to give the title compound (3.91 g, 93%) as a white solid. $^1$H NMR (DMSO-d6, 400 MHz) δ 9.52 (2H, br s), 3.75 (2H, m), 2.89-2.96 (4H, m), 1.25 (6H, s).

Preparation 153

2-(2,2-Dimethyl-morpholin-4-yl)-ethanol

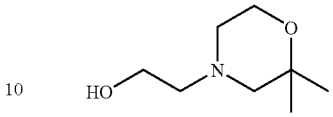

Dissolve 2,2-dimethylmorpholine (151 mg, 1.0 mmol) in 1,2-dichloroethane (3 mL) and add glycolaldehyde (60 mg, 1.0 mmol). Stir at room temperature for 30 min followed by addition of NaBH(OAc)$_3$ (233 mg, 1.1 mmol). Stir 3 h, then quench by adding 30 mL of 1N NaOH. Pour into a separatory funnel and extract with EtOAc (2×50 mL). Wash the combined organic layers with brine (50 mL). The crude alcohol was used as is without further purification. MS (ES+) 160.2 (M+1)$^+$.

Example 66

2-(4-Chloro-phenyl)-5-{4-[2-(2,2-dimethyl-morpholin-4-yl)-ethoxy]-3-methoxy-phenyl}-5H-thiazolo[5,4-c]pyridin-4-one

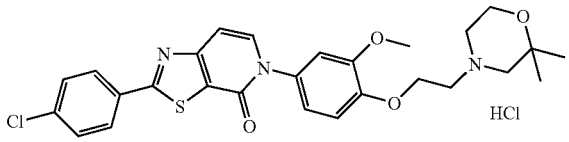

Dissolve 2-(2,2-dimethyl-morpholin-4-yl)-ethanol (88 mg, 0.55 mmol) in 4.5 mL THF (4.5 mL). Add 2-(4-chlorophenyl)-5-(4-hydroxy-3-methoxy-phenyl)-5H-thiazolo[5,4-c]pyridin-4-one (211 mg, 0.55 mmol). This forms a slurry to which is added 217 mg (0.83 mmol) of triphenylphosphine (217 mg, 0.83 mmol) followed by 161 µL (0.83 mmol) of diisopropyl azodicarboxylate (DIAD). The reaction then becomes a solution. Heat the reaction to 80° C. for 16 h. Pour into 1N NaOH (200 mL) and extract with CH$_2$Cl$_2$ (2×150 mL). Purify via silica gel chromatography, using a gradient of 0% to 10% (2N NH3 in MeOH)/CHCl3 as eluent, to obtain a mixture of product and starting phenol. Dissolve the mixture in CH$_2$Cl$_2$ (300 mL) and extract with 5N NaOH (5×100 mL) until all the phenol is removed from the organic layer. Wash the organic layer with brine (100 mL) and concentrate. Dissolve the residue in CH$_2$Cl$_2$ (30 mL) and treat with 4M HCl in dioxane (100 µL). Diethyl ether is added until the solution becomes cloudy. Let sit at room temperature for 1.5 h then filter the resulting precipitate to give 18 mg (6%) of the desired product. MS (ES+) 526.0 (M+1)$^+$, $^1$H NMR (400 MHz, (CD$_3$OD): δ 8.11 (d, J=8.5 Hz, 2H), 7.66 (d, J=7.3 Hz, 1H), 7.56 (d, J=8.5 Hz, 2H), 7.19 (d, J=8.5 Hz, 1H), 7.17 (d, J=2.0 Hz, 1H), 7.09 (d, J=7.3 Hz, 1H), 7.01 (dd, J=8.5, 2.0 Hz, 1H), 4.51-4.43 (m, 2H), 4.07-4.00 (m, 2H), 3.93-3.90 (m, 1H), 3.89 (s, 3H), 3.70-3.56 (m, 4H), 3.26-3.19 (m, 1H), 3.07 (d, J=12.2 Hz, 1H), 1.44 (s, 3H), 1.30 (s, 3H).

We claim:
1. A compound of formula I

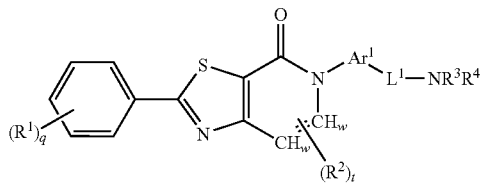

wherein:
" """-----" " is optionally a bond to form a double bond
q is 0, 1, 2, or 3; wherein other positions on the phenyl ring have hydrogen atoms;
t is 2;
w is 1 or 2 depending on substitution pattern and/or the presence of a double bond;
$R^1$ is independently selected from hydrogen, $C_1$-$C_8$ alkyl, $C_2$-$C_8$ alkenyl, $C_2$-$C_8$ alkynyl, halo, hydroxy, $C_1$-$C_8$ haloalkyl, $C_1$-$C_8$ alkoxy, —$C_1$-$C_8$ alkyl alcohol, $C_1$-$C_8$ haloalkoxy, aryl, —O-aryl, —O-heteroaryl, —O$C_1$-$C_8$ alkylaryl, —$C_1$-$C_8$ alkylaryl, —$C_1$-$C_8$ alkylheteroaryl, heterocyclic, —$C_1$-$C_8$ alkylheterocyclic, —$C_1$-$C_8$ alkylcycloalkyl, amino, and $C_1$-$C_8$ alkyl$NR^6R^{6'}$, $C_0$-$C_8$ alkyl$COOR^6$, $C_o$-$C_8$ alkyl$CONR^6R^{6'}$;
$R^2$ is independently selected from the group consisting of hydrogen;
$Ar^1$ is a cyclic group optionally substituted with one to three groups independently selected from the group consisting of $C_1$-$C_8$ alkyl, $C_2$-$C_8$ alkenyl, $C_2$-$C_8$ alkynyl, hydroxy, —O$C_1$-$C_8$ alkyl, $C_1$-$C_8$ alkylaryl, $C_1$-$C_8$ alkylheteroaryl, phenyl, —O-aryl, —O-heteroaryl, heterocyclic, $C_1$-$C_4$ alkylheterocyclic, cycloalkyl, $C_1$-$C_8$ alkylcycloalkyl, cyano, —$C_1$-$C_8$ alkyl$NR^6R^{6'}$, $C_1$-$C_8$ haloalkyl, $C_1$-$C_8$ alkyl alcohol, $C_1$-$C_8$ haloalkoxy, halo, $(CH_2)_nCOR^6$, —O$(CH_2)_nCHR^6R^{6'}$, $NR^6SO_2R^{6'}$, $(CH_2)_n$ $NR^6SO_2R^{6'}$, and —$(CH_2)_nC(O)NR^6R^{6'}$;
$L^1$ is a bond or a divalent linker selected from the group consisting of $C_1$-$C_5$ alkyl, $C_2$-$C_5$ alkynyl, $C_2$-$C_5$ alkenyl, $C_0$-$C_5$ alkyl-S—$C_0$-$C_5$ alkyl, $C_0$-$C_5$ alkyl-S—$C_1$-$C_5$ alkylhalide, $C_0$-$C_5$ alkyl-$NR^6$—$C_0$-$C_5$ alkyl, $C_0$-$C_5$ alkyl-$NR^6$— $C_1$-$C_5$ alkyl-S—$C_0$-$C_5$ alkyl wherein each $L^1$ group has a maximum of 6 carbon atoms in the main chain and wherein each alkyl is optionally substituted with 1 to 3 groups independently selected from halo, cyano, and hydroxy;
$R^3$ and $R^4$ are independently selected from the group consisting of hydrogen, $C_1$-$C_8$ alkyl, $C_2$-$C_8$ alkenyl, $C_3$-$C_8$ cycloalkyl, aryl, heteroaryl heterocyclic, $C_1$-$C_8$ alkylaryl, $C_1$-$C_8$ alkylcycloalkyl, $C_1$-$C_8$ alkylheteroaryl, $C_1$-$C_4$ alkylheterocyclic; wherein each of the alkyl, alkenyl, cycloalkyl, aryl, heteroaryl, or heterocyclic group or subgroup is optionally substituted with one to three groups independently selected from $C_1$-$C_8$ alkyl, $C_2$-$C_8$ alkenyl, phenyl, alkylaryl, $(CH_2)_nNSO_2C_1$-$C_8$ alkyl, $(CH_2)_nNSO_2$phenyl, $(CH_2)_nNSO_2$aryl, —$C(O)C_1$-$C_8$ alkyl, COOH, —$C(O)OC_1$-$C_8$ alkyl and $C_0$-$C_4$ alkyl$NR^6R^{6'}$; and wherein $R^3$ and $R^4$ optionally combine together with the nitrogen atom to which they are attached, or one or both of $R^3$ and $R^4$ combine with $L^1$ at a position α, β, γ, or, δ to the nitrogen of $NR^3R^4$ to form a nitrogen containing 5 to 7-member heterocyclic group with $L^1$ said heterocyclic group optionally having one to three substituents independently selected from oxo, hydroxy, cyano, $C_1$-$C_8$ alkyl, $C_2$-$C_8$ alkenyl, $C_3$-$C_8$ cycloalkyl, $C_1$-$C_8$ alkylaryl, $C_1$-$C_8$ alkylcycloalkyl, $C_1$-$C_4$ alkylheterocyclic, $C_1$-$C_4$ alkylheteroaryl, halo, $(CH_2)_nNSO_2C_1$-$C_8$ alkyl, $(CH_2)_nNSO_2$phenyl, $(CH_2)_n$ $NSO_2$aryl, —$C(O)C_1$-$C_8$ alkyl, —$C(O)OC_1$-$C_8$ alkyl and $C_0$-$C_4$ alkyl$NR^6R^{6'}$;
$R^6$ and $R^{6'}$ are independently hydrogen, $C_1$-$C_8$ alkyl, phenyl, aryl, $C_1$-$C_8$ alkylaryl, $C_3$-$C_8$ cycloalkyl, or $C_1$-$C_6$ alkylcycloalkyl; and wherein $R^6$ and $R^{6'}$ may combine to form a substituted 5-7 member nitrogen-containing heterocycle, optionally having one to three substituents independently selected from oxo, hydroxy, cyano, $C_1$-$C_8$ alkyl, $C_2$-$C_8$ alkenyl, $C_3$-$C_8$ cycloalkyl, $C_1$-$C_8$ alkylaryl, $C_1$-$C_8$ alkylcycloalkyl, $C_1$-$C_4$ alkylheterocyclic, halo, $(CH_2)_nNSO_2C_1$-$C_8$ alkyl, $(CH_2)_n$ $NSO_2$phenyl, $(CH_2)_nNSO_2$aryl, —$C(O)C_1$-$C_8$ alkyl, COOH, or —$C(O)OC_1$-$C_8$ alkyl and $C_0$-$C_4$ alkyl$NR^7R^8$;
$R^7$ and $R^8$ are each independently selected from hydrogen, and $C_1$-$C_4$ alkyl; n is an integer from 0 to 4, or a pharmaceutically acceptable salt, enantiomer, diastereomer or mixture of or diastereomer thereof.

2. A compound according to claim 1 wherein the $R^1$ is halo, $C_1$-$C_3$ alkyl, $C_2$-$C_4$ alkenyl, $C_1$-$C_3$ haloalkyl, $C_1$-$C_3$ alkoxy, $C_1$-$C_3$ alkyl alcohol, $C_1$-$C_3$ haloalkoxy, $C_1$-$C_3$ alkylcycloalkyl, amino, and —$N(C_1$-$C_3$ alkyl$)_2$.

3. A compound according to claim 1 wherein $R^1$ is chloro, methoxy, amino, or —$N(CH_3)_2$.

4. A compound according to claim 1 wherein the group $L^1$ is a bond or a divalent linker selected from the group consisting of: —C(O)—, —$CH_2$—, —$CH_2CH_2$—, —$CH_2CH_2CH_2$, —$NHCH_2CH_2$—, —$N(CH_3)CH_2CH_2$—, —$OCH_2$—, —$OCH_2CH_2$, —$OCH_2CH_2CH_2$, and -acetyleneCH₂—CH₂—.

5. A compound according to claim 1 wherein $Ar^1$ is selected from the group consisting of phenyl, benzimidazolyl, 1H-indazolyl, 2-methylindolyl, 3-methoxyphenyl, 2,3-dimethylindolyl, 1-methylindolyl, benzo-1,4-oxazin, 4-methylquinolinyl-6yl, 2,3-dihydroindolyl, oxazolyl, and 3-chlorophenyl.

6. A compound according to claim 5 wherein said $Ar^1$ group is substituted with 1 to 2 groups independently selected from $C_1$-$C_3$ alkyl, $C_1$-$C_3$ alkylamino, $C_1$-$C_6$ haloalkyl, halo, $C_1$-$C_3$ alkoxy, and $C_1$-$C_3$ haloalkoxy.

7. A compound according to claim 1 wherein $R^3$ and $R^4$ combine with the nitrogen atom to form an optionally substituted pyridinyl, piperidinyl, pyrrolidinyl, imidazolidinyl, pyrazolinyl, piperazinyl, thiazolyl, piperidinyl, and morpholinyl.

8. A compound according to claim 7 wherein said optional substituent is selected from the group consisting of $C_1$-$C_3$ alkyl, $C_1$-$C_3$ alkylamino, $C_1$-$C_3$ haloalkyl, halo, $C_1$-$C_3$ alkoxy, and $C_1$-$C_3$ haloalkoxy.

9. A compound according to claim 1 wherein $R^3$ and $R^4$ are independently selected from the group consisting of $C_1$-$C_6$ alkyl, $C_1$-$C_6$ alkylamine, $C_1$-$C_6$ alkyl$NR^6R^{6'}$, pyrrolidinyl, methylpyrrolidinyl, phenyl, benzyl, cyclopentyl, cyclohexyl, methylcyclopropane and methylcyclobutane or combine with one, two, or three adjacent carbon atoms on the L group to form a piperidinyl, pyrrolidinyl, pyridinyl, piperazinyl, imidazolidinyl, and methylimidazolidinyl.

10. A compound selected from the group consisting of:
2-(4-Chloro-phenyl)-5-{4-[2-(isopropyl-methyl-amino)-ethoxy]-3-methoxy-phenyl}-6,7-dihydro-5H-thiazolo [5,4-c]pyridin-4-one,
2-(4-Chloro-phenyl)-5-[1-((S)-pyrrolidine-3-carbonyl)-2,3-dihydro-1H-indol-5-yl]-6,7-dihydro-5H-thiazolo[5,4-c]pyridin-4-one, triflate salt, 2-(4-Chloro-phenyl)-5-[4-(2-diethylamino-ethoxy)-3-methoxy-phenyl]-6,7-dihydro-5H-thiazolo[5,4-c]pyridin-4-one, 2-(4-Chloro-phenyl)-5-[3-methoxy-4-(2-pyrrolidin-1-yl-ethoxy)-phenyl]-6,7-dihydro-5H-thiazolo[5,4-c]pyridin-4-one, 5-[3-Methoxy-4-(3-methyl-3H-imidazol-4-ylmethoxy)-phenyl]-2-(4-trifluoromethoxy-phenyl)-5H-thiazolo[5,4-c]pyridin-4-one, hydrochloride salt, 2-(4-Chloro-phenyl)-5-{2-[methyl-(1-methyl-piperidin-4-yl)-amino]-benzooxazol-5-yl}-6,7-dihydro-5H-thiazolo[5,4-c]pyridin-4-one, hydrochloride salt 5-[3-Methoxy-4-(3-methyl-3H-imidazol-4-ylmethoxy)-phenyl]-2-(4-methoxy-phenyl)-5H-thiazolo[5,4-c]pyridin-4-one, hydrochloride salt, 2-(4-Methoxy-phenyl)-5-[3-methoxy-4-(2-pyrrolidin-1-yl-ethoxy)-phenyl]-6,7-dihydro-5H-thiazolo[5,4-c]pyridin-4-one, 2-(4-Chloro-phenyl)-5-[3-methoxy-4-(2-piperidin-1-yl-ethoxy)-phenyl]-6,7-dihydro-5H-thiazolo[5,4-c]pyridin-4-one, 2-(4-Chloro-phenyl)-5-{3-methoxy-4-[2-(3-oxo-morpholin-4-yl)-ethoxy]-phenyl}-5H-thiazolo[5,4-c]pyridin-4-one, 2-(4-Chloro-phenyl)-5-[4-(2-pyrrolidin-1-yl-ethyl)-3,4-dihydro-2H-benzo[1,4]oxazin-7-yl]-6,7-dihydro-5H-thiazolo[5,4-c]pyridin-4-one, 2-(2,4-Dichloro-phenyl)-5-[3-methoxy-4-(2-pyrrolidin-1-yl-ethoxy)-phenyl]-6,7-dihydro-5H-thiazolo[5,4-c]pyridin-4-one, 2-(4-Chloro-phenyl)-5-{2-[(2-dimethylamino-ethyl)-methyl-amino]-benzooxazol-5-yl}-6,7-dihydro-5H-thiazolo[5,4-c]pyridin-4-one, hydrochloride salt, 2-(4-Chloro-phenyl)-5-{4-[2-(cyclohexyl-methyl-amino)-ethoxy]-3-methoxy-phenyl}-6,7-dihydro-5H-thiazolo[5,4-c]pyridin-4-one, 2-(4-Chloro-phenyl)-5-[4-(3-dimethylamino-propoxy)-3-methoxy-phenyl]-6,7-dihydro-5H-thiazolo[5,4-c]pyridin-4-one, 2-(4-Chloro-phenyl)-5-[4-methyl-2-(2-morpholin-4-yl-ethylamino)-quinolin-6-yl]-6,7-dihydro-5H-thiazolo[5,4-c]pyridin-4-one, 2-(4-Chloro-phenyl)-5-[3-methoxy-4-(2-pyrrolidin-1-yl-ethoxy)-phenyl]-5H-thiazolo[5,4-c]pyridin-4-one, 2-(4-Chloro-phenyl)-5-[4-(2-dimethylamino-ethoxy)-3-methoxy-phenyl]-6,7-dihydro-5H-thiazolo[5,4-c]pyridin-4-one, 2-(4-Chloro-phenyl)-5-[1-(2-pyrrolidin-1-yl-ethyl)-1H-indol-5-yl]-6,7-dihydro-5H-thiazolo[5,4-c]pyridin-4-one, 2-(4-Chloro-phenyl)-5-[3-methoxy-4-(2-pyrrolidin-1-yl-ethoxy)-phenyl]-5H-thiazolo[5,4-c]pyridin-4-one citrate salt, 2-(4-Chloro-phenyl)-5-[3-chloro-4-(2-pyrrolidin-1-yl-ethoxy)-phenyl]-5H-thiazolo[5,4-c]pyridin-4-one, hydrochloride salt, 2-(4-Chloro-phenyl)-5-[3-methoxy-4-(2-pyrrolidin-1-yl-ethoxy)-phenyl]-5H-thiazolo[5,4-c]pyridin-4-one, hydrochloride salt, 2-(4-Chloro-phenyl)-5-[3-methoxy-4-(2-pyrrolidin-1-yl-ethoxy)-phenyl]-5H-thiazolo[5,4-c]pyridin-4-one, 2-(4-Chloro-phenyl)-5-[3-methoxy-4-(3-pyrrolidin-1-yl-propyl)-phenyl]-5H-thiazolo[5,4-c]pyridin-4-one, hydrochloride salt, 2-(4-Chloro-phenyl)-5-[3-methoxy-4-(2-morpholin-4-yl-ethoxy)-phenyl]-5H-thiazolo[5,4-c]pyridin-4-one, hydrochloride salt, 2-(4-Methoxy-phenyl)-5-[3-methoxy-4-(2-pyrrolidin-1-yl-ethoxy)-phenyl]-5H-thiazolo[5,4-c]pyridin-4-one, hydrochloride salt 2-(4-Chloro-phenyl)-5-[1-methyl-3-(2-pyrrolidin-1-yl-ethyl)-1H-indol-6-yl]-6,7-dihydro-5H-thiazolo[5,4-c]pyridin-4-one, hydrochloride salt, 5-[3-Methoxy-4-(2-pyrrolidin-1-yl-ethoxy)-phenyl]-2-(4-trifluoromethoxy-phenyl)-5H-thiazolo[5,4-c]pyridin-4-one, hydrochloride salt, 2-(4-Chloro-phenyl)-5-[3-methoxy-4-(3-pyrrolidin-1-yl-propyl)-phenyl]-5H-thiazolo[5,4-c]pyridin-4-one, 2-(4-Chloro-phenyl)-5-[4-(2-dimethylamino-ethoxy)-3-methoxy-phenyl]-6,7-dihydro-5H-thiazolo[5,4-c]pyridin-4-one, 2-(4-Chloro-phenyl)-5-[3-methoxy-4-(3-methyl-3H-imidazol-4-ylmethoxy)-phenyl]-5H-thiazolo[5,4-c]pyridin-4-one, hydrochloride salt, 2-(4-Chloro-phenyl)-5-[1-(2-pyrrolidin-1-yl-ethyl)-1H-indol-5-yl]-6,7-dihydro-5H-thiazolo[5,4-c]pyridin-4-one, 2-(4-Chloro-phenyl)-5-{4-[2-(2,2-dimethyl-morpholin-4-yl)-ethoxy]-3-methoxy-phenyl}-5H-thiazolo[5,4-c]pyridin-4-one, hydrochloride salt, 5-[4-(2-Dimethylamino-ethoxy)-3-methoxy-phenyl]-2-(4-methoxy-phenyl)-6,7-dihydro-5H-thiazolo[5,4-c]pyridin-4-one, hydrochloride salt, 2-(4-Chloro-phenyl)-5-[1-methyl-3-(2-pyrrolidin-1-yl-ethyl)-1H-indol-6-yl]-6,7-dihydro-5H-thiazolo[5,4-c]pyridin-4-one, 2-(4-Chloro-phenyl)-5-[3-chloro-4-(2-pyrrolidin-1-yl-ethoxy)-phenyl]-6,7-dihydro-5H-thiazolo[5,4-c]pyridin-4-one, hydrochloride salt, 2-(4-Chloro-phenyl)-5-[3-methoxy-4-(3-pyrrolidin-1-yl-propyl)-phenyl]-6,7-dihydro-5H-thiazolo[5,4-c]pyridin-4-one, 2-(4-Chloro-phenyl)-5-[2-methyl-1-(2-pyrrolidin-1-yl-ethyl)-1H-indol-5-yl]-6,7-dihydro-5H-thiazolo[5,4-c]pyridin-4-one, 2-(4-Chloro-phenyl)-5-[3-methoxy-4-(3-pyrrolidin-1-yl-propyl)-phenyl]-6,7-dihydro-5H-thiazolo[5,4-c]pyridin-4-one, hydrochloride salt, 2-(4-Chloro-phenyl)-5-[3-methoxy-4-(3-pyrrolidin-1-yl-prop-1-ynyl)-phenyl]-6,7-dihydro-5H-thiazolo[5,4-c]pyridin-4-one, 5-[3-Methoxy-4-(2-pyrrolidin-1-yl-ethoxy)-phenyl]-2-(4-trifluoromethyl-phenyl)-6,7-dihydro-5H-thiazolo[5,4-c]pyridin-4-one, 2-(4-Chloro-phenyl)-5-{3-methoxy-4-[2-(2,2,6,6-tetramethyl-morpholin-4-yl)-ethoxy]-phenyl}-5H-thiazolo[5,4-c]pyridin-4-one, hydrochloride salt, 2-(4-Chloro-phenyl)-5-[1-(2-pyrrolidin-1-yl-ethyl)-1H-benzoimidazol-5-yl]-6,7-dihydro-5H-thiazolo[5,4-c]pyridin-4-one, 2-(4-Chloro-phenyl)-5-[3-methoxy-4-((R)-1-morpholin-2-ylmethoxy)-phenyl]-6,7-dihydro-5H-thiazolo[5,4-c]pyridin-4-one, hydrochloride salt, 2-(4-Chloro-phenyl)-5-[2,3-dimethyl-1-(2-pyrrolidin-1-yl-ethyl)-1H-indol-5-yl]-6,7-dihydro-5H-thiazolo[5,4-c]pyridin-4-one, 5-[4-(2-[1,4']Bipiperidinyl-1'-yl-ethoxy)-3-methoxy-phenyl]-2-(4-chloro-phenyl)-6,7-dihydro-5H-thiazolo[5,4-c]pyridin-4-one, 2-(4-Chloro-phenyl)-5-[1-(2-morpholin-4-yl-ethyl)-1H-indol-5-yl]-6,7-dihydro-5H-thiazolo[5,4-c]pyridin-4-one, hydrochloride salt, or a pharmaceutically acceptable salt, enantiomer, or mixture of enantiomers thereof.

11. A pharmaceutical composition comprising a compound of claim 1 and a pharmaceutically acceptable carrier and/or diluent.

* * * * *